United States Patent
Davis et al.

(10) Patent No.: US 10,639,319 B2
(45) Date of Patent: *May 5, 2020

(54) HUMAN MILK OLIGOSACCHARIDES FOR PREVENTING INJURY AND/OR PROMOTING HEALING OF THE GASTROINTESTINAL TRACT

(75) Inventors: Steven R. Davis, Columbus, OH (US); Jomay Chow, Gahanna, OH (US)

(73) Assignee: ABBOTT LABORATORIES, Abbott Park, IL (US)

( * ) Notice: Subject to any disclaimer, the term of this patent is extended or adjusted under 35 U.S.C. 154(b) by 288 days.

This patent is subject to a terminal disclaimer.

(21) Appl. No.: 14/238,822

(22) PCT Filed: Aug. 13, 2012

(86) PCT No.: PCT/US2012/050569
§ 371 (c)(1),
(2), (4) Date: Jun. 13, 2014

(87) PCT Pub. No.: WO2013/032674
PCT Pub. Date: Mar. 7, 2013

(65) Prior Publication Data
US 2014/0335065 A1 Nov. 13, 2014

Related U.S. Application Data

(60) Provisional application No. 61/528,437, filed on Aug. 29, 2011.

(51) Int. Cl.
| | |
|---|---|
| A61K 31/702 | (2006.01) |
| A61K 35/74 | (2015.01) |
| A23L 33/28 | (2016.01) |
| A23L 33/21 | (2016.01) |
| A23L 33/00 | (2016.01) |
| A61K 35/741 | (2015.01) |
| A61K 35/744 | (2015.01) |
| A61K 35/745 | (2015.01) |
| A61K 35/747 | (2015.01) |
| A61K 35/00 | (2006.01) |

(52) U.S. Cl.
CPC ............ *A61K 31/702* (2013.01); *A23L 33/21* (2016.08); *A23L 33/28* (2016.08); *A23L 33/40* (2016.08); *A61K 35/741* (2013.01); *A61K 35/744* (2013.01); *A61K 35/745* (2013.01); *A61K 35/747* (2013.01); *A23V 2002/00* (2013.01); *A61K 2035/115* (2013.01)

(58) Field of Classification Search
USPC .............................................. 424/93; 514/54
See application file for complete search history.

(56) References Cited

U.S. PATENT DOCUMENTS

| | | |
|---|---|---|
| 4,762,822 A | 8/1988 | Ettinger |
| 5,013,569 A | 5/1991 | Rubin |
| 5,260,280 A | 11/1993 | Isoda et al. |
| 5,834,423 A | 11/1998 | Koketsu et al. |
| 5,906,982 A | 5/1999 | Prieto et al. |
| 6,036,992 A | 3/2000 | Borror et al. |
| 6,045,854 A * | 4/2000 | Prieto ...................... A23L 29/30 426/658 |
| 6,080,787 A | 6/2000 | Carlson et al. |
| 6,083,934 A | 7/2000 | Prieto et al. |
| 6,146,670 A | 11/2000 | Prieto et al. |
| 6,294,206 B1 | 9/2001 | Barrett-Reis |
| 6,306,908 B1 | 10/2001 | Carlson et al. |
| 6,365,218 B1 | 4/2002 | Borschel et al. |
| 6,497,908 B1 | 12/2002 | Oshiro |
| 6,576,251 B1 | 6/2003 | Stahl et al. |
| 6,630,452 B2 | 10/2003 | Wilson |
| 7,090,862 B2 | 8/2006 | Barrett-Reis et al. |
| 7,090,879 B2 | 8/2006 | Albrecht et al. |
| 7,101,565 B2 | 9/2006 | Monte |
| 7,416,752 B2 | 8/2008 | Holub et al. |
| 8,425,930 B2 * | 4/2013 | Barboza ................ A23L 33/125 424/439 |
| 8,703,737 B2 | 4/2014 | Buck et al. |
| 8,771,674 B2 | 7/2014 | Sprenger |
| 8,802,650 B2 | 8/2014 | Buck et al. |
| 8,815,312 B2 * | 8/2014 | Falk ...................... A23L 33/135 424/725 |
| 8,926,952 B2 | 1/2015 | Trejo et al. |
| 9,217,133 B2 | 12/2015 | Sprenger |

(Continued)

FOREIGN PATENT DOCUMENTS

| | | |
|---|---|---|
| CA | 2655665 | 12/2007 |
| CA | 2724766 | 3/2010 |

(Continued)

OTHER PUBLICATIONS

Barbara (Interactions Between Commensal Bacteria and Gut Sensorimotor Function in Health and Disease, 2005).*
Final Office Action in U.S. Appl. No. 13/334,933 dated Aug. 10, 2015.
Amendment with RCE in U.S. Appl. No. 13/334,933 dated Nov. 10, 2015.
Office Action for U.S. Appl. No. 13/334,933 dated Jan. 22, 2016.
Amendment with RCE in U.S. Appl. No. 13/335,341 dated Sep. 4, 2015.
Office Action for U.S. Appl. No. 13/335,341 dated Oct. 7, 2015.
Office Action in CA 2,846,603 dated Oct. 26, 2015.
Office Action in CA 2,842,672 dated Dec. 1, 2015.
English translation of Second Office Action in CN 201180067021.x dated Jun. 26, 2015.

(Continued)

*Primary Examiner* — Nghi V Nguyen
(74) *Attorney, Agent, or Firm* — Calfee, Halter & Griswold LLP

(57) ABSTRACT

Disclosed are nutritional compositions including human milk oligosaccharides that can be administered to individuals including preterm infants, infants, toddlers, children, and adults for preventing injury and/or improving the healing of the gastrointestinal tract. Additional suitable methods of using the nutritional compositions including the human milk oligosaccharides are also disclosed.

14 Claims, 8 Drawing Sheets

(56) References Cited

U.S. PATENT DOCUMENTS

| | | |
|---|---|---|
| 9,539,269 B2 | 1/2017 | Chow et al. |
| 2002/0019991 A1 | 2/2002 | Prieto et al. |
| 2003/0060445 A1 | 3/2003 | Wilson |
| 2004/0001817 A1 | 1/2004 | Giampapa |
| 2004/0202765 A1 | 10/2004 | McMahon et al. |
| 2004/0265462 A1 | 12/2004 | Carlson |
| 2005/0004070 A1 | 1/2005 | Stahl et al. |
| 2005/0070464 A1 | 3/2005 | Stahl et al. |
| 2005/0096295 A1 | 5/2005 | McMahon et al. |
| 2005/0208179 A1 | 9/2005 | Albrecht et al. |
| 2006/0039954 A1 | 2/2006 | Gierhart et al. |
| 2006/0088574 A1 | 4/2006 | Manning et al. |
| 2006/0246146 A1 | 11/2006 | McMahon et al. |
| 2006/0247153 A1 | 11/2006 | McMahon et al. |
| 2006/0270739 A1 | 11/2006 | Johnson et al. |
| 2007/0048405 A1 | 3/2007 | DeWille et al. |
| 2007/0058523 A1 | 5/2007 | Willemsen et al. |
| 2007/0098849 A1 | 5/2007 | Barrett-Reis et al. |
| 2007/0104700 A1 | 5/2007 | Garcia-Rodenas et al. |
| 2007/0104843 A1 | 5/2007 | Holst et al. |
| 2007/0173480 A1 | 7/2007 | Clandinin et al. |
| 2007/0255598 A1 | 11/2007 | McCarthy |
| 2008/0003329 A1 | 1/2008 | Rueda et al. |
| 2008/0003330 A1 | 1/2008 | Rueda et al. |
| 2008/0015166 A1 | 1/2008 | van Tol et al. |
| 2008/0057178 A1 | 3/2008 | Rueda et al. |
| 2008/0064635 A1 | 3/2008 | Rueda et al. |
| 2008/0089981 A1 | 4/2008 | Butler et al. |
| 2008/0125346 A1 | 5/2008 | Beermann et al. |
| 2009/0082249 A1 | 3/2009 | Garssent et al. |
| 2009/0092590 A1 | 4/2009 | Rangavajila et al. |
| 2009/0098240 A1 | 4/2009 | Mills et al. |
| 2009/0118229 A1 | 5/2009 | Zeina |
| 2009/0143301 A1 | 6/2009 | Olson et al. |
| 2009/0148545 A1 | 6/2009 | Falk et al. |
| 2009/0191151 A1 | 7/2009 | Gai et al. |
| 2009/0305996 A1 | 12/2009 | Beermann et al. |
| 2010/0047393 A1 | 2/2010 | Glas et al. |
| 2010/0063002 A1 | 3/2010 | Stahl et al. |
| 2010/0233129 A1 | 9/2010 | Fichot et al. |
| 2010/0233198 A1 | 9/2010 | Fichot et al. |
| 2010/0254949 A1 | 10/2010 | Barboza et al. |
| 2010/0260720 A1 | 10/2010 | Sprenger |
| 2010/0298244 A1 | 11/2010 | Yang et al. |
| 2010/0316619 A1 | 12/2010 | Wittke |
| 2012/0121561 A1 | 5/2012 | Mercenier et al. |
| 2012/0171166 A1 | 7/2012 | Chow |
| 2012/0172319 A1 | 7/2012 | Chow |
| 2012/0177691 A1 | 7/2012 | Stahl et al. |
| 2012/0294840 A1 | 11/2012 | Newburg et al. |
| 2013/0012472 A1 | 1/2013 | Newburg et al. |
| 2013/0059815 A1 | 3/2013 | Fournell et al. |
| 2014/0286908 A1 | 9/2014 | Garcia-Rodenas et al. |
| 2014/0294789 A1 | 10/2014 | David et al. |
| 2015/0079040 A1 | 3/2015 | O'Neill et al. |
| 2016/0113976 A1 | 4/2016 | Burcelin et al. |
| 2018/0078589 A1 | 3/2018 | Kyle et al. |
| 2018/0110253 A1 | 4/2018 | Sprenger et al. |
| 2018/0200312 A1 | 7/2018 | Snijders et al. |
| 2018/0220691 A1 | 8/2018 | Garcia-Rodenas et al. |
| 2019/0069586 A1 | 3/2019 | Kyle et al. |
| 2019/0134114 A1 | 5/2019 | Kusuda et al. |
| 2019/0201459 A1 | 7/2019 | Koshida et al. |
| 2019/0224254 A1 | 7/2019 | Kyle et al. |
| 2019/0240268 A1 | 8/2019 | Koshida et al. |

FOREIGN PATENT DOCUMENTS

| | | | |
|---|---|---|---|
| CA | 2818505 | 11/2010 | |
| CA | 2822660 | 7/2012 | |
| CN | 101909615 A | 12/2010 | |
| CN | 101909644 A | 12/2010 | |
| CN | 103797021 | 5/2014 | |
| EP | 1487469 | 12/2004 | |
| EP | 1549151 | 7/2005 | |
| EP | 1634599 | 3/2006 | |
| EP | 1887017 | 2/2008 | |
| EP | 2127661 | 2/2009 | |
| EP | 2060257 | 5/2009 | |
| EP | 2072052 | 6/2009 | |
| EP | 1999603 B1 | 7/2009 | |
| EP | 2266582 | 12/2010 | |
| EP | 2279672 | 2/2011 | |
| EP | 1609463 B1 | 5/2011 | |
| EP | 2429551 A1 | 3/2012 | |
| EP | 2455387 | 5/2012 | |
| EP | 2642876 A1 | 10/2013 | |
| EP | 2836223 A1 | 2/2015 | |
| EP | 2234627 B1 | 5/2016 | |
| EP | 2643004 B1 | 12/2016 | |
| EP | 2643005 B1 | 3/2017 | |
| EP | 2768311 B1 | 2/2018 | |
| EP | 3285785 A1 | 2/2018 | |
| EP | 3331383 A1 | 6/2018 | |
| EP | 3366299 A1 | 8/2018 | |
| EP | 3366300 A1 | 8/2018 | |
| EP | 3268019 A1 | 10/2018 | |
| EP | 3426270 A1 | 1/2019 | |
| EP | 3443969 A1 | 2/2019 | |
| EP | 3478082 A1 | 5/2019 | |
| EP | 3478093 A1 | 5/2019 | |
| EP | 2201955 B1 | 8/2019 | |
| EP | 3522894 A1 | 8/2019 | |
| EP | 3426269 A1 | 10/2019 | |
| JP | 8266255 | 10/1996 | |
| JP | 10099048 | 4/1998 | |
| JP | 10327804 | 12/1998 | |
| WO | 1997048388 | 12/1997 | |
| WO | 19980043494 | 10/1998 | |
| WO | 2001042263 | 6/2001 | |
| WO | 2001060346 | 8/2001 | |
| WO | 2003003981 | 1/2003 | |
| WO | 2003/082313 | 10/2003 | |
| WO | 2004032639 | 4/2004 | |
| WO | 2004052121 | 6/2004 | |
| WO | 2004112509 | 12/2004 | |
| WO | WO 2004112509 A2 * | 12/2004 | ........... A61K 31/202 |
| WO | 2005055944 | 6/2005 | |
| WO | 2005067962 | 7/2005 | |
| WO | 2005122790 | 12/2005 | |
| WO | 2007046699 | 4/2007 | |
| WO | 2007087468 | 8/2007 | |
| WO | 2007/101675 | 9/2007 | |
| WO | 2007101675 | 9/2007 | |
| WO | 2007108690 | 9/2007 | |
| WO | 2007114683 | 10/2007 | |
| WO | 2007114696 | 10/2007 | |
| WO | 2007136428 | 11/2007 | |
| WO | 2008016306 | 2/2008 | |
| WO | 2008033520 | 3/2008 | |
| WO | 2008056983 | 5/2008 | |
| WO | 2008108651 | 9/2008 | |
| WO | 2008127104 | 10/2008 | |
| WO | 2008139984 | 11/2008 | |
| WO | 2008153391 | 12/2008 | |
| WO | 2009033011 | 3/2009 | |
| WO | 2009059996 | 5/2009 | |
| WO | 2009067000 | 5/2009 | |
| WO | 2009077352 | 6/2009 | |
| WO | WO 2009077352 A1 * | 6/2009 | ........... A61K 31/702 |
| WO | 2009102193 | 8/2009 | |
| WO | 20090113861 | 9/2009 | |
| WO | 2010003803 | 1/2010 | |
| WO | 2010023178 | 3/2010 | |
| WO | 2010065652 | 6/2010 | |
| WO | 20100070104 | 6/2010 | |
| WO | 20100115934 | 10/2010 | |
| WO | 2010142504 | 12/2010 | |
| WO | 2011005681 | 1/2011 | |
| WO | 2011008087 | 1/2011 | |
| WO | 2011012655 | 2/2011 | |
| WO | 2011014468 | 2/2011 | |
| WO | 2011090926 | 7/2011 | |
| WO | 2011096809 | 8/2011 | |

(56) References Cited

FOREIGN PATENT DOCUMENTS

| WO | 2011136636 | 11/2011 |
|---|---|---|
| WO | 2011136647 | 11/2011 |
| WO | 2012009315 | 1/2012 |
| WO | 2012069415 | 5/2012 |
| WO | 2012/076323 | 6/2012 |
| WO | 2012076323 | 6/2012 |
| WO | 2012092153 | 7/2012 |
| WO | 2012092155 | 7/2012 |
| WO | 2012092156 | 7/2012 |
| WO | 2012092157 | 7/2012 |
| WO | 2012092158 | 7/2012 |
| WO | 2012092159 | 7/2012 |
| WO | 2012092160 | 7/2012 |
| WO | 2013016111 | 1/2013 |
| WO | 2013032674 | 7/2013 |
| WO | 2013185780 | 12/2013 |
| WO | 2004047778 | 6/2014 |
| WO | 2018106844 A1 | 6/2018 |
| WO | 2018112366 A1 | 6/2018 |
| WO | 2018169297 A1 | 9/2018 |
| WO | 2018190407 A1 | 10/2018 |
| WO | 2019055718 A1 | 3/2019 |

OTHER PUBLICATIONS

English translation of Notification of Grant of Patent in CN201180068703.2 dated Jul. 15, 2015.
English translation of Second Office Action in CN 201280051863.0 dated Nov. 4, 2015.
English summary of Office Action in MX/a/2013/007675 dated Oct. 30, 2015.
Search Report and Written Opinion in SG 201305083-6 dated Jul. 31, 2015.
English translation of Office Action in TW Application No. 100150004 dated Aug. 25, 2015.
Chen, L.R., "Introduction of Oligosaccharide," Department of Dietetics, MacKay Memorial Hospital, Oct. 2010, http://www.mmh.org.tw/nutrition/nutrroom/261oligo.htm.
Chou, J.J., "Microorganisms, Foods, Probiotics, and Bifidus," Food and Life, Dec. 2004, http://203.145.193.110/NSC_INDEX/Journal/EJ0001/9312/9312-02.pdf.
Oliveros et al., "Prebioticos en formulas infantiles," An Pediatr., Monograph 4(1) 20-29 (Apr. 2006).
Procter & Gamble "What is Bifantis?" About Bifantis, Nov. 4, 2010 https://web.archive.org/web/20101104124637/http://www.bifantis.com.
Non final rejection for U.S. Appl. No. 13/334,933 dated Jun. 27, 2014.
First Examination Report in NZ 611,807 dated Dec. 19, 2013.
International Search Report for PCT/US2011/043644 dated Feb. 17, 2012.
International Search Report and Written Opinion for PCT/US2011/067004 dated Jun. 11, 2012.
International Search Report and Written Opinion for PCT/US2011/067008 dated Mar. 29, 2012.
International Preliminary Report on Patentability for PCT/US2011/067012 dated Jul. 2, 2013.
International Search Report and Written Opinion for PCT/US2011/067012 dated May 24, 2012.
International Search Report and Written Opinion for PCT/US2011/067018 dated Mar. 27, 2012.
International Search Report and Written Opinion for PCT/US2011/067022 dated Jun. 11, 2012.
International Search Report and Written Opinion for PCT/US2011/067027 dated Jun. 11, 2012.
Invitation to Pay Additional Fees for PCT/US2011/067027 dated Mar. 27, 2012.
International Search Report and Written Opinion for PCT/US2011/067028 dated Mar. 27, 2012.
Invitation to Pay Additional Fees for PCT/2011/067031 dated May 29, 2012.
International Search Report and Written Opinion for PCT/US2012/047307 dated Nov. 14, 2012.
International Preliminary Report on Patentability for PCT/US2012/047307 dated Jan. 28, 2014.
International Search Report and Written Opinion for PCT/US2012/050569 dated Oct. 29, 2012.
International Preliminary Report on Patentability for PCT/US2012/050569 dated Mar. 4, 2014.
Rule 161/162 Communication for EP Application No. 11811618.5 dated Aug. 7, 2013.
Rule 161/162 Communication for EP Application No. 12741201.3 dated Feb. 28, 2014.
Rule 161/162 Communication for EP Application No. 12766344.1 dated Apr. 4, 2014.
First Examination Report in NZ 612,386 dated Dec. 18, 2013.
Office Action in VN Appl. No. 1-2013-01875 dated Oct. 21, 2013.
Second Office Action in VN Appl. No. 1-2013-01875 dated Jan. 8, 2014.
Abbott's Gain with Immunify Ingredients, available at http://www.abbott.com/sg/family/products/children/gain.asp last accessed Mar. 13, 2012.
Abbott's Similac with Immunify Ingredients, available at http://www.abbott.com.sg/family/products/children/similac_follow_on.asp, last accessed Mar. 13, 2012.
Aggett et al., "Nondigestible carbohydrates in the diets of infants and young children: a commentary by the ESPGHAN Committee on Nutrition," J. Pediatr. Gastroenterol. Nutr., vol. 36(3), pp. 329-337 (2003).
Albermann et al., "Synthesis of the milk oligosaccharide 2'-fucosyllactose using recombinant bacterial enzymes," Carbohydrate Research, vol. 334 (2), pp. 97-103 (2001).
Armogida, "Identification and quantification of innate immune system mediators in human breast milk," Allergy and Asthma Proceedings, vol. 25(5), pp. 297-304 (2004).
Arslanoglu et al., "Early dietary intervention with a mixture of prebiotic oligosaccharides reduces the incidence of allergic manifestations and infections during the first two years of life," J. Nutr., vol. 138(6), pp. 1091-1095 (2008).
Arslanoglu, et al., "Early supplementation of prebiotic oligosaccharides protects formula-fed infants against infections during the first 6 months of life," J. Nutr., vol. 137(11), pp. 2420-2424 (2007).
Asakuma et al., "Sial oligosaccharides of human colostrum: Changes in concentration during the first three days of lactation," Biosci. Biotechnol. Biochem., vol. 71(6), pp. 1447-1451 (2007).
Ashida, et al., "Two distinct alpha-L-fucosidases from Bifidobacterium bifidum are essential for the untilization of fucosylated milk oligosaccharides and glycoconjugates," Glybiology, vol. 19(9), pp. 1010-1017 (2009).
Bakker-Zierikzee et al., "Effects of infant formula containing a mixture of glacto- and fructo-oligosaccharides or viable Bifidobacterium animalis on the intestinal microflora during the first 4 months of life," Br. J. Nutr., vol. 94(5), pp. 783-790 (2005).
Bao, et al., "Simultaneous quantification of sialyloliogsaccharides from human milk by capillary electrophoresis," Anal. Biochem., vol. 370(2), pp. 206-214 (2007).
Barker, et al., "The colorimetric determination of lactic acid in biological materials," J. Bio. Chem., vol. 138, pp. 535-554 (1941).
Baarrangou et al., "Functional and comparative genomic analysis of an operon involved in fructooliogosaccharide utilization by Lactobacillus acidophilus," Proceedings of the National Academy of Sciences of the United States of America, vol. 100(15), pp. 8957-8962 (2003).
Barrat et al., "Supplementation with galactooliogosaccharides and inulin increases bacterial translocation in artificially reared newborn rats," Peditr. Res., vol. 64(1), pp. 34-39 (2008).
Bezokorovainy, A., "Probiotics: determination of survival growth in the gut," Am. J. Clin. Nutr., vol. 73 (2 Suppl.), pp. 399S-405S (2001).
Bode et al., "Human milk-oligosaccharides: prebiotics and beyond," Nutr. Rev., vol. 67, pp. S183-S191 (2009).

(56) References Cited

OTHER PUBLICATIONS

Bode et al., "Human milk-oligosaccharides reduce platelet-neutrophil complex formation leading to a decrease in neutrophil beta-2 integrin expression," J. Leukocyte Bio., vol. 76, pp. 820-826 (2004).
Dr. Bode presentation, "Human Milk Oligosaccharides, Only the Breast," T. Denny Sanford Pediatrict Symposia, Apr. 24-25, 2009.
Bode et al., "Inhibition of monocyte, lymphocyte and neutrophil adhesion to endothelial cells by human milk oligosaccharides," Thrombosis and Haemostasis, vol. 92(6), pp. 1402-1410 (2004).
Bode, L., "Recent advances on structure, metabolism, and function of human milk oligosaccharides," J. Nutr., vol. 136, pp. 2127-2130 (2006).
Boehm, et al., "Oligosaccharides from milk," J. Nutr., vol. 137(3 Suppl. 2), pp. 847S-849S (2007).
Boehm et al., "Prebiotic carbohydrates in human milk and formulas," Acta Paediatr. Suppl., vol. 94(449), pp. 18-21 (2005).
Boehm, et al., "Prebiotic concept for infant nutrition," Acta Paediatr. Suppl., vol. 91(441), pp. 64-67 (2003).
Boehm, et al., "Prebiotics in infant formulas," J. Clin. Gastroenterol., vol. 38(6 Suppl.), pp. S76-S79 (2004).
Boehm, et al., "Supplementation of a bovine mild formula with an oligosaccharide mixture increases counts of faecal bifidobacteria in preterm infants," Arch. Dis. Child Fetal Neonatal Ed., vol. 86(3), pp. F178-F181 (2002).
Bouhnik, et al., "Short-chain fructo-oligosaccharide administration dose-dependently increases fecal bificobacteria in healthy humans," J. Nutr., vol. 129, pp. 113-116 (1999).
Bourquin, et al., "Vegetable fiber fermentation by human fecal bacteria: cell wall polysaccharide disappearance and short-chain fatty acid production during in vitro fermentation and water-holding capacity of unfermented residues," J. Nutr., vol. 123, pp. 860-869 (1993).
Bruzzese et al., "A formula containing galacto- and fructo-oligosaccharides prevents intestinal and extra-intestinal infections: an observational study," Clin. Nutr., vol. 28(2), pp. 156-161 (2009).
Bryant, et al., "Cultural methods and some characteristics of some of the more numerous groups of bacteria in the bovine rumen," J. Dairy Sci., vol. 36, pp. 205-217 (1953).
Buck, "Effect of Dietary Ribonudleotides on Infant Immmune Status. Part 2: Immune Cell Development," Pediatric Research, vol. 56(6), pp. 891-900 (2004).
Campbell, et al., "Selected indigestible oligosaccharides affect large bowel mass, cecal and fecal short-chain fatty acids, pH and microflora in rats," J. Nutr., vol. 127(1), pp. 130-136 (1997).
Castro, et al., "Cutting Edge: IFN-y Regulates the Induction and Expansion of IL-17-Producing CD4 T Cells during Mycobacterial Infection," Journal of Immunology, vol. 177(3), pp. 1416-1420 (2006).
Chaturvedi, "Fucosylated human milk oligosaccharides vary between individuals and over the course of lactation," Glycobiology, vol. 11 pp. 365-372 (2001).
Chen, et al., "Probiotics and prebiotics: role in clinical disease states," Adv. Pediatr., vol. 52, pp. 77-113 (2005).
Chierici et al., "Advances in the modulation of the microbial ecology of the gut in early infancy," Acta Paediatr. Suppl., vol. 91(441), pp. 56-63 (2003).
Cherbut et al., "The Prebiotic Characterisitics of Fructooliogosaccharides Are Necessary for Reduction of TNBS-Induced Colitis in Rats," J. of Nutr., vol. 133, pp. 21-27 (2003).
Cinquin, et al., "Comparative effects of exopolysaccharides from lactic acid bacteria and fructo-oligosaccharides on infant gut microbiota tested in an in vitro colonic model with immobilized cells," FEMS Microbiol. Ecol., vol. 57(2), pp. 226-238 (2006).
Coppa et al., "Characterization of oligosaccharides in milk and feces of breast-fed infants by high-performance anion-exchange chromatography," Adv. Exp. Med. Biol., vol. 501, pp. 307-314 (2001).
Coppa et al., "The first prebiotics in humans: human milk oligosaccharides," J. Clin. Gastroenterol., vol. 38(Suppl.2), pp. S80-S83 (2004).
Cummings, et al., "Gastrointestinal effects of prebiotics," Br. J. Nutr., vol. 87(Suppl.2), pp. S145-S151 (2002).
Daddaoua, et al., "Goat Milk Oligosaccharides are Anti-Inflammatory in Rats with Hapten-Induced Colitis," Journal of Nutrition, vol. 136(3), pp. 672-676 (2006).
D'Souza et al., "Effects of Probiotics, Prebiotics, and Synbiotics on Messenger RNA Expression of Caveolin-1, NOS and Genes Regulating Oxidative Stress in the Terminal Illeum of Formula-Fed Neonatal Rats," Pediatric Research, vol. 67, pp. 526-531 (2010).
De la Fuente, et al., "Anti Oxidants as modulators of immune function," Immunology and Cell Biology, vol. 78, pp. 49-54 (2000).
De Vrese, et al., "Probiotics, prebiotics, and synbiotics," Adv. Biochem Eng. Biotechnol., vol. 111, pp. 1-66 (2008).
Douville, et al., "Human metapneumovirus elicits weak IFN-g memory responses compared with RSV," J. of Immun., vol. 176, pp. 5848-5855 (2006).
Edwards, et al., "Dietary fibre in infancy and childhood," Proc. Nutr. Soc., vol. 62(1), pp. 17-23 (2003).
Edwards et al., "Intestinal flora during the first months of life: new perspectives," Br. J. Nutr., vol. 88 (Suppl. 1), pp. S11-S18 (2002).
Eiwegger et al., "Human milk-derived oligosaccharides and plant-derived oligosaccharides stimulate cytokine production of cord blood t-cells in vitro," Pediatr. Res., vol. 56, pp. 536-540 (2004).
Eiwegger et al., "Prebiotic oligosaccharides: in vitro evidence for gastrointestinal epithelial transfer and immunomodulatory properties," Pediatric Allergy and Immunology, vol. 21(8), pp. 1179-1188 (2010).
Espinoza et al., "Efforts to emulate human milk oligosaccharides," Br. J. of Nutr., vol. 98 (Suppl. 1), pp. S74-S79 (2007).
Euler, et al., "Prebiotic effect on fructo-oligosaccharide supplemented term infant formula at two concentrations compared with unsupplemented formula and human milk," J. Pediatr. Gastroenterol. Nutr., vol. 40, pp. 157-164 (2005).
Fanaro et al., "Acidic oligosaccharides from pectin hydrolysate as new component for infant formulae: effect on intestinal flora, stool characteristics, and Ph," J. Pediatr. Gastroenterol. Nutr., vol. 41(2), pp. 186-190 (2005).
Fanaro et al., "Galacto-oligosaccharides and long-chain fructo-oligosaccharides as prebiotics in infant formulas: a review," Acta Paediatr. Suppl., vol. 94(449), pp. 22-26 (2005).
Fisberg et al., "Effect of Oral Nutritional Supplementation with or without Synbiotics on Sickness and Catch-up Growth in Preschool Children," Intern. Pediatr., vol. 17(4), pp. 216-222 (2002).
Flickinger et al., "In vitro fermentation properties of selected frutoologasaccharide-containing vegetables and in vivo colonic microbial populations are affected by the diets of healthy human infants," J. Nutr., vol. 132(8), pp. 2188-2194 (2002).
Forsythe et al., "Mood and gut feelings," Brain Behav. Immun., vol. 24(1), pp. 1-8 (2009).
Forsythe et al., "Oral treatment with live Lactobacillus reuteri inhibits the allergic airway response in mice," Am. J. Resp. Crit. Care Med., vol. 175(6), pp. 561-569 (2007).
Forsythe et al., "Probiotics in neurology and psychiatry," In Therapeutic Microbiology: Probiotics and Related Strategies, Versalovic, J., Wilson M. ed., Washington D.C., ASM Press, pp. 285-298 (2008).
Friel, et al., "Milk from Mothers of Both Premature and Full-Term Infants Provide Better Antioxidant Protection than Does Infant Formula," Ped. Res., vol. 51(5), pp. 612-618 (2002).
Friesland Foods Friso Gold Infant Formulas, available at http://www.friso.com.sg/products/frisogold2.php, last accessed Mar. 13, 2012.
German, et al., "Human milk oligosaccharides: evolution, structures and bioselectivity as substrates for intestinal bacteria," Nestle Nutr. Workshop Ser. Pediatr. Program, vol. 62, pp. 218-222 (2008).
Ghoddusi et al., "In vitro study on gas generation and prebiotic effects of some carbohydrates and their mixtures," Anaerobe, vol. 13, pp. 193-199 (2007).

(56) References Cited

OTHER PUBLICATIONS

Gibson, et al., "Dietary Modulation of the Human Colonic Microbiota: Introducing the Concept of Prebiotics," J. Nutr., vol. 125(6), pp. 1401-1412 (1995).
Gill et al., "Development and application of a liquid chromatographic method for analysis of nucleotides and nucleosides in milk and infant formulas," Intern. Dairy Journal, vol. 17(6), pp. 596-605 (2007).
Gill, et al., "Differential recruitment of dendritic cells and monocytes to respiratory mucosal sites in children with Influenze Virus or Respiratory Syncytial Virus Infection," Journal of Infectious Disease, vol. 198, pp. 1667-1676 (2008).
Gonzalez et al., "Differential transcriptional response of Bifidobacterium longum to human milk, formula milk, and galactooliogosaccharide," Appl. Environ. Microbiol., vol. 74(15), pp. 4686-4694 (2008).
Grabitske et al., "Gastrointestinal effects of low-digestible carbohydrates," Crit. Rev. Food Sci. Nutr., vol. 49(4), pp. 327-360 (2009).
Grazioso, et al., "Antiinflammatory Effects of Human Milk on Chemically Induced Colitis in Rats," Pediatric Research, vol. 42(5), pp. 639-643 (1997).
Grulee et al., "Breast and artificial feeding: influence of morbidity and mortality of twenty thousand infants," J. Am. Med. Assoc., vol. 103, pp. 735-738 (1934).
Gunnarsson et al., "Sialic acid residues play a pivotal role in alpha 1-acid glycoprotein (AGP)-induced generation of reactive oxygen species in chemotactic peptide pre-activated neutrophil granulocytes," Inflammation Research, vol. 59(2), pp. 89-95 (2010).
Gutierrez et al., "Immune response to nucleotide-supplemented infant formulae: systematic review and meta-analysis," British J. of Nutr., (2007), 98 (Suppl. 1), S64-S67 (2007).
Hernot et al., "In vitro fermentation profiles, gas production rates, and microbiota modulation as affected by certain fructans, galactooligosaccharides, and polydextrose," J. Agric. Food Chem., vol. 57, pp. 1354-1361 (2009).
Hidaka, et al., "Effects of fructooligosaccharides on intestinal flora and human health," Bifidobacteria Microflora, vol. 5(1), pp. 37-50 (1986).
"Human Breast Milk," Wikipedia, last accessed Feb. 2, 2012.
Idota, et al., "Growth-promoting effects of N-Acetylneuraminic acid-containing substances on bifidobacterial," Biosci. Biotech. Biochem., vol. 58, pp. 1720-1722 (1994).
Issacs, "Human milk inactivates pathogens individually, additively, and synergistically," J. Nutr., vol. 135(5), pp. 1286-1288 (2005).
Jantscher-Krenn et al., "Human milk oligosaccharides and their potential benefits for the breast-fed neonate," Minerva Pediatr., vol. 64, pp. 83-99 (2012).
Jyonouchi et al., "Dietary ribonucleotides increase antigen-specific type 1 T-helper cells in the regional draining lymph nodes in young BALB/cJ mice," Nutrition, vol. 19(1), pp. 41-46 (2003).
Kanamori, et al., "Experience of long-term synbiotic therapy in seven short bowel patients with refractory enterocolitis," J. of Pediatric Surgery, vol. 39 (11), pp. 1686-1692 (2004).
Karimi et al., "Lactobacillus reuteri induced regulatory T cells protect against an allergic airway response in mice," Am. J. Resp. Crit. Care Med., vol. 179(3), pp. 186-193 (2009).
Kashyap, et al., "Growth Nutrient Retention and Metabolic Response of Low-birth-weight Infants fed Supplemented and Unsupplemented Preterm Human Milk," American Journal of Clinical Nutrition, American Society for Nutrition, U.S., vol. 52(2), pp. 254-262, (1990).
Kasson, et al., "Structural basis for influence of viral glycans on ligand binding by influenze hemagglutinin," Biophysical Journal, vol. 95(7), pp. L48-L50 (2008).
Kauth, et al., "Synergistically upregulated IL-10 production in cocultures of monocytes and T cells after stimulation with RSV," International Archives of Allergy and Immunology, vol. 142, pp. 116-126 (2007).
Kay, et al., "Mechanisms of T lymphocyte activation," Immunology Letters, vol. 29, pp. 51-54 (1991).

Khachik et al., "Identification, Quantification, and Relative Concentrations of Carotenoids and their Metabolites in Human Milk and Serum," Analytical Chemistry, American Chemical Society, US, vol. 69(10), pp. 1873-1881 (1997).
Kien, C.L., "Digestion, absorption, and fermentation of carbohydrates in the newborn," Clin. Perinatol., vol. 23(2), pp. 211-228 (1996).
Kitaoka et al., "Novel putative galactose operon involving lacto-N-biose phosphorylase in Bifidobacterium longum," Appl. Environ. Microbiol., vol. 71(6), pp. 3158-3162 (2005).
Kiyohara, et al., "An exo-{alpha}-sialidase from bifidobacteria involved in the degradation of sialyloliogosaccharides in human milk and intestinal glycoconjugates," Glycobiology, vol. 21(4), pp. 437-447 (2011).
Kiyohara et al., "Prebiotic effect of lacto-N-biose 1 on bifidobacterial growth," Biosci. Biotechnol. Biochem., vol. 73(5), pp. 1175-1179 (2009).
Knol, et al., "Colon microflora in infants fed formula and galacto- and fructo-oligosaccharides: more like breast-fed infants," J. Pediatr. Gastroenterol. Nutr., vol. 40(1), pp. 36-42 (2005).
Kobata, A., "Structures and application of oligosaccharides in human milk," Proc. Jpn. Acad. Ser. B. Phys. Biol. Sci., vol. 86(7), pp. 731-747 (2010).
Kulkarni et al., "Influence of dietary nucleotide restriction on bacterial sepsis and phagocytic cell function in mice," Arch. Surg., vol. 121(2), pp. 169-172 (1986).
Kunz, C., "Komplexe Oligosaccharide in der Saeuglingsernaehrung," Monatsschrift Fuer Kinderheilkunde, Springer Verlag, DE, vol. 146(1), pp. 49-56 (1998).
Kunz et al., "Biological functions of oligosaccharides in human milk," Acta paediatr., vol. 82(11), pp. 903-912 (1993).
Kunz et al., "Oligosaccharides in human milk: structural, functional, and metabolic aspects," Annu. Rev. Nutr., vol. 20, pp. 699-722 (2000).
Kunz, et al., "Potential anti-inflammatory and anti-infectious effects of Human Milk Oligosaccharides," from Bioactive Components of Milk, Springer, pp. 455-465 (2008).
Kunze, et al., "Lactobacillus reuteri enhances excitability of colonic AH neurons by inhibiting calcium dependent potassium channel opening," J. Cell Mol. Med., vol. 13(8B), pp. 2261-2270 (2009).
Kuntz et al., "Oligosaccharides from human milk induce growth arrest via G2/M by influencing growth-related cell cycle genes in intestinal epithelial cells," Br. J. Nutr., vol. 101, pp. 1306-1315 (2009).
Kuntz, et al., "Oligosaccharides from human milk influence growth-related characteristics of intestinally transformed and non-transformed intestinal cells," Br. J. Nutr., vol. 99, pp. 462-471 (2008).
Kurokawa et al., "Comparative metagenomics revealed commonly enriched gene sets in human gut microbiomes," DNA Res., vol. 14, pp. 169-181 (2007).
Lara-Villoslada, "Oligosaccharides isolated from goat milk reduce intestinal inflammation in a rat model of dextran sodium sulfate-induced colitis," Clin. Nutr., vol. 25(3), pp. 477-488 (2006).
Leach et al., "Total potentially available nucleosides of human milk by stage of lactation," Am J. Clin. Nutr., vol. 61(6), pp. 1224-1230 (1995).
Lee et al., "Genomic insights into bifidobacteria," Microbiol. Mol. Biol. Rev., vol. 74(3), pp. 378-416 (2010).
Leyer, et al., "Probiotic Effects on Cold and Influenza-Like Symptom Incidence and Duration in Children," Pediatrics, vol. 124(2), pp. e172-e179 (2009).
Lin et al., "Necrotizing Enterocolitis: Recent Scientific Advances in Pathophysiology and Prevention," Seminars in Perinatology, WB Saunders, GB, vol. 32(2), pp. 70-82 (Mar. 14, 2008).
LoCascio, et al., "A versatile and scalable strategy for glycoprofiling bifidobacterial consumption of human milk oligosaccharides," Microb. Biotechnol., vol. 2, pp. 333-342 (2009).
LoCascio et al., "Broad conservation of milk utilization genes in *Bifidobacterium longum* subsp. *infantix* as revealed by comparative genomic hybridization," Appl. Environ. Microbiol., vol. 76(22), pp. 7373-7381 (2010).

(56) References Cited

OTHER PUBLICATIONS

LoCascio et al., "Glycoprofiling of bifidobacterial consumption of human milk oligosaccharides demonstrates strain specific, preferential consumption of small chain glycans secreted in early human lactation," J. Agric. Food Chem., vol. 55(22), pp. 8914-8919 (2007).

Ma et al., "Live Lactobacillus reuteri is essential for the inhibitory effect of tumour necrosis factor alpha-induced interleukin-8 expression," Infect. Immun., vol. 72, pp. 5308-5314 (2004).

Maaheimo, "Synthesis of a divalent sialyl Lewis X-O-glycan, a potent inhibitor of lymphocyte-endothelium adhesion. Evidence that multvalency enhances the saccharide binding to selectins," European Journal of Biochemistry, vol. 234, pp. 616-625 (1995).

Macfarlane et al., "Bacterial metabolism and health-related effects of galcto-oligosaccharides and other prebiotics," J. Appl. Microbiol., vol. 104(2), pp. 305-344 (2008).

MacIver, et al., "Glucose metabolism in lymphocytes is a regulated process with significant effects on immune cell function and survival," J. Leukoc. Biol., vol. 84, pp. 949-957 (2008).

Magne et al., "Effects on faecal microbiota of dietary and acidic oligosaccharides in children during partial formula feeding," J. Pediatr. Gastroenterol. Nutr., vol. 46(5), pp. 580-588 (2008).

Malhotra, et al., "Isolation and characterisation of potential respiratory syncytial virus receptor(s) on epithelial cells," Microbes and Infection, vol. 5, pp. 123-133 (2003).

Marcobal, et al, "Consumption of human milk oligosaccharides by gut-related microbes," J. Agric. Food Chem., vol. 58, pp. 5334-5340 (2010).

Mariat, "The Firmicutes/Bacteroidetes ratio of the human microbiota changes with age," BMC Microbiol., vol. 9, p. 123 (2009).

Marlett et al., "American Dietetic Association, Position of the American Dietetic Association: health implications of dietary fiber," J. Am. Diet. Assoc., vol. 102(7), pp. 993-1000 (2002).

Martin-Sosa, et al., "Sialyloligosaccharides in human and bovine milk and in infant formulas: variations with the progression of lactation," J. Dairy Sci., vol. 86, pp. 52-59 (2003).

Martinez-Ferez, et al., "Goats' milk as a natural source of lactose-derived oligosaccharides: Isolation by membrane technology," Intern. Dairy J., vol. 16(2), pp. 173-181 (2006).

Masuko, et al., "Carbohydrate analysis by a phenol-sulfuric acid method in microplate format," Anal. Biochem., vol. 339, pp. 69-72 (2005).

McKeller et al., "Metabolism of fructo-oligosaccharides by *Bifidobacterium* spp.," Appl. Microbiol. Biotechnol., vol. 31, pp. 537-541 (1989).

McVeagh, et al., "Human milk oligosaccharides: only the breast," J. Paediatr. Child Health, vol. 33(4), pp. 281-286 (1997).

Meinzen-Derr, "Role of human milk in extremely low birth weight infants' risk of necrotizing enterocolitis or death," J. Perinatology, vol. 29, pp. 57-62 (2009).

Michalek, et al., "Cutting Edge: Distinct Glycolytic and Lipid Oxidative Metabolic Programs are Essential for Effector and Regulatory CD4+T Cell Subsets," Journal of Immunology, vol. 186, pp. 3299-3303 (2011).

Miniello et al., "Prebiotics in infant milk formulas: new perspectives," Acta Paediatr. Suppl., vol. 91(441), pp. 68-76 (2003).

Miwa, et al., "Cooperation of beta-galactosidase and beta-N-acetylhexosaminidase from bifidobacteria in assimilation of human milk oligosaccharides with type 2 structure," Glycobiology, vol. 20(11), pp. 1402-1409 (2010).

Monaco et al., "The addition of polydextrose and galactooliogssacharide to formula does not affect barrier function or bacterial translocation in neonatal piglets," FASEB Journal, Meeting Abstract Supplement, vol. 23: LB479 (2009).

Moro et al., "Dosage-related bifidogenic effects of galacto- and fructooligosaccharides in formula-fed term infants," J. Pediatr. Gastroenterol. Nutr., vol. 34(3), pp. 291-295 (2002).

Moro et al., "Effects of a new mixture of prebiotics on faecal flora and stools in term infants," Acta Paediatr. Suppl., vol. 91(441), pp. 77-79 (2003).

Moro, et al., "Reproducing the bifidogenic effect of human milk in formula-fed infants: shy and how?", Acta Paediatr. Suppl., vol. 94(449), pp. 14-17 (2005).

Morrow et al., "Human milk oligosaccharides are associated with protection against diarrhea in breast-fed infants," J. Pediatr., pp. 297-303 (2004).

Morrow et al., "Novel salivary and genetic biomarkers of risk for NEC or death in premature infants," FASEB, vol. 23 (Meeting Abstract Supplement), LB270 (2009).

Morrow et al., "Secretor phenotype and genotype are novel predictors of severe outcomes in premature infants," FASEB, vol. 24 (Meeting Abstract Supplement), p. 480.6 (2010).

Mountzouris et al., "Intestinal microflora of human infants and current trends for its nutritional modulation," Br. J. Nutr., vol. 87(5), pp. 405-420 (2002).

Mshvildadze et al., "Probiotics and prevention of necrotizing enterocolitis," Early Human Development, Shannon, IR, vol. 85(10), pp. S71-S74 (Oct. 1, 2009).

Nakhla et al., "Neutral oligosaccharide content of preterm human milk," Br. J. Nutr., vol. 82, pp. 361-367 (1999).

Nakamura et al., "Concentrations of sialyloligosaccharides in bovine colostrum and milk during the prepartum and early lactation," J. Dairy Sci., vol. 86, pp. 1315-1320 (2003).

Nakamura et al., "Molecular ecological analysis of fecal bacterial populations from term infants fed formula supplemented with selected blends of prebiotics," Appl. Environ. Microbiol., vol. 75, pp. 1121-1128 (2009).

Nakano et al., "Sialic acid in human milk," Acta paediatrica taiwanica, vol. 42(1), pp. 11-17 (2001).

Navarro, et al., "Influence of Dietary Nucleotides on Plasma Immunoglobulin Levels and Lymphocyte Subsets of Preterm Infants," Biofactors, vol. 10(1), pp. 67-76 (1999).

Newburg, DS, "Neonatal protection by an innate immune system of human milk consisting of oligosaccharides and glycans," J. Anim. Sci., vol. 87 (13 Suppl.), pp. 26-34 (2009).

Newburg, et al., "Human milk glycans protect infants against enteric pathogens," Annu. Rev. Nutr., vol. 25, pp. 37-58 (2005).

Newburg, et al., "Innate protection conferred by fucosylated oligosaccharides of human milk against diarrhea in breastfed infants," Glycobiology, vol. 14(3), pp. 253-263 (2004).

Newburg, et al., "Oligosaccharides in human milk and bacterial colonization," J. Pediatr. Gasterenterol. Nutr., vol. 30, pp. S8-S17 (2000).

Newburg, et al., "Protection of the neonate by the innate immune system of developing gut and of human milk," Ped. Res., vol. 61(1), pp. 2-8 (2007).

Nicholls et al., "Evolving complexities of influenza virus and its receptors," Trends in Microbiology, vol. 16(4), pp. 149-157 (2008).

Ninonuevo et al., "A strategy for annotating the human milk glycome," J. Agric. Food Chem., vol. 54, pp. 7471-7480 (2006).

Ninonuevo et al., "Mass spectrometric methods for analysis of oligosaccharides in human milk," Nutr. Rev., vol. 67 (Suppl. 2), pp. S216-S226 (2009).

Palmer et al., "Development of the human infant intestinal microbiota," Plos Biol., vol. 5, p.e. 177, pp. 1556-1573 (2007).

Parrett, et al., "In vitro fermentation of carbohydrate by breast fed and formula fed infants," Arch. Dis. Childhood, vol. 76, pp. 249-253 (1997).

Petschow et al., "Response of *Bifidobacterium* species to growth promoters in human and cow milk," Pediatr. Res., vol. 29(2), pp. 208-213 (1991).

Pickering et al., "Modulation of the Immune System by Human Milk and Infant Formula Containing Nucleotides," Pediatrics, vol. 101(2), pp. 101(2), pp. 242-249 (1998).

Portelli, et al., "Effect of compounds with antibacterial activities in human milk on respiratory syncytial virus and cytomegalovirus in vitro," J. Med. Microbiol., vol. 47, pp. 1015-1018 (1998).

Probert et al., "Polydextrose, lactitol, and fructo-oligosaccharide fermentation by colonic bacteria in a three-stage continuous culture system," Appl. Environ. Microbiol., vol. 70(8), pp. 4505-4511 (2004).

Rinne, et al., "Similar bifidogenic effects of prebiotic-supplemented partially hydrolyzed infant formula and breastfeeding on infant gut

(56) References Cited

OTHER PUBLICATIONS microflora," Fems Immunology and Medical Microbiology, Elsevier Science BV, Amsterdam, NL, vol. 43(1), pp. 59-65 (2005).
Rivero-Urgell et al., "Oligosaccharides: application in infant food," Early Human Dev., vol. 65(Suppl.), pp. S43-S52 (2001).
Robertfroid, M., "Prebiotics: the concepts revisited," J. Nutr., vol. 137, pp. 830S-837S (2007).
Rueda et al., "Influence of dietary compounds on intestinal immunity," Microbiol. Ecol. Health Diseases, vol. 2, pp. 146S-156S (2000).
Rumessen, JJ., "Fructose and related food carbohydrates. Sources, intake, absorption, and clinical implications," Scand. J. Gastroenterol., vol. 27(10), pp. 819-828 (1992).
Russ et al., "Post-weaning effects of milk and milk components on the intestinal mucosa in inflammation," Mutation Research, Elsevier, Amsterdam, vol. 690, nos. 1-2, Aug. 7, 2010, pp. 64-70.
Rycroft et al., "A comparative in vitro evaluation of the fermentation properties of prebiotic oligosaccharides," J. Appl. Microbiol., vol. 91, pp. 878-887 (2001).
Saedisomeolia et al., "Lycopene enrichment of cultured epithelial cells decreases the inflammation induced by rhinovirus infection and lipopolysaccharide," J. Nutritional Biochemistry, vol. 20, pp. 577-585 (2009).
Salminenen et al., "Microbial-host interactions: selecting the right probiotics and prebiotics for infants," Nestle Nutr. Workshop Ser. Pediatr. Program, vol. 64, pp. 201-213 (2009).
Sangwan, et al., "Galactooliogosaccharides: novel components of designer foods," J. of Food Science, vol. 76(4), pp. R103-R111 (May 2011).
Schaefer et al., "Ammonia saturation constants for predominant species of rumen bacteria." J. Dairy Sci., vol. 63(8), pp. 1248-1263 (1980).
Schaller et al., "Effect of Dietary Ribonucleotides on Infant Immune Status. Part 1: Humoral Responses," Pediatric Research, vol. 56(6), pp. 883-890 (2004).
Schnabel, et al., "Gangliosides protect bowel in an infant model of necrotizing enterocolitis by suppressing proinflammatory signals," J. Pediatr. Gastroenter. Nutr., vol. 49, pp. 382-392 (2009).
Scholtens et al., "Bifodogenic effects of solid weaning foods with added prebiotic oligosaccharides: a randomised controlled clinical trial," J. Pediatr. Gatroenterol. Nutr., vol. 42(5), pp. 552-559 (2006).
Schrezenmeir et al., "Benefits of oral supplementation with and without synbiotics in young children with acute bacterial infections," Clin. Pediatr., vol. 43(3), pp. 239-249 (2004).
Sela et al., "The genome sequence of *Bifidobacterium longum* subsp. *infantis* reveals adaptations for milk utilization within the infant microbiome," Proc. Natl. Acad. Sci., USA, vol. 105(48), pp. 18964-18969 (2008).
Sela et al., "Nursing our microbiota: molecular linkages between bifidobacteria and milk oligosaccharides," Trends Microb., vol. 18(7), pp. 298-307 (2010).
Sherman et al., "Potential roles and clinical utitlity of prebiotics in newborns, infants, and children," Proceedings from a global prebiotic summit meeting, New York City, Jun. 27-28, 2008, J. Pediatr., vol. 155(5), pp. S61-S70 (2009).
Soitgiu et al., "Immunomodulation of fucosyl-lactose and lacto-N-fucopentaose on mononuclear cells from multiple sclerosis and healthy subjects," Inter. J. Biomediacl. Sci., vol. 2(2), pp. 114-120 (2006).
Soukup et al., "Role of monocytes and eosinophils in human RSV infection in vitro," Clinical Immunology, vol. 107, pp. 178-185 (2003).
Spurrell, et al., "Human airway epithelial cells produce IP-10 (CXCL 10) in vitro and in vivo upon rhinovirus infection," Am. J. Physiol. Lung Cell Mol. Physiol., vol. 289, pp. L85-L95 (2005).
Stevens, et al., "Glycan microarray analysis of the hemagglutinins from modern and pandemic influenza viruses reveals different receptor specificities," Journal of Molecular Biology, vol. 355, pp. 1143-1155 (2006).

Stevens et al., "Structure and receptor specificity of the Hemagglutinin from an H5N1 influenza virus," Science, vol. 312, pp. 404-410 (2006).
Stewart, et al., "Fructooliogosaccharides exhibit more rapid fermentation than long-chain inulin in an in vitro fermentation system," Nutr. Res., vol. 28, pp. 329-334 (2008).
Sun, X., "Recent anti-influenza strategies in multivalent sialyloigosaccharides and sialylmimetics approaches," Current Medicinal Chemistry, vol. 14, pp. 2304-2313 (2007).
Suzuki et al., "Receptor specificities of human respiroviruses," J. of Virol., vol. 75(10), pp. 4604-4613 (2001).
Szylit, et al., "Physiological and pathphysiological effects of carbohydrate fermentation," World Rev. Nutr. Diet., vol. 74, pp. 88-122 (1993).
Teneberg, et al., "Inhibition of nonopsonic Helicobacter pylori-induced activation of human neutrophils by sialylated oligosaccharides," Glycobiology, vol. 10(11), pp. 1171-1181 (2000).
Thurl, et al., "Variation of human milk oligosaccharides in relation to milk groups and lactational periods," Br. J. of Nutr., vol. 104(9), pp. 1261-1271 (2010).
Thurl, et al., "Variation of netural oligosaccharides and lactose in human milk during the feeding," Zeitschrift fuer Ernaehrungswissenschaft, Steinkopf Verlag, Darmstadt, DE, vol. 32 (41), pp. 262-269 (1993).
Thymann et al., "Formula-feeding reduces lactose digestive capacity in neonatal pigs," British J. of Nutrition, vol. 95, pp. 1075-1081 (2006).
Tijerina-Saenz, "Antioxidant capacity of human milk and its association with vitamins A and E and fatty acid composition," Acta Paediatrica, vol. 98(11), pp. 1793-1798 (2009).
Tsopmo et al., "Human Milk has Anti-Oxidant Properties to Protect Premature Infants," Current Pediatric Reviews, vol. 3, pp. 45-51 (2007).
Vandenplas, Y., "Oligosaccharides in infant formula," Br. J. Nutr., vol. 87 (Suppl. 2), pp. S293-S296 (2002).
Varki, et al., "Biological roles of oligosaccharides: all of the theories are correct," Glycobiology, vol. 3(2), pp. 97-130 (1993).
Veereman, G., "Pediatric applications of inulin and oligofructose," J. Nutr., vol. 137(11 Suppl.), pp. 2585S-2589S (2007).
Veereman-Wauters, G., "Application of prebiotics in infant foods," Br. J. Nutr., vol. 93 (Suppl. 1), pp. S57-S60 (2005).
Vester Boler et al., "Carbohydrates blended with polydextrose lower gas production and short-chain fatty acid production in an in vitro system," Nutr. Res., vol. 29, pp. 631-639 (2009).
Videla et al., "Dietary inulin improves distal colitis induced by dextran sodium sulfate in the ratInulin in Dextran Sodium Sulfate Colitis," Am. J. of Gastro., vol. 96, pp. 1486-1493 (2001).
Von Nicolai et al., "Partial purification and properties of neuraminidase from Bifidobacterium lactentis," Hoppe Seylers Z Physiol. Chem., vol. 362(2), pp. 153-162 (1981).
Vos et al., "Dietary supplementation of neutral and acidic oligosaccharides enhances Th 1-dependent vaccination responses in mice," Pediatr. Allergy Immunol., vol. 18(4), pp. 304-312, (2007).
Vos et al., "Immune-modulatory effects and potential working mechanisms of orally applied nondigestible carbohydrates," Critical Reviews in Immunology, vol. 27(2), pp. 97-140 (Jan. 2007).
Wada et al., "Bifidobacterium bifidum lacto-N-biosidase, a critical enzyme for the degradation of human milk oligosaccharides with a type 1 structure," Appl. Environ. Microbiol., vol. 74(13), pp. 3996-4004 (2008).
Walker, A., "Milk and two oligosaccharides," Nat. Rev. Microbiol., vol. 7(7), p. 483 (2009).
Wang et al., "Effects of the in vitro fermentation of oligofructose and inulin by bacteria growing in the human large intestine," J. Appl. Bacteriol., vol. 75, pp. 373-380 (1993).
Wang, et al., "The role and potential of sialic acid in human nutrition," European Journal of Clinical Nutrition, vol. 57 (11), pp. 1351-1369 (2003).
Ward, Robert E. et al., "In vitro fermentability of human milk oligosaccharides by several strains of bifidobacteria," Molecular Nutrition & Food Research, vol. 51 (11), Nov. 2007, pp. 1398-1405.

(56) References Cited

OTHER PUBLICATIONS

Ward et al., "In vitro fermentation of breast milk oliogsaccharides by Bifidobacterium infantis and Lactobacillus gasseri," Appl. Environ. Microbiol., vol. 72, pp. 4497-4499 (2006).
Westerbeek et al., "Design of a randomised controlled trial on immune effects of acidic and neutral oligosaccharides in the nutrition of preterm infants: carrot study," BMC Pediatr., vol. 23, pp. 8-46 (2008).
Westerbeek et al., "The effect of enteral supplementation of a prebiotic mixture of non-human milk galacto-, fructo-, and acidic oligosaccharides on intestinal permeability in preterm infants," Br. J. Nutr., vol. 105, pp. 268-274 (2011).
Wilson, M., "The gastrointestinal tract and its indigenous microbiota," Microbial Inhabitants of Humans: their ecology and role in health and disease, Cambridge University Press, pp. 283-287 (2005).
Wong, et al., "Colonic health: fermentation and short chain fatty acids," J. Clin. Gastroenterol., vol. 40(3), pp. 235-243 (2006).
Wu, et al., "Development of an Annotated Library of Neutral Human Milk Oligosaccharides," J. Proteome Res., vol. 9, pp. 4138-4151 (2010).
Xiao et al., "Distribution of in vitro fermentation ability of lacto-N-biose 1, a major building block of human milk oligosaccharides, in bifidobacterial strains," Appl. Environ. Microbiol., vol. 76(1), pp. 54-59 (2010).
Yamada, et al., "Lactotriaose-containing carbosilane dendrimers: Synthesis and lectin-binding activities," Bioorganic & Medicinal Chemistry, vol. 15(4), pp. 1606-1614 (2007).
Yamazaki et al., "Measurement of growth of bifidobacteria on inulofructosaccharides," Let. Appl. Microbiol., vol. 10, pp. 229-232 (1990).
Yau, et al., "Effect of nucleotides on diarrhea and immune responses in healthy term infants in Taiwan,", J. Pediatr. Gastro. Nutr., vol. 36(1), pp. 37-43 (2003).
Yoshida et al., "Role of N-3 polyunsaturated fatty acids and sialic acid in learning performance of rats,", J. of Neurochemistry, vol. 65(Suppl.), p. S173 (1995).
Yu, et al., "Improved extraction of PCT-quality community DNA from digesta and fecal samples," BioTechniques, vol. 36, pp. 808-812 (2004).
Yuhas et al., "Human milk fatty acid composition from nine countries varies most in DHA," Lipids, vol. 41(9), pp. 851-858 (2006).
Ziegler, et al., "Term infants fed formula supplemented with selected blends of prebiotics grow normally and have soft stools similar to those reported for breast-fed infants," J. Pediatr. Gastroenterol. Nutr., vol. 44, pp. 359-364 (2007).
Zivkovic et al., "Microbes and health sackler colloquium: Human mild glycobiome and its impact on the infant gastrointestinal microbiota," Proc. Natl. Acad. Sci., USA (2010).
Amendment for U.S. Appl. No. 13/334,933 dated Jun. 23, 2015.
Final Office Action in U.S. Appl. No. 13/335,341 dated May 4, 2015.
First Office Action in CN 201280051863.0 dated Mar. 27, 2015.
Search Report and Written Opinion in SG 2013050067 dated May 28, 2015.
Search Report and Written Opinion in SG 201305083-6 dated Dec. 2, 2014.
Search Report and Written Opinion in SG 2014013478 dated Apr. 6, 2015.
Office Action and Search Report in TW Application No. 100149846 dated Apr. 21, 2015.
Office Action in VN 1-2013-02056 dated May 25, 2015.
Whorwell, et al., "Efficacy of an Encapsulated Probiotic Bifidobacterium infantis 35624 in Women with Irritable Bowel Syndrome," Am. J. of Gastroenterology, vol. 101, pp. 1581-1590 (2006).
Amendment for U.S. Appl. No. 13/334,933 dated Sep. 29, 2014.
Office Action for U.S. Appl. No. 13/334,933 dated Oct. 27, 2014.
Response with RCE for U.S. Appl. No. 13/334,933 dated Jan. 27, 2015.

First Office Action in CN 201180067021.x (PCT/US2011/067018) dated Aug. 15, 2014.
First Office Action in CN 201180068703.2 dated Nov. 4, 2014.
Office Action in EP Application No. 11811266.3 dated Aug. 18, 2014.
First Examination Report in NZ 620,311 dated Nov. 3, 2014.
First Examination Report in NZ 621,603 dated Nov. 28, 2014.
Written Opinion in SG 2013050067 dated Aug. 12, 2014.
Asakuma et al., "Variation of major neutral oligosaccharides levels in human colostrum", European Journal of Clinical Nutrition, vol. 62, pp. 488-494 Mar. 21, 2007.
Bode et al., "Human milk oligosaccharides prevent Nectrotizing Enterocolitis in neonatal rats," The FASEB Journal, vol. 24, p. 206.3 Apr. 2010.
Sumiyoshu W. et al., "Determination of each neutral oligosaccharide in the milk of Japanese women during the course of lactation," Br. J. Nutr. vol. 89, pp. 61-69 Mar. 9, 2003.
Urashima, Tadasu et al., "Biological significance of human milk oligosaccharides," Milk Science, vol. 56(4), pp. 155-176 (2008).
Office Action for U.S. Appl. No. 13/335,341 dated Nov. 5, 2014.
Procter & Gamble BIFANTIS news release dated May 12, 2009 (4 pages).
Response in U.S. Appl. No. 13/335,341 dated Feb. 3, 2015.
Office Action in CA 2,846,603 dated Feb. 3, 2015.
Third Party Observations from EP Application No. 12766344.1 dated Jan. 5, 2015.
Office Action for EP Application No. 12766344.1 dated Jan. 27, 2015.
Office Action for EP Application No. 12741201.3 dated Jan. 12, 2015.
Office Action for U.S. Appl. No. 13/334,933 dated Mar. 23, 2015.
Office Action in CA 2,842,672 dated Feb. 23, 2015.
First Office Action in CN 201180046188.2 dated Feb. 17, 2015.
Search Report and Written Opinion in SG 201400490.7 dated Mar. 16, 2015.
Amendment for U.S. Appl. No. 13/335,341 dated Nov. 1, 2016.
Office Action for U.S. Appl. No. 13/335,341 dated Feb. 16, 2017.
Amendment for U.S. Appl. No. 13/335,341 dated Jun. 16, 2017.
Office Action for U.S. Appl. No. 13/335,341 dated Oct. 3, 2017.
Office Action for U.S. Appl. No. 14/234,166 dated Jan. 6, 2017.
Amendment for U.S. Appl. No. 14/234,166 dated Apr. 6, 2017.
Office Action for U.S. Appl. No. 14/234,166 dated Sep. 8, 2017.
Office Action in CA 2,846,603 dated Feb. 8, 2017.
Office Action in CA 2,842,672 dated Oct. 24, 2016.
Office Action in CA 2,822,660 dated Oct. 4, 2017.
Notice of Reexamination in CN 201280046188.2 dated Mar. 13, 2017.
Fourth Office Action in CN 201280051863.0 dated Dec. 15, 2016.
Fifth Office Action in CN 201280051863.0 dated Jul. 4, 2017.
Exam Report Stage II for ID Application No. P00201400846 dated Feb. 24, 2017.
Exam Report Stage II for ID Application No. P00201401703 dated Mar. 9, 2017.
Exam Report for ID Application No. W00201302959 dated Jun. 8, 2017.
Third Office Action in MX/a/2013/007675 dated Mar. 7, 2017.
Fourth Office Action in MX/a/2013/007675 dated Jul. 27, 2017.
Office Action in MX/a/2014/000895 dated Mar. 7, 2017.
Substantive Examination Adverse Report in MY Application No. PI2013002504 dated Jan. 31, 2017.
Substantive Examination Adverse Report in MY Application No. PI2013002514 dated Jan. 31, 2017.
Substantive Examination Adverse Report in MY Application No. PI2014000552 dated May 15, 2017.
Substantive Examination Report in PH 1/2013/501382 dated Mar. 10, 2017.
Written Opinion in SG 2014004907 dated Nov. 3, 2016.
Written Opinion in SG 2014004907 dated May 29, 2017.
Office Action and Search Report in TW Application No. 101126368 dated May 4, 2016.
Decision on Rejection in TW Application No. 101126368 dated Dec. 28, 2016.
Amendment from U.S. Appl. No. 14/234,166 dated Jan. 8, 2018.

(56) References Cited

OTHER PUBLICATIONS

Office Action in CA 2,842,672 dated May 29, 2017.
Office Action in CA 2,822,219 dated Dec. 18, 2017.
Office Action from Israeli Application No. 230892 dated Jan. 4, 2018.
Office Action in MX/a/2014/002491 dated Nov. 21, 2017.
Exam Report in SG 2014004907 dated Nov. 12, 2017.
Office Action for U.S. Appl. No. 13/335,341 dated Jun. 26, 2018.
Amendment for U.S. Appl. No. 13/335,341 dated Sep. 26, 2018.
Advisory Action for U.S. Appl. No. 13/335,341 dated Oct. 30, 2018.
Amendment for U.S. Appl. No. 13/335,341 dated Nov. 26, 2018.
Response to Office Action for U.S. Appl. No. 14/234,166 dated Jun. 4, 2018.
Office Action for U.S. Appl. No. 14/234,166 dated Nov. 30, 2018.
Amendment for U.S. Appl. No. 15/401,488 dated Aug. 8, 2018.
Office Action for U.S. Appl. No. 15/401,488 dated Nov. 13, 2018.
Non final office action for U.S. Appl. No. 13/334,904 dated Jun. 27, 2014.
Amendment in U.S. Appl. No. 13/334,904 dated Sep. 29, 2014.
Final Office Action for U.S. Appl. No. 13/334,904 dated Nov. 18, 2014.
Response with RCE for U.S. Appl. No. 13/334,904 dated Feb. 18, 2015.
Office Action in U.S. Appl. No. 13/334,904 dated Mar. 20, 2015.
Response with RCE for U.S. Appl. No. 13/334,904 dated Jun. 22, 2015.
Final Office Action for U.S. Appl. No. 13/334,904 dated Jul. 24, 2015.
Remarks for Pre-Appeal Review for U.S. Appl. No. 13/334,904 dated Oct. 23, 2015.
Notice of Panel Decision from Pre-Appeal Brief Review in U.S. Appl. No. 13/334,904 dated Nov. 23, 2015.
Office Action in U.S. Appl. No. 13/334,904 dated Dec. 10, 2015.
Amendment in U.S. Appl. No. 13/334,904 dated Jun. 10, 2016.
Final Office Action in U.S. Appl. No. 13/334,904 dated Jul. 11, 2016.
Non-Final Office Action in U.S. Appl. No. 13/334,904 dated Jan. 25, 2017.
Office Action for U.S. Appl. No. 15/791,052 dated Dec. 6, 2018.
Office Action from Canadian Patent Application No. 2,822,497 dated Dec. 11, 2017.
Office Action in CA 2,842,672 dated Aug. 3, 2018.
Office Action in CA 2,822,219 dated Aug. 7, 2018.
First Office Action for CN Application No. 201180068712.1 dated Sep. 15, 2014.
Second Office Action for CN Application No. 201180068712.1 dated May 29, 2015.
English translation of Third Office Action for CN Application No. 201180068712.1 dated Dec. 8, 2015.
English translation of Fourth Office Action for CN Application No. 201180068712.1 dated Jun. 27, 2016.
Fifth Office Action for CN Application No. 201180068712.1 dated Apr. 1, 2017.
Office Action from Chinese Application No. 201180068712.1 dated Oct. 23, 2017.
Office Action in EP Application No. 11813500.3 dated Aug. 8, 2014.
Office Action in EP Application No. 11813500.3 dated Apr. 20, 2016.
Office Action in EP Application No. 11813500.3 dated Jul. 31, 2017.
Extended Search Report for EP Application No. 18153075.9 dated Apr. 5, 2018.
Exam Report from Indian Application No. 5653/DELNP/2013 dated Mar. 15, 2018.
Exam Report for ID Application No. P00201401703 dated Mar. 15, 2018.
Exam Report Stage II for ID Application No. W00201302799 dated Mar. 13, 2018.
Exam Report Stage II for ID Application No. W00201302800 dated Feb. 27, 2018.
Exam Report Stage I for ID Application No. W00201302694 dated Apr. 16, 2018.
Office Action in MX Application No. MX/a/2013/007681 dated Jul. 22, 2014.
Second Office Action in MX Application No. MX/a/2013/007681 dated Nov. 9, 2015.
Third Office Action in MX Application No. MX/a/2013/007681 dated Jun. 26, 2015.
Office Action in MX/a/2013/007692 dated Nov. 7, 2018.
Office Action in MY Application No. PI2013002501 dated Apr. 14, 2017.
Substantive Examination Adverse Report in MY Application No. PI2013002514 dated Jul. 31, 2018.
Exam Report for NZ Application No. 612,504 dated Dec. 24, 2013.
Search Report and Written Opinion for SG 201305009-1 dated Nov. 4, 2014.
Written Opinion for SG 201305009-1 dated May 11, 2015.
Examination Report for SG 201305009-1 dated Jan. 12, 2016.
Office Action for TW 100149994 dated May 11, 2017.
Office Action for TW 100149994 dated Nov. 28, 2018.
Office Action for VN 1-2013-01948 dated May 25, 2015.
Wood, Enteric nervous system, serotonin, and the irritable bowel syndrom, Current Opinion in Gastroenterology, Jan. 2001, vol. 17, No. 1„ pp. 91-97.
Bertino et al., "Effects of Holder Pasteurization on Human Milk Oligosaccharides," International J. Immunopathol. (2008), 21(2), pp. 381-385.
Chu et al., "Role of Se-Dependent Glutathoine Peroxidases in Gastrointestinal Inflammation and Cancer," Free Radical Biol. & Med., 2005, 36(12), p. 1481-1495.
Coppa et al., "Human Milk Oligosaccharides Inhibit the Adhesion to Caco-2 Cells of Diarrheal Pathogens: *Escherichia coli*, Vibrio cholerae, and *Salmonella fyris*," Pediatric Research, vol. 59, No. 3, 2006, pp. 377-382.
Friel, et al., "Evidence of Oxidative Stress in Full-Term Healthy Infants," Pediatric Research (2004), vol. 56, pp. 878-882.
Goedhart et al., "The Composition of Human Milk as a Model for the Design of Infant Formulas: Recent Findings and Possible Applications," Nutr. Res. Rev., (1994), 7, pp. 1-23.
Henningsson et al., "Short-Chain Fatty Acid Formatin at Fermentation of Indigestible Carbohydrates," Naringsforskning, vol. 45, No. 1, Dec. 1, 2001, pp. 165-168.
Kamm, "Why the enteric nervous system is important to clinicians", GUT, vol. 47, No. 9004, Dec. 1, 2000, pp. 8iv-9.
Kim,"Short-Chain Fatty Acids in Ulcerative Colitis," Nutrition Reviews, Jan. 1998, pp. 17-24.
Lawrence, RA, "Storage of Human Milk and the Influence of Procedures on Immunological Components of Human Milk," Acta Paediatr. Suppl., Aug. 1999, vol. 88, No. 430.
Nezami et al., "Enteric Nervous System in the Small Intestine: Pathophysiology and Clinical Implications," Current Gastroenterology Rep+361:518orts, vol. 12, No. 5, Oct. 20, 2010, pp. 358-365.
Ruiz-Palacios et al., "Campylobacter jejuni Binds Intestinal H(O) Antigen, and Fucosyloligosaccharides of Human Milk Inhibit Its Binding and Infection" J. Biol. Chem., 2003, 278(16), p. 14112-14120.
Sandin, et al., "Faecal Short Chain Fatty acid Pattern and Allergy in Early Childhood," ACTA Paediatrica, vol. 98, No. 5, May 1, 2009, pp. 823-827.
Saugstad, "Oxidative Stress in the Newborn—a 30-Year Perspective," Biol Neonate 2005, Vo. 88, pp. 228-236.
Schanler et al., "Randomized Trial of Donor Human Milk Versus Preterm Formula as Substitutes for Mothers' Own Milk in the Feeding of Extremely Premature Infants," Pediatrics, 2005, 116(2), pp. 400-406.
Schmelzle et al., "Randomized double-blind study of the nutritional efficacy and bifidogenicity of a new infant formula containing partially hydrolyzed protein, a high beta-palmitic acid level, and nondigestible oligosaccharides," J. Pediatr. Gastroenterol. Nutr., vol. 36(3), pp. 343-351 (2003).
Shen et al., "High-Performance Capillary Electrophoresis of Sialylated Oligosaccharides of Human Milk," Anal. Biochem., (2000), 279, pp. 37-45.

(56) References Cited

OTHER PUBLICATIONS

Walker, A., "Breast Milk as the Gold Standard for Protective Nutrients," J. Pediatrics, 2010, 156, p. S3-S7, available online Jan. 21, 2010.
Office Action from Canadian Patent Application No. 2,822,497 dated Sep. 26, 2018.
Office Action in Canadian Patent Application 2,822,660 dated Jan. 28, 2019.
Reexamination Decision from Chinese Application No. 201180068712.1 dated Oct. 10, 2018.
Office Action in EP Application No. 11813500.3 dated Jan. 8, 2019.
Office Action in MX/a/2014/002491 dated Jul. 30, 2018.
Office Action in VN 1-2013-02056 dated Nov. 19, 2018.
Anonymous, "Guidelines for the Evaluation of Probiotics in Food", Joint FAQ/WHO Working Group Report on Drafting Guidelines for the Evaluation of Probiotics in Food, Food and Agriculture Organization of the United Nations and the World Health Organization, London, Ontario, Canada, Apr. 30 and May 1, 2002.
Buhner et al., "Activation of Human Enteric Neurons by Supernatants of Colonic Biopsy Specimens from Patients with Irritable Bowel Syndrome," Gastroentrology 2009, vol. 137, pp. 1425-1434.
Wood, "Enteric Neuroimmunophysiology and Pathophysiology" Gastroenterology 2004, vol. 127, No. 2, pp. 635-657.
Office Action for U.S. Appl. No. 13/335,341 dated Mar. 21, 2019.
Amendment for U.S. Appl. No. 15/401,488 dated Apr. 15, 2019.
Response to Office Action for U.S. Appl. No. 15/791,052 dated Apr. 10, 2019.
Office Action in Canadian Patent Application 2,822,219 dated Mar. 12, 2019.
"Practical Inflammation Manual", pp. 2 to 7, with English Translation.
Amendment for U.S. Appl. No. 14/234,166 dated Apr. 30, 2019.
Office Action in Canadian Patent Application 2,842,672 dated Apr. 8, 2019.
English translation of First Office Action in CN 201610935257.5 dated Apr. 9, 2019.
Office Action in MX/a/2014/002491 dated Mar. 14, 2019.
Office action in MX/a/2013/007692 dated Apr. 11, 2019.
Yaping et al., Feeding Tolerance of Premature Babies, "All-Sided Strategies of Home Nursing of Premature Babies", Huazhong University of Science and Technology, the 1st edition of Feb. 2009, pp. 85-87—English Abstract.
Office Action from Canadian Patent Application No. 2,822,497 dated Apr. 29, 2019.
Amendment for U.S. Appl. No. 13/335,341 dated Jul. 22, 2019.
Office Action for U.S. Appl. No. 14/234,166 dated Aug. 19, 2019.
Notice of Allowance for U.S. Appl. No. 15/401,488 dated Aug. 21, 2019.
Office Action for U.S. Appl. No. 15/791,052 dated Jul. 17, 2019.
Decision on Rejection in CN 201711012480.3 dated Jul. 18, 2019.
Substantive Examination Adverse Report in MY Application No. PI2017000647 dated May 21, 2019.
Avery "Molecular Targets of Oxidative Stress," Biochem J., 2011, vol. 424, pp. 201-210.
Nittynen, et al., "Galacto-oligosaccharides and Bowel Functions," Scandinavian Journal of Food and Nutrition 2007, 51(2); pp. 62-66.
Van Dokkum et al., "Effect of Nondigestible Oligosaccharides on Large-Bowel Functions, Blood Lipid Concentrations and Glucose Absorption in Young Healthy Male Subjects," European Journal of Clinical Nutrition, No. 53, 1999, pp. 1-7.
Amendment for U.S. Appl. No. 13/334,933 dated Jul. 22, 2016.
Amendment for U.S. Appl. No. 13/335,341 dated Feb. 8, 2016.
Office Action for U.S. Appl. No. 13/335,341 dated Jun. 1, 2016.
Office Action for U.S. Appl. No. 14/234,166 dated Jun. 28, 2016.
Office Action in CA 2,846,603 dated Jun. 7, 2016.
Second Office Action in CN 201280046188.2 dated Nov. 9, 2015.
Decision of Rejection in CN 201280046188.2 dated Jun. 8, 2016.
Third Office Action in CN 201180067021.x dated Jan. 8, 2016.
Third Office Action in CN 201280051863.00 dated Apr. 5, 2016.
Communication for EP Application No. 11811618.5 dated Jul. 18, 2016.
Communication for EP Application No. 12741201.3 dated Mar. 16, 2016.
Exam Report for ID Application No. P00201400846 dated Jun. 26, 2016.
Exam Report for ID Application No. P00 2014 01703 dated Jul. 8, 2016.
Second Office Action in MX/a/2013/007675 dated Jun. 14, 2016.
Further Examination Report in NZ 620,311 dated May 24, 2016.
Final Examination Report in SG 2013050067 dated Feb. 19, 2016.
Final Examination Report in SG 201305083-6 dated May 19, 2016.
Written Opinion in SG 2014013478 dated Dec. 22, 2015.
Written Opinion in SG 2014004907 dated Apr. 12, 2016.
Search Report in TW Application No. 101126368 dated May 2, 2016.
Rejection of TW Application No. 100149846 dated Dec. 18, 2015.
Decision in TW Application No. 100150004 dated Jan. 28, 2016.
Kanamori et al. "Experience of long-term synbiotic therapy in seven short bowel patients with refractory enterocololitis," Journal of Pediatric Surgery, vol. 39, No. 11 (2004) pp. 1686-1692.
Leforestier et al., "Effects of galacto-oligosaccharide ingestion on the mucosa-associated mucins and sucrose activity in the small intestine of mice," Eur J. Nutr. (Dec. 2009), 48(8), pp. 457-464.
Miñana, "Oligosacaridos en la leche humana," Acta Pediatr Esp. (2007), 65(3), pp. 129-133.
Morrow et al., "Human-Milk Glycans that Inhibit Pathogen Binding Protect Breast-feeding Infants against Infectious Diarrhea", J. of Nutrition, American Society for Nutrition, v. 135, No. 5 (May 1, 2005), pp. 1304-1307.
Office Action for U.S. Appl. No. 14/234,166 dated Mar. 2, 2018.
Amendment for U.S. Appl. No. 13/335,341 dated Mar. 5, 2018.
Decision on Rejection in CN 201280051863.0 dated Feb. 14, 2018.
Substantive Examination Report in PH 1-2014-500185 dated Jan. 11, 2018.
Substantive Examination Report in PH 1-2013-501291 dated Jan. 26, 2018.
Substantive Examination Report in PH 1-2014-500394 dated Jan. 26, 2018.
Office Action in TW Application No. 101126368 dated Mar. 1, 2018.
Xiao-Ming "Nutritional Management of Newborn Infants: Practical Guidelines," World J. Gastroenterol, 14(40), 6133-6139, Oct. 28, 2008.
Office Action for U.S. Appl. No. 15/401,488 dated Apr. 4, 2018.
Office Action for U.S. Appl. No. 13/335,341 dated Oct. 24, 2019.
Response to Office Action for U.S. Appl. No. 15/791,052 dated Nov. 18, 2019.
Office Action for U.S. Appl. No. 15/791,052 dated Dec. 11, 2019.
Office Action in CA 2,822,219 dated Nov. 20, 2019.
Second Office Action in CN 201711012480.3 dated Oct. 18, 2019.
Office action in MX/A/2013/007692 dated Nov. 7, 2019.
Office Action in CA 2,822,660 dated Feb. 27, 2020.
Office Action in CA 2,842,672 dated Feb. 25, 2020.

* cited by examiner

Figure 2

Table 1. Composition of microbiological medium used in the *in vitro* experiment.

| Component | Concentration in medium |
|---|---|
| | *mL/L* |
| Solution A[1] | 330.0 |
| Solution B[2] | 330.0 |
| Trace mineral solution[3] | 10.0 |
| Water-soluble vitamin solution[4] | 20.0 |
| Folate:biotin solution[5] | 5.0 |
| Riboflavin solution[6] | 5.0 |
| Hemin solution[7] | 2.5 |
| Resazurin[8] | 1.0 |
| Distilled $H_2O$ | 296.1 |
| | *g/L* |
| $Na_2CO_3$ | 4.0 |
| Cysteine HCl-$H_2O$ | 0.5 |
| Trypticase | 0.5 |
| Yeast extract | 0.5 |

[1]Composition (g/L): NaCl, 5.4; $KH_2PO_4$, 2.7; $CaCl_2$-$H_2O$, 0.16; $MgCl_2$-$6H_2O$, 0.12; $MnCl_2$-$4H_2O$, 0.06; $CoCl_2$-$6H_2O$, 0.06; $(NH_4)_2SO_4$, 5.4.
[2]Composition (g/L): $K_2HPO_4$, 2.7.
[3]Composition (mg/L): ethylenediaminetetraacetic acid (disodium salt), 500; $FeSO_4$-$7H_2O$, 200; $ZnSO_4$-$7H_2O$, 10; $MnCl_2$-$4H_2O$, 3; $H_3PO_4$, 30; $CoCl_2$-$6H_2O$, 20; $CuCl_2$-$2H_2O$, 1; $NiCl_2$-$6H_2O$, 2; $Na_2MoO_4$-$2H_2O$, 3.
[4]Composition (mg/L): thiamin-HCl, 100; d-pantothenic acid, 100; niacin, 100; pyridoxine, 100; p-aminobenzoic acid, 5; vitamin $B_{12}$, 0.25.
[5]Composition (mg/L): folic acid, 10; d-biotin, 2; $NH_4HCO_3$, 100.
[6]Composition: riboflavin, 10 mg/mL in 5 mmol/L of Hepes.
[7]Composition: hemin, 500 mg/mL in 10 mmol/L of NaOH.
[8]Composition: resazurin, 1 g/L in distilled $H_2O$.

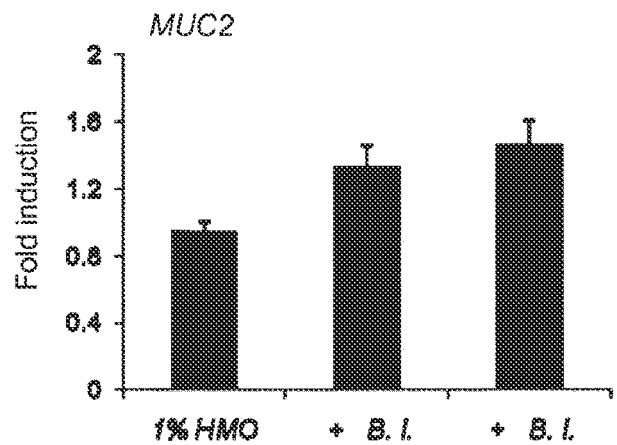
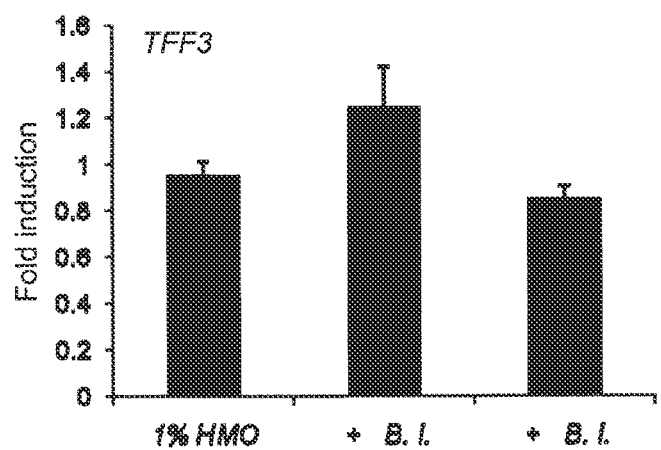

HUMAN MILK OLIGOSACCHARIDES FOR PREVENTING INJURY AND/OR PROMOTING HEALING OF THE GASTROINTESTINAL TRACT

CROSS REFERENCE TO RELATED APPLICATIONS

This application is the U.S. national stage entry of PCT/US2012/050569, with an international filing date of 13 Aug. 2012, which is herein incorporated by reference in its entirety and which claims priority to and any other benefit of U.S. Provisional Application Ser. No. 61/528,437, with a filing date of 29 Aug. 2011, which is herein incorporated by reference in its entirety.

FIELD OF THE DISCLOSURE

The present disclosure relates to the use of human milk oligosaccharides for preventing injury to the gastrointestinal tract and/or enhancing the healing of an injured gastrointestinal tract in an individual. More particularly, the present disclosure relates to human milk fortifiers, preterm and term infant formulas, pediatric formulas, follow on formulas, and adult nutritionals comprising human milk oligosaccharides that can enhance the expression of various mucin-associated proteins, thereby improving an individual's gastrointestinal prevention and repair function.

BACKGROUND OF THE DISCLOSURE

Individuals undergoing various therapies or having various diseases and/or conditions are generally more susceptible to intestinal mucosa (gastrointestinal) injury or compromised gastrointestinal tracts than are healthy individuals. The expression of mucin-associated proteins, or secretory proteins, is an integral part of an individual's natural ability to prevent and/or repair intestinal injuries. Specifically, the expression of these mucin-associated proteins aids in the healing of intestinal mucosa injuries and in the prevention of further injuries by protecting the mucosa from insults, stabilizing the mucus layer, reducing inflammation of the mucus layer, and promoting the healing of the epithelial tissue.

Not all individuals, however, have an adequate expression of mucin-associated proteins to affect prevention and needed intestinal repair, which may result in an increased risk of translocation, sepsis, and possibly death. Further, there are currently no commercially available nutritional compositions that contain mucin-associated proteins, such as trefoil factor 3 (TFF3), or known methods of increasing the expression of mucin-associated proteins through the administration of an additional component to aid individuals having inadequate natural intestinal repair functions.

As such, it would be desirable to provide nutritional compositions that can produce nutritional benefits such as aiding in the prevention and healing of intestinal mucosal injuries by enhancing the expression of mucin-associated proteins. It would additionally be beneficial if the nutritional compositions could also improve the barrier function, enhance healing of epithelial cells, and reduce the inflammation of the injured gastrointestinal tract.

SUMMARY OF THE DISCLOSURE

The present disclosure is directed to the use of nutritional compositions, including human milk fortifiers, preterm and term infant formulas, pediatric formulas, follow on formulas and adult formulas including human milk oligosaccharides alone or in combination with other components such as other prebiotic oligosaccharides and/or probiotics, for preventing injury to the gastrointestinal tract and/or enhancing the healing of the gastrointestinal tract of an infant, toddler, child, or adult. More particularly, the nutritional compositions can improve gastrointestinal healing through enhancing the expression of various mucin-associated proteins, which can stabilize the mucus layer, reduce inflammation, and promote healing of epithelial tissue.

One embodiment is directed to a method of enhancing healing of the gastrointestinal tract of an individual. The method comprises identifying an individual having an injured gastrointestinal tract and administering to the individual a nutritional composition comprising a human milk oligosaccharide.

Another embodiment is directed to a method of reducing the incidence of intestinal mucosa injury. The method comprises identifying an individual susceptible to an intestinal mucosa injury and administering to the individual a nutritional composition comprising a human milk oligosaccharide.

Another embodiment is directed to a method of improving the barrier function in the gastrointestinal tract of an individual. The method comprises identifying an individual in need of an increased barrier function of the gastrointestinal tract and administering to the individual a nutritional composition comprising a human milk oligosaccharide.

Another embodiment is directed to a method of reducing the incidence of inflammation of the gastrointestinal tract of an individual. The method comprises identifying an individual susceptible to inflammation of the gastrointestinal tract and administering to the individual a nutritional composition comprising a human milk oligosaccharide.

It has now been discovered that human milk oligosaccharides can enhance the expression of various mucin-associated proteins, such as TFF3, MUC2, and RELMβ, which are an integral part of the intestinal repair system. Specifically, it has been found that enhancing the expression of these mucin-associated proteins through the administration of a composition containing human milk oligosaccharides, aids in cell healing, resolution of inflammation, and promotion of barrier function. It has further been found that the human milk oligosaccharides can enhance the healing of the gastrointestinal tract by enhancing the production of isobutyrate in the colon. Specifically, it has been found that although colonocytes in the colon of a healthy individual prefer to utilize butyrate as an energy source versus other short-chain fatty acids, the colonocytes in the colon of an individual undergoing an extended period of starvation, such as would occur prior to feeding initiation in preterm infants or following gastrointestinal surgery, have an impaired ability to oxidize butyrate but retain an ability to utilize isobutyrate for energy and anapleurosis.

BRIEF DESCRIPTION OF THE DRAWINGS

FIG. 2 is a table setting forth the microbiological medium used in the in vitro experiment of Example 78.

FIGS. 5A-5D are charts depicting the effect of the combinations of HMOs and *Bifidobacterium infantis* and *Bifidobacterium lactis* on the expression of several genes involved in the healing response of the gastrointestinal tract as measured in Example 79.

DETAILED DESCRIPTION OF THE DISCLOSURE

Figure 1A:
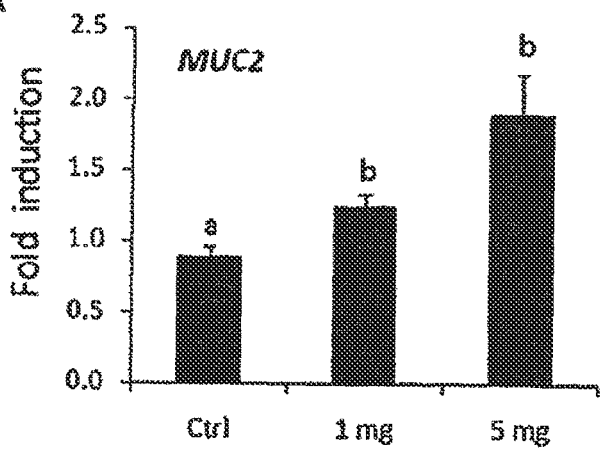
FIGS. 1A-1E are charts depicting the effect of human milk oligosaccharides and dose dependency thereof on the expression of several genes involved in the healing response of the gastrointestinal tract as measured in Example 77.

The nutritional compositions and methods described herein utilize human milk oligosaccharides (HMOs) alone or in combination with one or more additional components for preventing injury to the gastrointestinal tract and/or enhancing the healing of the gastrointestinal tract. These and other essential features of the nutritional compositions and methods, as well as some of the many optional variations and additions, are described in detail hereafter.

The term "retort packaging" and "retort sterilizing" are used interchangeably herein, and unless otherwise specified, refer to the common practice of filling a container, most typically a metal can or other similar package, with a nutritional liquid and then subjecting the liquid-filled package to the necessary heat sterilization step, to form a sterilized, retort packaged, nutritional liquid product.

The term "aseptic packaging" as used herein, unless otherwise specified, refers to the manufacture of a packaged product without reliance upon the above-described retort packaging step, wherein the nutritional liquid and package are sterilized separately prior to filling, and then are combined under sterilized or aseptic processing conditions to form a sterilized, aseptically packaged, nutritional liquid product.

The terms "fat" and "oil" as used herein, unless otherwise specified, are used interchangeably to refer to lipid materials derived or processed from plants or animals. These terms also include synthetic lipid materials so long as such synthetic materials are suitable for oral administration to humans.

The term "human milk oligosaccharide" or "HMO", unless otherwise specified, refers generally to a number of complex carbohydrates found in human breast milk that can be in acidic or neutral form, and to precursors thereof. Exemplary non-limiting human milk oligosaccharides include 3'-sialyllactose, 6'-sialyllactose, 3'-fucosyllactose, 2'-fucosyllactose, lacto-N-neo-tetraose, and disialyllacto-N-tetraose. An exemplary human milk oligosaccharide precursor includes sialic acid.

The term "shelf stable" as used herein, unless otherwise specified, refers to a nutritional product that remains commercially stable after being packaged and then stored at 18-24° C. for at least 3 months, including from about 6 months to about 24 months, and also including from about 12 months to about 18 months.

The terms "nutritional formulation" or "nutritional composition" as used herein, are used interchangeably and, unless otherwise specified, refer to synthetic formulas including nutritional liquids, nutritional powders, nutritional supplements, and any other nutritional food product as known in the art. The nutritional powders may be reconstituted to form a nutritional liquid, all of which comprise one or more of fat, protein and carbohydrate and are suitable for oral consumption by a human.

The term "nutritional liquid" as used herein, unless otherwise specified, refers to nutritional compositions in ready-to-drink liquid form, concentrated form, and nutritional liquids made by reconstituting the nutritional powders described herein prior to use.

The term "nutritional powder" as used herein, unless otherwise specified, refers to nutritional compositions in flowable or scoopable form that can be reconstituted with water or another aqueous liquid prior to consumption and includes both spraydried and drymixed/dryblended powders.

The term "infant" as used herein, unless otherwise specified, refers to a person 12 months or younger. The term "preterm infant" as used herein, refers to a person born prior to 36 weeks of gestation.

The term "toddler" as used herein, unless otherwise specified, refers to a person greater than one year of age up to three years of age.

The term "child" as used herein, unless otherwise specified, refers to a person greater than three years of age up to twelve years of age.

The term "newborn" as used herein, unless otherwise specified, refers to a person from birth up to four weeks of age.

The terms "infant formula" or "synthetic infant formula" as used herein, unless otherwise specified, are used interchangeably and refer to liquid and solid human milk replacements or substitutes that are suitable for consumption by an infant. The synthetic formulas include components that are of semi-purified or purified origin. As used herein, unless otherwise specified, the terms "semi-purified" or "purified" refer to a material that has been prepared by purification of a natural material or by synthesis. The terms "infant formula" or "synthetic infant formula" do not include human breast milk.

The term "preterm infant formula" as used herein, unless otherwise specified, refers to liquid and solid nutritional products suitable for consumption by a preterm infant.

The term "human milk fortifier" as used herein, unless otherwise specified, refers to liquid and solid nutritional products suitable for mixing with breast milk or preterm infant formula or infant formula for consumption by a preterm or term infant.

The terms "susceptible" and "at risk" as used herein, unless otherwise specified, mean having little resistance to a certain condition or disease, including being genetically predisposed, having a family history of, and/or having symptoms of the condition or disease.

All percentages, parts and ratios as used herein, are by weight of the total composition, unless otherwise specified. All such weights, as they pertain to listed ingredients, are based on the active level and, therefore, do not include solvents or by-products that may be included in commercially available materials, unless otherwise specified.

Numerical ranges as used herein are intended to include every number and subset of numbers within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The nutritional compositions and methods may comprise, consist of, or consist essentially of the essential elements of the compositions and methods as described herein, as well as any additional or optional element described herein or otherwise useful in nutritional composition applications.

Product Form

The nutritional compositions of the present disclosure including the HMOs may be formulated and administered in any known or otherwise suitable oral product form. Any solid, liquid, or powder product form, including combinations or variations thereof, are suitable for use herein, provided that such forms allow for safe and effective oral delivery to the individual of the essential ingredients and any optional ingredients, as also defined herein.

The nutritional compositions of the present disclosure are preferably formulated as dietary product forms, which are defined herein as those embodiments comprising the essential ingredients of the present disclosure in a product form that then contains at least one of fat, protein, and carbohydrate, and preferably also contains vitamins, minerals, or combinations thereof. The nutritional compositions will comprise HMOs, desirably in combination with at least one of protein, fat, vitamins, and minerals, to produce a nutritional combination.

The nutritional composition may be formulated with sufficient kinds and amounts of nutrients to provide a sole, primary, or supplemental source of nutrition, or to provide a specialized nutritional composition for use in individuals afflicted with specific diseases, disorders, or conditions or with a targeted nutritional benefit as described below.

Specific non-limiting examples of product forms suitable for use with the HMO-containing compositions as disclosed herein include, for example, liquid and powdered dietary supplements, liquid and powdered human milk fortifiers, liquid and powdered preterm infant formulas, liquid and powdered infant formulas, liquid and powdered elemental and semi-elemental formulas, liquid and powdered pediatric formulas, liquid and powdered toddler formulas, liquid and powdered follow-on formulas, liquid, powdered and solid adult nutritional formulas suitable for use with individuals suffering from enteric infection, inflammatory bowel disease, colitis, bowel obstruction, chronic stress, and other gastrointestinal diseases, conditions, and/or disorders or undergoing antibiotic therapy, radiation therapy, other chemotherapy, surgery, or other treatments or therapies.

Nutritional Liquids

Nutritional liquids include both concentrated and ready-to-feed nutritional liquids. These nutritional liquids are most typically formulated as suspensions or emulsions, although other liquid forms are within the scope of the present disclosure.

Nutritional emulsions suitable for use may be aqueous emulsions comprising proteins, fats, and carbohydrates. These emulsions are generally flowable or drinkable liquids at from about 1° C. to about 25° C. and are typically in the form of oil-in-water, water-in-oil, or complex aqueous emulsions, although such emulsions are most typically in the form of oil-in-water emulsions having a continuous aqueous phase and a discontinuous oil phase.

The nutritional emulsions may be and typically are shelf stable. The nutritional emulsions typically contain up to about 95% by weight of water, including from about 50% to about 95%, also including from about 60% to about 90%, and also including from about 70% to about 85%, by weight of water. The nutritional emulsions may have a variety of product densities, but most typically have a density greater than about 1.03 g/mL, including greater than about 1.04 g/mL, including greater than about 1.055 g/mL, including from about 1.06 g/ml to about 1.12 g/mL, and also including from about 1.085 g/mL to about 1.10 g/mL.

The nutritional emulsions may have a caloric density tailored to the nutritional needs of the ultimate user, although in most instances the emulsions comprise generally at least 19 kcal/fl oz (660 kcal/liter), more typically from about 20 kcal/fl oz (675-680 kcal/liter) to about 25 kcal/fl oz (820 kcal/liter), even more typically from about 20 kcal/fl oz (675-680 kcal/liter) to about 24 kcal/fl oz (800-810 kcal/liter). Generally, the 22-24 kcal/fl oz formulas are more commonly used in preterm or low birth weight infants, and the 20-21 kcal/fl oz (675-680 to 700 kcal/liter) formulas are more often used in term infants. In some embodiments, the emulsion may have a caloric density of from about 50-100 kcal/liter to about 2000 kcal/liter, including from about 150 kcal/liter to about 500 kcal/liter. In some specific embodiments, the emulsion may have a caloric density of 25, or 50, or 75, or 100 kcal/liter.

The nutritional emulsion may have a pH ranging from about 3.5 to about 8, but are most advantageously in a range of from about 4.5 to about 7.5, including from about 5.5 to about 7.3, including from about 6.2 to about 7.2.

Although the serving size for the nutritional emulsion can vary depending upon a number of variables, a typical serving size is generally at least about 1 mL, or even at least about 2 mL, or even at least about 5 mL, or even at least about 10 mL, or even at least about 25 mL, including ranges from about 2 mL to about 500 mL, including from about 4 mL to about 340 mL, and including from about 10 mL to about 240 mL.

Nutritional Solids

The nutritional solids may be in any solid form, but are typically in the form of flowable or substantially flowable particulate compositions, or at least particulate compositions. Particularly suitable nutritional solid product forms include spray dried, agglomerated and/or dryblended powder compositions. The compositions can easily be scooped and measured with a spoon or similar other device, and can easily be reconstituted by the intended user with a suitable aqueous liquid, typically water, to form a nutritional composition for immediate oral or enteral use. In this context, "immediate" use generally means within about 48 hours, most typically within about 24 hours, preferably right after reconstitution.

The nutritional powders may be reconstituted with water prior to use to a caloric density tailored to the nutritional needs of the ultimate user, although in most instances the powders are reconstituted with water to form compositions comprising at least 19 kcal/fl oz (660 kcal/liter), more typically from about 20 kcal/fl oz (675-680 kcal/liter) to about 25 kcal/fl oz (820 kcal/liter), even more typically from about 20 kcal/fl oz (675-680 kcal/liter) to about 24 kcal/fl oz (800-810 kcal/liter). Generally, the 22-24 kcal/fl oz formulas are more commonly used in preterm or low birth weight infants, and the 20-21 kcal/fl oz (675-680 to 700 kcal/liter) formulas are more often used in term infants. In some embodiments, the reconstituted powder may have a caloric density of from about 50-100 kcal/liter to about 2000 kcal/liter, including from about 150 kcal/liter to about 500 kcal/liter. In some specific embodiments, the emulsion may have a caloric density of 25, or 50, or 75, or 100 kcal/liter.

Human Milk Oligosaccharides (HMOs)

The nutritional compositions of the present disclosure include at least one HMO, and in many embodiments, a combination of two or more HMOs. Oligosaccharides are one of the main components of human breast milk, which contains, on average, 10 grams per liter of neutral oligosaccharides and 1 gram per liter of acidic oligosaccharides. The composition of human milk oligosaccharides is very complex and more than 200 different oligosaccharide-like structures are known.

The HMOs may be included in the nutritional compositions alone, or in some embodiments, in combination with other immune enhancing factors (e.g., LCPUFAs, antioxidants, nucleotides, etc.) as described herein.

Suitable HMOs for use in the nutritional compositions may include acidic oligosaccharides, neutral oligosaccharides, N-acetylglucosylated oligosaccharides, and HMO precursors. Specific non-limiting examples of HMOs that may be included individually or in combination in the compositions of the present disclosure include: sialic acid (i.e., free sialic acid, lipid-bound sialic acid, protein-bound sialic acid); D-glucose (Glc); D-galactose (Gal); N-acetylglucosamine (GlcNAc); L-fucose (Fuc); fucosyl oligosaccharides (i.e., Lacto-N-fucopentaose I; Lacto-N-fucopentaose II; 2'-Fucosyllactose; 3'-Fucosyllactose; Lacto-N-fucopentaose III; Lacto-N-difucohexaose I; and Lactodifucotetraose); non-fucosylated, non-sialylated oligosaccharides (i.e., Lacto-N-tetraose and Lacto-N-neotetraose); sialyl oligosaccharides (i.e., 3'-Sialyl-3-fucosyllactose; Disialomonofucosyllacto-N-neohexaose; Monofucosylmonosialyllacto-N-octaose (sialyl); Sialyllacto-N-fucohexaose II; Disialyllacto-N-fucopentaose II; Monofucosyldisialyllacto-N-tetraose); and sialyl fucosyl oligosaccharides (i.e., 2'-Sialyllactose; 2-Sialyllactosamine; 3'-Sialyllactose; 3'-Sialyllactosamine; 6'-Sialyllactose; 6'-Sialyllactosamine; Sialyllacto-N-neotetraose c; Monosialyllacto-N-hexaose; Disialyllacto-N-hexaose I; Monosialyllacto-N-neohexaose I; Monosialyllacto-N-neohexaose II; Disialyllacto-N-neohexaose; Disialyllacto-N-tetraose; Disialyllacto-N-hexaose II; Sialyllacto-N-tetraose a; Disialyllacto-N-hexaose I; and Sialyllacto-N-tetraose b). Also useful are variants in which the glucose (Glc at the reducing end is replaced by N-acetylglucosamine (e.g., 2'-fucosyl-N-acetylglucosamine (2'-FL-NAG) is such a variant to 2'-fucosyllactose). These HMOs are described more fully in U.S. Patent Application No. 2009/0098240, which is herein incorporated by reference in its entirety. Other suitable examples of HMOs that may be included in the compositions of the present disclosure include lacto-N-fucopentaose V, lacto-N-hexaose, para-lacto-N-hexaose, lacto-N-neohexaose, para-lacto-N-neohexaose, monofucosyllacto-N-hexaose II, isomeric fucosylated lacto-N-hexaose (1), isomeric fucosylated lacto-N-hexaose (3), isomeric fucosylated lacto-N-hexaose (2), difucosyl-para-lacto-N-neohexaose, difucosyl-para-lacto-N-hexaose, difucosyllacto-N-hexaose, lacto-N-neoocataose, para-lacto-N-octanose, iso-lacto-N-octaose, lacto-N-octaose, monofucosyllacto-neoocataose, monofucosyllacto-N-ocataose, difucosyllacto-N-octaose I, difucosyllacto-N-octaose II, difucosyllacto-N-neoocataose II, difucosyllacto-N-neoocataose I, lacto-N-decaose, trifucosyllacto-N-neooctaose, trifucosyllacto-N-octaose, trifucosyl-iso-lacto-N-octaose, lacto-N-difuco-hexaose II, sialyl-lacto-N-tetraose a, sialyl-lacto-N-tetraose b, sialyl-lacto-N-tetraose c, sialyl-fucosyl-lacto-N-tetraose I, sialyl-fucosyl-lacto-N-tetraose II, and disialyl-lacto-N-tetraose, and combinations thereof. Particularly suitable nutritional compositions include at least one of the following HMOs or HMO precursors: sialic acid (SA); 3'-Sialyllactose (3'SL); 6'-Sialyllactose (6'SL); 2'-Fucosyllactose (2'FL); 3'-Fucosyllactose (3'FL); Lacto-N-neotetraose (LNnT); and disialyllacto-N-tetraose (DSLNT). Particularly preferred nutritional compositions include at least 2'FL.

The HMOs are present in the nutritional compositions in total amounts of HMO in the composition (mg of HMO per mL of composition) of at least about 0.01 mg HMO per mL of composition, including from 0.01 mg to 20 mg HMO per mL of composition, and including from 0.01 mg to 2 mg of HMO per mL of composition. Typically, the amount of HMO in the nutritional composition will depend on the specific HMO or HMOs present and the amounts of other components in the nutritional compositions.

In one specific embodiment when the nutritional product is a nutritional powder, the total concentration of HMOs in the nutritional powder is from about 0.008% to about 15%, including from about 0.008% to about 1.5% (by weight of the nutritional powder).

In another specific embodiment, when the nutritional product is a ready-to-feed nutritional liquid, the total concentration of HMOs in the ready-to-feed nutritional liquid is from about 0.001% to about 2%, including from about 0.001% to about 1%, including from about 0.001% to about 0.5%, and further including from about 0.001% to about 0.1% (by weight of the ready-to-feed nutritional liquid).

In another specific embodiment when the nutritional product is a concentrated nutritional liquid, the total concentration of HMOs in the concentrated nutritional liquid is from about 0.002% to about 4%, including from about 0.002% to about 2%, including from about 0.002% to about 1%, and further including from about 0.02% to about 0.2% (by weight of the concentrated nutritional liquid).

Additional Prebiotic Oligosaccharides

The nutritional compositions of the present disclosure may, in addition to the HMOs described above, comprise an additional source or sources of prebiotic oligosaccharides. Suitable additional sources of prebiotic oligosaccharides for use in the nutritional compositions include any prebiotic oligosaccharide that is suitable for use in a nutritional composition and is compatible with the essential elements and features of such compositions. In some embodiments, the nutritional composition includes a combination of HMOs and one or more additional prebiotic oligosaccharide such that the composition provides a synergistic benefit to the end user, such as a synergistic benefit in improving the barrier function of the gastrointestinal tract.

One such additional prebiotic oligosaccharide includes galactose-containing oligosaccharides, commonly referred to as galactooligosaccharides (GOS). GOS are indigestible oligosaccharides containing one or more galactose molecule and one molecule of glucose connected through $\beta(1,4)$ and/or $\beta(1,6)$ glycosidic bonds. The GOS used in the compositions of the present disclosure may be selected from $\beta$-galactooligosaccharides, $\alpha$-galactooligosaccharides, and combinations thereof. In some embodiments, the GOS may be trans-galactooligosaccharides (T-GOS), which are a mixture of oligosaccharides consisting of D-glucose and D-galactose alone, or in combination with one or more other forms of GOS. T-GOS are produced from D-lactose via the action of the enzyme beta-galactosidase obtained from *Aspergillus oryzae*. T-GOS are resistant to digestion in the upper gastrointestinal tract and stimulate the growth of bifidobacteria in the large intestine.

The GOS may be generally represented by the formula: [galactose]n-glucose, wherein n is an integer between 1 and 20, and preferably is selected from 2, 3, 4, 5, 6, 7, 8, 9, or 10. The term "galactooligosaccharide" or "GOS" may also refer to a mixture of galactooligosaccharides having different chain lengths; that is, long chain lengths and/or short chain lengths. Galactooligosaccharides are commercially available as, for example, Vivinal® GOS (75% total solids, 60% of total solids GOS; Friesland) and GOS (Clasado).

Other non-limiting examples of suitable additional prebiotic oligosaccharides for use in the nutritional compositions described herein include prebiotic oligosaccharides that have a degree of polymerization (DP) of at least 2 monose units, which are not or only partially digested in the intestine by the action of acids or digestive enzymes present in the human upper digestive tract (small intestine and stomach), but which are fermentable by the human intestinal flora. The term "monose units" refers to units having a closed ring structure, preferably hexose, e.g., the pyranose or furanose forms. Particularly preferred oligosaccharides for use in combination with the HMOs in the nutritional compositions of the present disclosure include GOS, fructooligosaccharides (FOS), short chain fructooligosaccharides, inulin, polydextrose (PDX), pectin hydrolysate, gum fiber, and combinations thereof.

In one embodiment, the nutritional compositions include GOS in a total amount of from about 5 kg to about 160 kg per 1000 kg of nutritional composition, including from about 8 kg to about 160 kg per 1000 kg of nutritional composition, including from about 8 kg to about 80 kg per 1000 kg, including from about 8 kg to about 64 kg per 1000 kg, and including from about 164 kg to about 818 kg per 18,000 pounds of nutritional composition. In one embodiment, the nutritional composition is a human milk fortifier that provides GOS to a 1 kg preterm infant in an amount of from about 0.11 g to about 0.55 g of GOS per day.

In some particular embodiments, HMOs are used in combination with FOS. In other particular embodiments, HMOs are used in combination with GOS. In these particular embodiments, the weight ratio of HMOs to GOS is from about 1:1000 to about 2:1, including about 1:1, including about 1:10, including about 1:40, and also including about 1:99.

Probiotics

The nutritional compositions of the present disclosure may further comprise one or more probiotics in addition to the HMOs.

Non-limiting examples of suitable probiotic strains for use in the nutritional compositions including HMOs herein include the genus *Lactobacillus* including *L. acidophilus, L. amylovorus, L. brevis, L. bulgaricus, L. casei* spp. *casei, L. casei* spp. *rhamnosus, L. crispatus, L. delbrueckii* ssp. *lactis, L. fermentum, L. helveticus, L. johnsonii, L. paracasei, L. pentosus, L. plantarum, L. reuteri,* and *L. sake*; the genus *Bifidobacterium* including: *B. animalis, B. bifidum, B. breve, B. infantis, B. lactis* and *B. longum*; the genus *Pediococcus* including: *P. acidilactici*; the genus *Propionibacterium* including: *P. acidipropionici, P. freudenreichii, P. jensenii,* and *P. theonii*; and the genus *Streptococcus* including: *S. cremoris, S. lactis,* and *S. thermophilus*. Particularly preferred probiotics include *B. lactis* and *L. acidophilus*.

The probiotics may be present in the nutritional compositions in a total amount of at least about $10^4$ CFU/g composition, including from about $10^4$ CFU/g composition to about $10^{11}$ CFU/g composition, and including from about $10^5$ CFU/g composition to about $10^{10}$ CFU/g composition. Additionally, the probiotics may be included in the nutritional composition as live (viable) and/or dead (non-viable) cells.

Macronutrients

The nutritional compositions including the HMOs may be formulated to include at least one of protein, fat, and carbohydrate. In many embodiments, the nutritional compositions will include the HMOs in combination with protein, carbohydrate and fat.

Although total concentrations or amounts of the fat, protein, and carbohydrates may vary depending upon the product type (i.e., human milk fortifier, preterm infant formula, infant formula, toddler formula, pediatric formula, follow-on formula, adult nutritional, etc.), product form (i.e., nutritional solid, powder, ready-to-feed liquid, or concentrated liquid), and targeted dietary needs of the intended user, such concentrations or amounts most typically fall within one of the following embodied ranges, inclusive of any other essential fat, protein, and/or carbohydrate ingredients as described herein.

For the liquid preterm and term infant formulas, carbohydrate concentrations (including both HMOs and any other carbohydrate/oligosaccharide sources) most typically range from about 5% to about 40%, including from about 7% to about 30%, including from about 10% to about 25%, by weight of the preterm or term infant formula; fat concentrations most typically range from about 1% to about 30%, including from about 2% to about 15%, and also including from about 3% to about 10%, by weight of the preterm or term infant formula; and protein concentrations most typically range from about 0.5% to about 30%, including from about 1% to about 15%, and also including from about 2% to about 10%, by weight of the preterm or term infant formula.

For the liquid human milk fortifiers, carbohydrate concentrations (including both HMOs and any other carbohydrate/oligosaccharide sources) most typically range from about 10% to about 75%, including from about 10% to about 50%, including from about 20% to about 40%, by weight of the human milk fortifier; fat concentrations most typically range from about 10% to about 40%, including from about 15% to about 37%, and also including from about 18% to about 30%, by weight of the human milk fortifier; and protein concentrations most typically range from about 5% to about 40%, including from about 10% to about 30%, and also including from about 15% to about 25%, by weight of the human milk fortifier.

For the adult nutritional liquids, carbohydrate concentrations (including both HMOs and any other carbohydrate/ oligosaccharide sources) most typically range from about 5% to about 40%, including from about 7% to about 30%, including from about 10% to about 25%, by weight of the adult nutritional; fat concentrations most typically range from about 2% to about 30%, including from about 3% to about 15%, and also including from about 5% to about 10%, by weight of the adult nutritional; and protein concentrations most typically range from about 0.5% to about 30%, including from about 1% to about 15%, and also including from about 2% to about 10%, by weight of the adult nutritional.

The amount of carbohydrates, fats, and/or proteins in any of the liquid nutritional compositions described herein may also be characterized in addition to, or in the alternative, as a percentage of total calories in the liquid nutritional composition as set forth in the following table. These macronutrients for liquid nutritional compositions of the present disclosure are most typically formulated within any of the caloric ranges (embodiments A-F) described in the following table (each numerical value is preceded by the term "about").

| Nutrient % Total Cal. | Embodiment A | Embodiment B | Embodiment C |
|---|---|---|---|
| Carbohydrate | 0-98 | 2-96 | 10-75 |
| Protein | 0-98 | 2-96 | 5-70 |
| Fat | 0-98 | 2-96 | 20-85 |

| | Embodiment D | Embodiment E | Embodiment F |
|---|---|---|---|
| Carbohydrate | 30-50 | 25-50 | 25-50 |
| Protein | 15-35 | 10-30 | 5-30 |
| Fat | 35-55 | 1-20 | 2-20 |

In one specific example, liquid infant formulas (both ready-to-feed and concentrated liquids) include those embodiments in which the protein component may comprise from about 7.5% to about 25% of the caloric content of the formula; the carbohydrate component (including both HMOs and any other carbohydrate/oligosaccharide sources) may comprise from about 35% to about 50% of the total caloric content of the infant formula; and the fat component may comprise from about 30% to about 60% of the total caloric content of the infant formula. These ranges are provided as examples only, and are not intended to be limiting. Additional suitable ranges are noted in the following table (each numerical value is preceded by the term "about").

| Nutrient % Total Cal. | Embodiment G | Embodiment H | Embodiment I |
|---|---|---|---|
| Carbohydrates: | 20-85 | 30-60 | 35-55 |
| Fat: | 5-70 | 20-60 | 25-50 |
| Protein: | 2-75 | 5-50 | 7-40 |

When the nutritional composition is a powdered preterm or term infant formula, the protein component is present in an amount of from about 5% to about 35%, including from about 8% to about 12%, and including from about 10% to about 12% by weight of the preterm or term infant formula; the fat component is present in an amount of from about 10% to about 35%, including from about 25% to about 30%, and including from about 26% to about 28% by weight of the preterm or term infant formula; and the carbohydrate component (including both HMOs and any other carbohydrate/oligosaccharide sources) is present in an amount of from about 30% to about 85%, including from about 45% to about 60%, including from about 50% to about 55% by weight of the preterm or term infant formula.

For powdered human milk fortifiers, the protein component is present in an amount of from about 1% to about 55%, including from about 10% to about 50%, and including from about 10% to about 30% by weight of the human milk fortifier; the fat component is present in an amount of from about 1% to about 30%, including from about 1% to about 25%, and including from about 1% to about 20% by weight of the human milk fortifier; and the carbohydrate component (including both HMOs and any other carbohydrate/oligosaccharide sources) is present in an amount of from about 15% to about 75%, including from about 15% to about 60%, including from about 20% to about 50% by weight of the human milk fortifier.

For powdered adult nutritionals, the protein component is present in an amount of from about 10% to about 90%, including from about 30% to about 80%, and including from about 40% to about 75% by weight of the adult nutritional; the fat component is present in an amount of from about 0.5% to about 20%, including from about 1% to about 10%, and including from about 2% to about 5% by weight of the adult nutritional; and the carbohydrate component (including both HMOs and any other carbohydrate/oligosaccharide sources) is present in an amount of from about 5% to about 40%, including from about 7% to about 30%, including from about 10% to about 25% by weight of the adult nutritional.

The total amount or concentration of fat, carbohydrate, and protein, in the powdered nutritional compositions of the present disclosure can vary considerably depending upon the selected composition and dietary or medical needs of the intended user. Additional suitable examples of macronutrient concentrations are set forth below. In this context, the total amount or concentration refers to all fat, carbohydrate, and protein sources in the powdered composition. For powdered nutritional compositions, such total amounts or concentrations are most typically and preferably formulated within any of the embodied ranges described in the following table (each numerical value is preceded by the term "about').

| Nutrient % Total Cal. | Embodiment J | Embodiment K | Embodiment L |
|---|---|---|---|
| Carbohydrate | 1-85 | 30-60 | 35-55 |
| Fat | 5-70 | 20-60 | 25-50 |
| Protein | 2-75 | 5-50 | 7-40 |

Fat

The nutritional compositions of the present disclosure may optionally comprise any source or sources of fat. Suitable sources of fat for use herein include any fat or fat source that is suitable for use in an oral nutritional composition and is compatible with the essential elements and features of such composition. For example, in one specific embodiment, the fat is derived from long chain polyunsaturated fatty acids (LCPUFAs).

Exemplary LCPUFAs for use in the nutritional compositions include, for example, ω-3 LCPUFAs and ω-6 LCPUFAs. Specific LCPUFAs include docosahexaenoic acid (DHA), eicosapentaenoic acid (EPA), arachidonic acid (ARA), linoleic acid, linolenic acid (alpha linolenic acid) and gamma-linolenic acid derived from oil sources such as plant oils, marine plankton, fungal oils, and fish oils. In one particular embodiment, the LCPUFAs are derived from fish oils such as menhaden, salmon, anchovy, cod, halibut, tuna, or herring oil. Particularly preferred LCPUFAs for use in the nutritional compositions with the HMOs include DHA, ARA, EPA, and combinations thereof.

In order to reduce potential side effects of high dosages of LCPUFAs in the nutritional compositions, the content of LCPUFAs preferably does not exceed 3% by weight of the total fat content, including below 2% by weight of the total fat content, and including below 1% by weight of the total fat content in the nutritional composition.

The LCPUFA may be provided as free fatty acids, in triglyceride form, in diglyceride form, in monoglyceride form, in phospholipid form, or as a mixture of one or more of the above, preferably in triglyceride form. In another specific embodiment, the fat is derived from short chain fatty acids.

Additional non-limiting examples of suitable fats or sources thereof for use in the nutritional compositions described herein include coconut oil, fractionated coconut oil, soybean oil, corn oil, olive oil, safflower oil, high oleic safflower oil, oleic acids (EMERSOL 6313 OLEIC ACID, Cognis Oleochemicals, Malaysia), MCT oil (medium chain triglycerides), sunflower oil, high oleic sunflower oil, palm and palm kernel oils, palm olein, canola oil, marine oils, fish oils, fungal oils, algae oils, cottonseed oils, and combinations thereof.

Protein

The nutritional compositions of the present disclosure may optionally further comprise protein. Any protein source that is suitable for use in oral nutritional compositions and is compatible with the essential elements and features of such compositions is suitable for use in the nutritional compositions.

Non-limiting examples of suitable proteins or sources thereof for use in the nutritional compositions include hydrolyzed, partially hydrolyzed or non-hydrolyzed proteins or protein sources, which may be derived from any known or otherwise suitable source such as milk (e.g., casein, whey), animal (e.g., meat, fish), cereal (e.g., rice, corn), vegetable (e.g., soy) or combinations thereof. Non-limiting examples of such proteins include milk protein isolates, milk protein concentrates as described herein, casein protein isolates, extensively hydrolyzed casein, whey protein, sodium or calcium caseinates, whole cow milk, partially or completely defatted milk, soy protein isolates, soy protein concentrates, and so forth. In one specific embodiment, the nutritional compositions include a protein source derived from milk proteins of human and/or bovine origin.

In one embodiment, the protein source is a hydrolyzed protein hydrolysate. In this context, the terms "hydrolyzed protein" or "protein hydrolysates" are used interchangeably herein and include extensively hydrolyzed proteins, wherein the degree of hydrolysis is most often at least about 20%, including from about 20% to about 80%, and also including from about 30% to about 80%, even more preferably from about 40% to about 60%. The degree of hydrolysis is the extent to which peptide bonds are broken by a hydrolysis method. The degree of protein hydrolysis for purposes of characterizing the extensively hydrolyzed protein component of these embodiments is easily determined by one of ordinary skill in the formulation arts by quantifying the amino nitrogen to total nitrogen ratio (AN/TN) of the protein component of the selected liquid formulation. The amino nitrogen component is quantified by USP titration methods for determining amino nitrogen content, while the total nitrogen component is determined by the Tecator Kjeldahl method, all of which are well known methods to one of ordinary skill in the analytical chemistry art.

Suitable hydrolyzed proteins may include soy protein hydrolysate, casein protein hydrolysate, whey protein hydrolysate, rice protein hydrolysate, potato protein hydrolysate, fish protein hydrolysate, egg albumen hydrolysate, gelatin protein hydrolysate, combinations of animal and vegetable protein hydrolysates, and combinations thereof. Particularly preferred protein hydrolysates include whey protein hydrolysate and hydrolyzed sodium caseinate.

When used in the nutritional compositions, the protein source may include at least about 20% (by weight total protein) protein hydrolysate, including from about 30% to 100% (by weight total protein) protein hydrolysate, and including from about 40% to about 80% (by weight total protein) protein hydrolysate, and including about 50% (by weight total protein) protein hydrolysate. In one particular embodiment, the nutritional composition includes 100% (by weight total protein) protein hydrolysate.

Carbohydrate

In addition to the HMOs, the nutritional compositions of the present disclosure may further optionally comprise any other carbohydrates that are suitable for use in an oral nutritional composition and are compatible with the essential elements and features of such compositions.

Non-limiting examples of suitable carbohydrates or sources thereof for use in the nutritional compositions described herein may include maltodextrin, hydrolyzed or modified starch or cornstarch, glucose polymers, corn syrup, corn syrup solids, rice-derived carbohydrates, pea-derived carbohydrates, potato-derived carbohydrates, tapioca, sucrose, glucose, fructose, lactose, high fructose corn syrup, honey, sugar alcohols (e.g., maltitol, erythritol, sorbitol), artificial sweeteners (e.g., sucralose, acesulfame potassium, stevia) and combinations thereof. A particularly desirable carbohydrate is a low dextrose equivalent (DE) maltodextrin.

Other Optional Ingredients

The nutritional compositions of the present disclosure may further comprise other optional components that may modify the physical, chemical, aesthetic or processing characteristics of the compositions or serve as pharmaceutical or additional nutritional components when used in the targeted population. Many such optional ingredients are known or otherwise suitable for use in medical food or other nutritional products or pharmaceutical dosage forms and may also be used in the compositions herein, provided that such optional ingredients are safe for oral administration and are compatible with the essential and other ingredients in the selected product form.

Non-limiting examples of such optional ingredients include preservatives, emulsifying agents, buffers, pharmaceutical actives, anti-inflammatory agents, additional nutrients as described herein, colorants, flavors, thickening agents and stabilizers, emulsifying agents, lubricants, and so forth.

The nutritional compositions may further comprise a sweetening agent, preferably including at least one sugar alcohol such as maltitol, erythritol, sorbitol, xylitol, mannitol, isolmalt, and lactitol, and also preferably including at least one artificial or high potency sweetener such as acesulfame K, aspartame, sucralose, saccharin, stevia, and tagatose. These sweetening agents, especially as a combination of a sugar alcohol and an artificial sweetener, are especially useful in formulating liquid beverage embodiments of the present disclosure having a desirable favor profile. These sweetener combinations are especially effective in masking undesirable flavors sometimes associated with the addition of vegetable proteins to a liquid beverage. Optional sugar alcohol concentrations in the nutritional composition may range from at least 0.01%, including from 0.1% to about 10%, and also including from about 1% to about 6%, by weight of the nutritional composition. Optional artificial sweetener concentrations may range from about 0.01%, including from about 0.05% to about 5%, also including from about 0.1% to about 1.0%, by weight of the nutritional composition.

A flowing agent or anti-caking agent may be included in the nutritional compositions as described herein to retard clumping or caking of the powder over time and to make a powder embodiment flow easily from its container. Any known flowing or anti-caking agents that are known or otherwise suitable for use in a nutritional powder or product form are suitable for use herein, non-limiting examples of which include tricalcium phosphate, silicates, and combinations thereof. The concentration of the flowing agent or anti-caking agent in the nutritional composition varies depending upon the product form, the other selected ingredients, the desired flow properties, and so forth, but most typically range from about 0.1% to about 4%, including from about 0.5% to about 2%, by weight of the nutritional composition.

A stabilizer may also be included in the nutritional compositions. Any stabilizer that is known or otherwise suitable for use in a nutritional composition is also suitable for use herein, some non-limiting examples of which include gums such as xanthan gum. The stabilizer may represent from about 0.1% to about 5.0%, including from about 0.5% to about 3%, including from about 0.7% to about 1.5%, by weight of the nutritional composition.

Additionally, the nutritional compositions may comprise one or more antioxidants to provide nutritional support, as well as to reduce oxidative stress. Any antioxidants suitable for oral administration may be included for use in the nutritional compositions of the present disclosure, including, for example, vitamin A, vitamin E, vitamin C, retinol, tocopherol, and carotenoids.

In one specific embodiment, the antioxidants for use in the nutritional compositions include carotenoids such as lutein, zeaxanthin, lycopene, beta-carotene, and combinations thereof, and particularly, combinations of the carotenoids lutein, lycopene, and beta-carotene. Nutritional compositions containing these combinations, as selected and defined herein, can be used to modulate inflammation and/or levels of C-reactive protein in preterm and term infants The nutritional compositions may further comprise any of a variety of other vitamins or related nutrients, non-limiting examples of which include vitamin D, vitamin K, thiamine, riboflavin, pyridoxine, vitamin $B_{12}$, niacin, folic acid, pantothenic acid, biotin, choline, inositol, salts and derivatives thereof, and combinations thereof.

The nutritional compositions may further comprise any of a variety of other additional minerals, non-limiting examples of which include calcium, phosphorus, magnesium, iron, zinc, manganese, copper, sodium, potassium, molybdenum, chromium, chloride, and combinations thereof.

The nutritional compositions of the present disclosure may additionally comprise nucleotides and/or nucleotide precursors selected from the group consisting of nucleoside, purine base, pyrimidine base, ribose and deoxyribose to further improve intestinal barrier integrity and/or maturation. The nucleotide may be in monophosphate, diphosphate, or triphosphate form. The nucleotide may be a ribonucleotide or a deoxyribonucleotide. The nucleotides may be monomeric, dimeric, or polymeric (including RNA and DNA). The nucleotide may be present in the nutritional composition as a free acid or in the form of a salt, preferably a monosodium salt.

Suitable nucleotides and/or nucleosides for use in the nutritional compositions include one or more of cytidine 5'-monophosphate, uridine 5'-monophosphate, adenosine 5'-monophosphate, guanosine 5'-1-monophosphate, and/or inosine 5'-monophosphate, more preferably cytidine 5'-monophosphate, uridine 5'-monophosphate, adenosine 5'-monophosphate, guanosine 5'-monophosphate, and inosine 5'-monophosphate.

Methods of Manufacture

The nutritional compositions of the present disclosure may be prepared by any known or otherwise effective manufacturing technique for preparing the selected product solid or liquid form. Many such techniques are known for any given product form such as nutritional liquids or powders and can easily be applied by one of ordinary skill in the art to the nutritional compositions described herein.

The nutritional compositions of the present disclosure can therefore be prepared by any of a variety of known or otherwise effective formulation or manufacturing methods. In one suitable manufacturing process, for example, at least three separate slurries are prepared, including a protein-in-fat (PIF) slurry, a carbohydrate-mineral (CHO-MIN) slurry, a protein-in-water (PIW) slurry. The PIF slurry is formed by heating and mixing the oil (e.g., canola oil, corn oil, etc.) and then adding an emulsifier (e.g., lecithin), fat soluble vitamins, and a portion of the total protein (e.g., milk protein concentrate, etc.) with continued heat and agitation. The CHO-MIN slurry is formed by adding with heated agitation to water: minerals (e.g., potassium citrate, dipotassium phosphate, sodium citrate, etc.), trace and ultra trace minerals (TM/UTM premix), thickening or suspending agents (e.g. avicel, gellan, carrageenan). The resulting CHO-MIN slurry is held for 10 minutes with continued heat and agitation before adding additional minerals (e.g., potassium chloride, magnesium carbonate, potassium iodide, etc.), and/or carbohydrates (e.g., GOS, HMOs, fructooligosaccharide, sucrose, corn syrup, etc.). The PIW slurry is then formed by mixing with heat and agitation the remaining protein, if any.

The resulting slurries are then blended together with heated agitation and the pH adjusted to 6.6-7.0, after which the composition is subjected to high-temperature short-time (HTST) processing during which the composition is heat treated, emulsified and homogenized, and then allowed to cool. Water soluble vitamins and ascorbic acid are added, the pH is adjusted to the desired range if necessary, flavors are added, and water is added to achieve the desired total solid level. The composition is then aseptically packaged to form an aseptically packaged nutritional emulsion. This emulsion can then be further diluted, heat-treated, and packaged to form a ready-to-feed or concentrated liquid, or it can be heat-treated and subsequently processed and packaged as a reconstitutable powder, e.g., spray dried, drymixed, agglomerated.

The nutritional solid, such as a spray dried nutritional powder or drymixed nutritional powder, may be prepared by any collection of known or otherwise effective techniques, suitable for making and formulating a nutritional powder.

For example, when the nutritional powder is a spray dried nutritional powder, the spray drying step may likewise include any spray drying technique that is known for or otherwise suitable for use in the production of nutritional powders. Many different spray drying methods and techniques are known for use in the nutrition field, all of which are suitable for use in the manufacture of the spray dried nutritional powders herein.

One method of preparing the spray dried nutritional powder comprises forming and homogenizing an aqueous slurry or liquid comprising predigested fat, and optionally protein, carbohydrate, and other sources of fat, and then spray drying the slurry or liquid to produce a spray dried nutritional powder. The method may further comprise the step of spray drying, drymixing, or otherwise adding additional nutritional ingredients, including any one or more of the ingredients described herein, to the spray dried nutritional powder.

Other suitable methods for making nutritional compositions are described, for example, in U.S. Pat. No. 6,365,218 (Borschel, et al.), U.S. Pat. No. 6,589,576 (Borschel, et al.), U.S. Pat. No. 6,306,908 (Carlson, et al.), U.S. Patent Application No. 20030118703 A1 (Nguyen, et al.), which descriptions are incorporated herein by reference to the extent that they are consistent herewith.

Methods of Use

The nutritional compositions as described herein and containing HMOs can be used to prevent injury to the gastrointestinal tract and/or to enhance the healing of an injured gastrointestinal tract of preterm infants, infants, toddlers, children, and adults. Any of this group may actually have an injured gastrointestinal tract and thus benefit from the healing action of the HMO-containing nutritional composition, or may be at risk of or susceptible to sustaining injuries to the gastrointestinal tract and thus benefit from the preventative action of the HMO-containing nutritional composition.

The nutritional compositions as described herein comprise HMOs, alone or in combination with one or more additional components, such as a probiotic as noted above, to provide a nutritional source for improving at least the intestinal repair/healing function of an individual. Specifically, the nutritional compositions can enhance the expression of mucin-associated proteins, such as trefoil factor 3 (TFF3), mucin 2 (MUC2), and relm-beta (RELMβ) to stabilize the mucus layer; promote healing of epithelial cells; improve barrier function; and reduce inflammation, each of which enhance the overall healing of the epithelial tissue and mucus layer of the stomach, small intestine, and large intestine.

In addition, the nutritional compositions can provide a nutritional source for improving at least the intestinal repair/healing function of an individual by enhancing the production of isobutyrate in the colon, and as such, enhancing the healing of the colonocytes in the colon. Specifically, although colonocytes in the colon of a healthy individual prefer to utilize butyrate as an energy source versus other short-chain fatty acids, the colonocytes in the colon of an individual undergoing an extended period of starvation, such as would occur prior to feeding initiation in preterm infants or following gastrointestinal surgery, have an impaired ability to oxidize butyrate. These colonocytes, however, retain an ability to utilize isobutyrate for energy and anapleurosis. As such, by increasing the amount of isobutyrate produced through the administration of the HMO containing composition, gastrointestinal healing can be improved.

In some embodiments, the nutritional compositions may be administered to an individual who has sustained injury to the gastrointestinal tract or who is more susceptible to or at risk of injury to the gastrointestinal tract by having undergone various therapies, which may include, for example, antibiotic therapy, radiation therapy, chemotherapy, or surgery or by having various diseases or disorders, which may include, for example, enteric infection, inflammatory bowel diseases, colitis, bowel obstruction, and chronic stress.

The individual desirably consumes at least one serving of the HMO-containing nutritional composition daily, and in some embodiments, may consume two, three, or even more servings per day. Each serving is desirably administered as a single undivided dose, although the serving may also be divided into two or more partial or divided servings to be taken at two or more times during the day. The methods of the present disclosure include continuous day after day administration, as well as periodic or limited administration, although continuous day after day administration is generally desirable.

The nutritional composition may be administered to the individual orally or via tube feeding. The nutritional compositions of the present disclosure could also be given to preterm or term infants prior to the initiation of enteral feeding and/or concurrently with feeding. Furthermore, the nutritional composition may be given to infants, children, or adults prior to or concurrently with re-feeding after partial or total parenteral nutrition.

EXAMPLES

The following examples illustrate specific embodiments and/or features of the nutritional compositions and methods of the present disclosure. The examples are given solely for the purpose of illustration and are not to be construed as limitations of the present disclosure, as many variations thereof are possible without departing from the spirit and scope of the disclosure. All exemplified amounts are weight percentages based upon the total weight of the composition, unless otherwise specified.

The exemplified compositions are shelf stable nutritional compositions prepared in accordance with the manufacturing methods described herein, such that each exemplified composition, unless otherwise specified, includes an aseptically processed embodiment and a retort packaged embodiment.

The nutritional liquid embodiments are aqueous oil-in-water emulsions that are packaged in 240 mL plastic containers, or alternative package sizes, and remain physically stable for 12-18 months after composition/packaging at storage temperatures ranging from 1-25° C.

Examples 1-5

Examples 1-20 illustrate spray dried nutritional powders of the present disclosure, the ingredients of which are listed in the table below. All ingredient amounts are listed as kilogram per 1000 kilogram batch of product, unless otherwise specified.

| Ingredient | Ex. 1 | Ex. 2 | Ex. 3 | Ex. 4 | Ex. 5 |
| --- | --- | --- | --- | --- | --- |
| Corn syrup | 256.86 kg | 256.86 kg | 256.86 kg | 256.86 kg | 256.86 kg |
| Corn Maltodextrin | 216.25 kg | 216.25 kg | 216.25 kg | 216.25 kg | 216.25 kg |
| Sucrose | 177.95 kg | 177.95 kg | 177.95 kg | 177.95 kg | 177.95 kg |
| Corn oil | 155.40 kg | 155.40 kg | 155.40 kg | 155.40 kg | 155.40 kg |
| Casein | 132.97 kg | 132.97 kg | 132.97 kg | 132.97 kg | 132.97 kg |
| Soy protein isolate | 29.84 kg | 29.84 kg | 29.84 kg | 29.84 kg | 29.84 kg |
| Calcium caseinate | 19.46 kg | 19.46 kg | 19.46 kg | 19.46 kg | 19.46 kg |
| 20% potassium citrate | 16.09 kg | 16.09 kg | 16.09 kg | 16.09 kg | 16.09 kg |
| Vanilla | 14.55 kg | 14.55 kg | 14.55 kg | 14.55 kg | 14.55 kg |
| 20% sodium hydroxide | 13.77 kg | 13.77 kg | 13.77 kg | 13.77 kg | 13.77 kg |
| Human Milk Oligosaccharides | 0.08 kg | 0.40 kg | 0.80 kg | 4.00 kg | 40.00 kg |
| Potassium citrate | 7.54 kg | 7.54 kg | 7.54 kg | 7.54 kg | 7.54 kg |
| Magnesium chloride | 7.53 kg | 7.53 kg | 7.53 kg | 7.53 kg | 7.53 kg |
| Tricalcium phosphate | 6.23 kg | 6.23 kg | 6.23 kg | 6.23 kg | 6.23 kg |
| Sodium citrate | 5.66 kg | 5.66 kg | 5.66 kg | 5.66 kg | 5.66 kg |
| Potassium chloride | 3.79 kg | 3.79 kg | 3.79 kg | 3.79 kg | 3.79 kg |
| Soy lecithin | 3.44 kg | 3.44 kg | 3.44 kg | 3.44 kg | 3.44 kg |

-continued

| Ingredient | | | | | |
|---|---|---|---|---|---|
| Ascorbic acid | 1.91 kg | 1.91 kg | 1.91 kg | 1.91 kg | 1.91 kg |
| Choline chloride | 1.64 kg | 1.64 kg | 1.64 kg | 1.64 kg | 1.64 kg |
| 45% KOH | 1.26 kg | 1.26 kg | 1.26 kg | 1.26 kg | 1.26 kg |
| Zinc sulfate | 0.1558 kg | 0.1558 kg | 0.1558 kg | 0.1558 kg | 0.1558 kg |
| Ferrous sulfate | 0.121700 kg | 0.121700 kg | 0.121700 kg | 0.121700 kg | 0.121700 kg |
| Manganese sulfate | 0.036900 kg | 0.036900 kg | 0.036900 kg | 0.036900 kg | 0.036900 kg |
| Cupric sulfate | 0.021100 kg | 0.021100 kg | 0.021100 kg | 0.021100 kg | 0.021100 kg |
| Chromium chloride | 0.001280 kg | 0.001280 kg | 0.001280 kg | 0.001280 kg | 0.001280 kg |
| Sodium molybdate | 0.001012 kg | 0.001012 kg | 0.001012 kg | 0.001012 kg | 0.001012 kg |
| Sodium selenate | 0.000434 kg | 0.000434 kg | 0.000434 kg | 0.000434 kg | 0.000434 kg |
| Niacinamide | 0.124200 kg | 0.124200 kg | 0.124200 kg | 0.124200 kg | 0.124200 kg |
| D-calcium pantothenate | 0.083000 kg | 0.083000 kg | 0.083000 kg | 0.083000 kg | 0.083000 kg |
| Thiamine chloride hydrochloride | 0.020510 kg | 0.020510 kg | 0.020510 kg | 0.020510 kg | 0.020510 kg |
| Pyridoxine hydrochloride | 0.019750 kg | 0.019750 kg | 0.019750 kg | 0.019750 kg | 0.019750 kg |
| Riboflavin | 0.016000 kg | 0.016000 kg | 0.016000 kg | 0.016000 kg | 0.016000 kg |
| Folic acid | 0.002783 kg | 0.002783 kg | 0.002783 kg | 0.002783 kg | 0.002783 kg |
| Biotin | 0.002419 kg | 0.002419 kg | 0.002419 kg | 0.002419 kg | 0.002419 kg |
| Cyanocobalamin | 0.000055 kg | 0.000055 kg | 0.000055 kg | 0.000055 kg | 0.000055 kg |
| dl-alpha-tocopheryl acetate | 0.129600 kg | 0.129600 kg | 0.129600 kg | 0.129600 kg | 0.129600 kg |
| Phylloquinone | 0.002162 kg | 0.002162 kg | 0.002162 kg | 0.002162 kg | 0.002162 kg |
| Vitamin D3 | 0.000028 kg | 0.000028 kg | 0.000028 kg | 0.000028 kg | 0.000028 kg |
| Vitamin A palmitate | 0.010373 kg | 0.010373 kg | 0.010373 kg | 0.010373 kg | 0.010373 kg |
| Potassium iodide | 0.000440 kg | 0.000440 kg | 0.000440 kg | 0.000440 kg | 0.000440 kg |

| Ingredient | Ex. 6 | Ex. 7 | Ex. 8 | Ex. 9 | Ex. 10 |
|---|---|---|---|---|---|
| Corn syrup | 256.86 kg | 256.86 kg | 256.86 kg | 256.86 kg | 256.86 kg |
| Corn Maltodextrin | 216.25 kg | 216.25 kg | 216.25 kg | 216.25 kg | 216.25 kg |
| Sucrose | 177.95 kg | 177.95 kg | 177.95 kg | 177.95 kg | 177.95 kg |
| Corn oil | 155.40 kg | 155.40 kg | 155.40 kg | 155.40 kg | 155.40 kg |
| Casein | 132.97 kg | 132.97 kg | 132.97 kg | 132.97 kg | 132.97 kg |
| Soy protein isolate | 29.84 kg | 29.84 kg | 29.84 kg | 29.84 kg | 29.84 kg |
| Calcium caseinate | 19.46 kg | 19.46 kg | 19.46 kg | 19.46 kg | 19.46 kg |
| 20% potassium citrate | 16.09 kg | 16.09 kg | 16.09 kg | 16.09 kg | 16.09 kg |
| Vanilla | 14.55 kg | 14.55 kg | 14.55 kg | 14.55 kg | 14.55 kg |
| 20% sodium hydroxide | 13.77 kg | 13.77 kg | 13.77 kg | 13.77 kg | 13.77 kg |
| Human Milk Oligosaccharides | 0.08 kg | 0.40 kg | 0.80 kg | 4.00 kg | 40.00 kg |
| Galactooligosaccharides | 8 kg | 40 kg | 80 kg | 120 kg | 160 kg |
| Potassium citrate | 7.54 kg | 7.54 kg | 7.54 kg | 7.54 kg | 7.54 kg |
| Magnesium chloride | 7.53 kg | 7.53 kg | 7.53 kg | 7.53 kg | 7.53 kg |
| Tricalcium phosphate | 6.23 kg | 6.23 kg | 6.23 kg | 6.23 kg | 6.23 kg |
| Sodium citrate | 5.66 kg | 5.66 kg | 5.66 kg | 5.66 kg | 5.66 kg |
| Potassium chloride | 3.79 kg | 3.79 kg | 3.79 kg | 3.79 kg | 3.79 kg |
| Soy lecithin | 3.44 kg | 3.44 kg | 3.44 kg | 3.44 kg | 3.44 kg |
| Ascorbic acid | 1.91 kg | 1.91 kg | 1.91 kg | 1.91 kg | 1.91 kg |
| Choline chloride | 1.64 kg | 1.64 kg | 1.64 kg | 1.64 kg | 1.64 kg |
| 45% KOH | 1.26 kg | 1.26 kg | 1.26 kg | 1.26 kg | 1.26 kg |
| Zinc sulfate | 0.1558 kg | 0.1558 kg | 0.1558 kg | 0.1558 kg | 0.1558 kg |
| Ferrous sulfate | 0.121700 kg | 0.121700 kg | 0.121700 kg | 0.121700 kg | 0.121700 kg |
| Manganese sulfate | 0.036900 kg | 0.036900 kg | 0.036900 kg | 0.036900 kg | 0.036900 kg |
| Cupric sulfate | 0.021100 kg | 0.021100 kg | 0.021100 kg | 0.021100 kg | 0.021100 kg |
| Chromium chloride | 0.001280 kg | 0.001280 kg | 0.001280 kg | 0.001280 kg | 0.001280 kg |
| Sodium molybdate | 0.001012 kg | 0.001012 kg | 0.001012 kg | 0.001012 kg | 0.001012 kg |
| Sodium selenate | 0.000434 kg | 0.000434 kg | 0.000434 kg | 0.000434 kg | 0.000434 kg |
| Niacinamide | 0.124200 kg | 0.124200 kg | 0.124200 kg | 0.124200 kg | 0.124200 kg |
| D-calcium pantothenate | 0.083000 kg | 0.083000 kg | 0.083000 kg | 0.083000 kg | 0.083000 kg |
| Thiamine chloride hydrochloride | 0.020510 kg | 0.020510 kg | 0.020510 kg | 0.020510 kg | 0.020510 kg |
| Pyridoxine hydrochloride | 0.019750 kg | 0.019750 kg | 0.019750 kg | 0.019750 kg | 0.019750 kg |
| Riboflavin | 0.016000 kg | 0.016000 kg | 0.016000 kg | 0.016000 kg | 0.016000 kg |
| Folic acid | 0.002783 kg | 0.002783 kg | 0.002783 kg | 0.002783 kg | 0.002783 kg |
| Biotin | 0.002419 kg | 0.002419 kg | 0.002419 kg | 0.002419 kg | 0.002419 kg |
| Cyanocobalamin | 0.000055 kg | 0.000055 kg | 0.000055 kg | 0.000055 kg | 0.000055 kg |
| dl-alpha-tocopheryl acetate | 0.129600 kg | 0.129600 kg | 0.129600 kg | 0.129600 kg | 0.129600 kg |
| Phylloquinone | 0.002162 kg | 0.002162 kg | 0.002162 kg | 0.002162 kg | 0.002162 kg |
| Vitamin D3 | 0.000028 kg | 0.000028 kg | 0.000028 kg | 0.000028 kg | 0.000028 kg |
| Vitamin A palmitate | 0.010373 kg | 0.010373 kg | 0.010373 kg | 0.010373 kg | 0.010373 kg |
| Potassium iodide | 0.000440 kg | 0.000440 kg | 0.000440 kg | 0.000440 kg | 0.000440 kg |

| Ingredient | Ex. 11 | Ex. 12 | Ex. 13 | Ex. 14 | Ex. 15 |
|---|---|---|---|---|---|
| Corn syrup | 256.86 kg | 256.86 kg | 256.86 kg | 256.86 kg | 256.86 kg |
| Corn Maltodextrin | 216.25 kg | 216.25 kg | 216.25 kg | 216.25 kg | 216.25 kg |
| Sucrose | 177.95 kg | 177.95 kg | 177.95 kg | 177.95 kg | 177.95 kg |
| Corn oil | 155.40 kg | 155.40 kg | 155.40 kg | 155.40 kg | 155.40 kg |
| Casein | 132.97 kg | 132.97 kg | 132.97 kg | 132.97 kg | 132.97 kg |
| Soy protein isolate | 29.84 kg | 29.84 kg | 29.84 kg | 29.84 kg | 29.84 kg |
| Calcium caseinate | 19.46 kg | 19.46 kg | 19.46 kg | 19.46 kg | 19.46 kg |
| 20% potassium citrate | 16.09 kg | 16.09 kg | 16.09 kg | 16.09 kg | 16.09 kg |
| Vanilla | 14.55 kg | 14.55 kg | 14.55 kg | 14.55 kg | 14.55 kg |

-continued

| Ingredient | | | | | |
|---|---|---|---|---|---|
| 20% sodium hydroxide | 13.77 kg | 13.77 kg | 13.77 kg | 13.77 kg | 13.77 kg |
| 2'-FL | 0.08 kg | 0.40 kg | 0.80 kg | 4.00 kg | 40.00 kg |
| Potassium citrate | 7.54 kg | 7.54 kg | 7.54 kg | 7.54 kg | 7.54 kg |
| Magnesium chloride | 7.53 kg | 7.53 kg | 7.53 kg | 7.53 kg | 7.53 kg |
| Tricalcium phosphate | 6.23 kg | 6.23 kg | 6.23 kg | 6.23 kg | 6.23 kg |
| Sodium citrate | 5.66 kg | 5.66 kg | 5.66 kg | 5.66 kg | 5.66 kg |
| Potassium chloride | 3.79 kg | 3.79 kg | 3.79 kg | 3.79 kg | 3.79 kg |
| Soy lecithin | 3.44 kg | 3.44 kg | 3.44 kg | 3.44 kg | 3.44 kg |
| Ascorbic acid | 1.91 kg | 1.91 kg | 1.91 kg | 1.91 kg | 1.91 kg |
| Choline chloride | 1.64 kg | 1.64 kg | 1.64 kg | 1.64 kg | 1.64 kg |
| 45% KOH | 1.26 kg | 1.26 kg | 1.26 kg | 1.26 kg | 1.26 kg |
| Zinc sulfate | 0.1558 kg | 0.1558 kg | 0.1558 kg | 0.1558 kg | 0.1558 kg |
| Ferrous sulfate | 0.121700 kg | 0.121700 kg | 0.121700 kg | 0.121700 kg | 0.121700 kg |
| Manganese sulfate | 0.036900 kg | 0.036900 kg | 0.036900 kg | 0.036900 kg | 0.036900 kg |
| Cupric sulfate | 0.021100 kg | 0.021100 kg | 0.021100 kg | 0.021100 kg | 0.021100 kg |
| Chromium chloride | 0.001280 kg | 0.001280 kg | 0.001280 kg | 0.001280 kg | 0.001280 kg |
| Sodium molybdate | 0.001012 kg | 0.001012 kg | 0.001012 kg | 0.001012 kg | 0.001012 kg |
| Sodium selenate | 0.000434 kg | 0.000434 kg | 0.000434 kg | 0.000434 kg | 0.000434 kg |
| Niacinamide | 0.124200 kg | 0.124200 kg | 0.124200 kg | 0.124200 kg | 0.124200 kg |
| D-calcium pantothenate | 0.083000 kg | 0.083000 kg | 0.083000 kg | 0.083000 kg | 0.083000 kg |
| Thiamine chloride hydrochloride | 0.020510 kg | 0.020510 kg | 0.020510 kg | 0.020510 kg | 0.020510 kg |
| Pyridoxine hydrochloride | 0.019750 kg | 0.019750 kg | 0.019750 kg | 0.019750 kg | 0.019750 kg |
| Riboflavin | 0.016000 kg | 0.016000 kg | 0.016000 kg | 0.016000 kg | 0.016000 kg |
| Folic acid | 0.002783 kg | 0.002783 kg | 0.002783 kg | 0.002783 kg | 0.002783 kg |
| Biotin | 0.002419 kg | 0.002419 kg | 0.002419 kg | 0.002419 kg | 0.002419 kg |
| Cyanocobalamin | 0.000055 kg | 0.000055 kg | 0.000055 kg | 0.000055 kg | 0.000055 kg |
| dl-alpha-tocopheryl acetate | 0.129600 kg | 0.129600 kg | 0.129600 kg | 0.129600 kg | 0.129600 kg |
| Phylloquinone | 0.002162 kg | 0.002162 kg | 0.002162 kg | 0.002162 kg | 0.002162 kg |
| Vitamin D3 | 0.000028 kg | 0.000028 kg | 0.000028 kg | 0.000028 kg | 0.000028 kg |
| Vitamin A palmitate | 0.010373 kg | 0.010373 kg | 0.010373 kg | 0.010373 kg | 0.010373 kg |
| Potassium iodide | 0.000440 kg | 0.000440 kg | 0.000440 kg | 0.000440 kg | 0.000440 kg |

| Ingredient | Ex. 16 | Ex. 17 | Ex. 18 | Ex. 19 | Ex. 20 |
|---|---|---|---|---|---|
| Corn syrup | 256.86 kg | 256.86 kg | 256.86 kg | 256.86 kg | 256.86 kg |
| Corn Maltodextrin | 216.25 kg | 216.25 kg | 216.25 kg | 216.25 kg | 216.25 kg |
| Sucrose | 177.95 kg | 177.95 kg | 177.95 kg | 177.95 kg | 177.95 kg |
| Corn oil | 155.40 kg | 155.40 kg | 155.40 kg | 155.40 kg | 155.40 kg |
| Casein | 132.97 kg | 132.97 kg | 132.97 kg | 132.97 kg | 132.97 kg |
| Soy protein isolate | 29.84 kg | 29.84 kg | 29.84 kg | 29.84 kg | 29.84 kg |
| Calcium caseinate | 19.46 kg | 19.46 kg | 19.46 kg | 19.46 kg | 19.46 kg |
| 20% potassium citrate | 16.09 kg | 16.09 kg | 16.09 kg | 16.09 kg | 16.09 kg |
| Vanilla | 14.55 kg | 14.55 kg | 14.55 kg | 14.55 kg | 14.55 kg |
| 20% sodium hydroxide | 13.77 kg | 13.77 kg | 13.77 kg | 13.77 kg | 13.77 kg |
| 2'-FL | 0.08 kg | 0.40 kg | 0.80 kg | 4.00 kg | 40.00 kg |
| Galactooligosaccharides | 8 kg | 40 kg | 80 kg | 120 kg | 160 kg |
| Potassium citrate | 7.54 kg | 7.54 kg | 7.54 kg | 7.54 kg | 7.54 kg |
| Magnesium chloride | 7.53 kg | 7.53 kg | 7.53 kg | 7.53 kg | 7.53 kg |
| Tricalcium phosphate | 6.23 kg | 6.23 kg | 6.23 kg | 6.23 kg | 6.23 kg |
| Sodium citrate | 5.66 kg | 5.66 kg | 5.66 kg | 5.66 kg | 5.66 kg |
| Potassium chloride | 3.79 kg | 3.79 kg | 3.79 kg | 3.79 kg | 3.79 kg |
| Soy lecithin | 3.44 kg | 3.44 kg | 3.44 kg | 3.44 kg | 3.44 kg |
| Ascorbic acid | 1.91 kg | 1.91 kg | 1.91 kg | 1.91 kg | 1.91 kg |
| Choline chloride | 1.64 kg | 1.64 kg | 1.64 kg | 1.64 kg | 1.64 kg |
| 45% KOH | 1.26 kg | 1.26 kg | 1.26 kg | 1.26 kg | 1.26 kg |
| Zinc sulfate | 0.1558 kg | 0.1558 kg | 0.1558 kg | 0.1558 kg | 0.1558 kg |
| Ferrous sulfate | 0.121700 kg | 0.121700 kg | 0.121700 kg | 0.121700 kg | 0.121700 kg |
| Manganese sulfate | 0.036900 kg | 0.036900 kg | 0.036900 kg | 0.036900 kg | 0.036900 kg |
| Cupric sulfate | 0.021100 kg | 0.021100 kg | 0.021100 kg | 0.021100 kg | 0.021100 kg |
| Chromium chloride | 0.001280 kg | 0.001280 kg | 0.001280 kg | 0.001280 kg | 0.001280 kg |
| Sodium molybdate | 0.001012 kg | 0.001012 kg | 0.001012 kg | 0.001012 kg | 0.001012 kg |
| Sodium selenate | 0.000434 kg | 0.000434 kg | 0.000434 kg | 0.000434 kg | 0.000434 kg |
| Niacinamide | 0.124200 kg | 0.124200 kg | 0.124200 kg | 0.124200 kg | 0.124200 kg |
| D-calcium pantothenate | 0.083000 kg | 0.083000 kg | 0.083000 kg | 0.083000 kg | 0.083000 kg |
| Thiamine chloride hydrochloride | 0.020510 kg | 0.020510 kg | 0.020510 kg | 0.020510 kg | 0.020510 kg |
| Pyridoxine hydrochloride | 0.019750 kg | 0.019750 kg | 0.019750 kg | 0.019750 kg | 0.019750 kg |
| Riboflavin | 0.016000 kg | 0.016000 kg | 0.016000 kg | 0.016000 kg | 0.016000 kg |
| Folic acid | 0.002783 kg | 0.002783 kg | 0.002783 kg | 0.002783 kg | 0.002783 kg |
| Biotin | 0.002419 kg | 0.002419 kg | 0.002419 kg | 0.002419 kg | 0.002419 kg |
| Cyanocobalamin | 0.000055 kg | 0.000055 kg | 0.000055 kg | 0.000055 kg | 0.000055 kg |
| dl-alpha-tocopheryl acetate | 0.129600 kg | 0.129600 kg | 0.129600 kg | 0.129600 kg | 0.129600 kg |
| Phylloquinone | 0.002162 kg | 0.002162 kg | 0.002162 kg | 0.002162 kg | 0.002162 kg |
| Vitamin D3 | 0.000028 kg | 0.000028 kg | 0.000028 kg | 0.000028 kg | 0.000028 kg |
| Vitamin A palmitate | 0.010373 kg | 0.010373 kg | 0.010373 kg | 0.010373 kg | 0.010373 kg |
| Potassium iodide | 0.000440 kg | 0.000440 kg | 0.000440 kg | 0.000440 kg | 0.000440 kg |

AN = as needed

Examples 21-40

Examples 21-40 illustrate spray dried nutritional powders of the present disclosure, the ingredients of which are listed in the table below. All ingredient amounts are listed as kilogram per 1000 kilogram batch of product, unless otherwise specified.

| Ingredient | Ex. 21 | Ex. 22 | Ex. 23 | Ex. 24 | Ex. 25 |
|---|---|---|---|---|---|
| Skim milk | 695.30 kg | 695.30 kg | 695.30 kg | 695.30 kg | 695.30 kg |
| Lactose | 380.80 kg | 380.80 kg | 380.80 kg | 380.80 kg | 380.80 kg |
| High oleic safflower oil | 118.20 kg | 118.20 kg | 118.20 kg | 118.20 kg | 118.20 kg |
| Soy oil | 83.62 kg | 83.62 kg | 83.62 kg | 83.62 kg | 83.62 kg |
| Coconut oil | 82.52 kg | 82.52 kg | 82.52 kg | 82.52 kg | 82.52 kg |
| Human Milk Oligosaccharides | 0.08 kg | 0.40 kg | 0.80 kg | 4.00 kg | 40.00 kg |
| Whey protein concentrate | 50.89 kg | 50.89 kg | 50.89 kg | 50.89 kg | 50.89 kg |
| Potassium citrate | 8.93 kg | 8.93 kg | 8.93 kg | 8.93 kg | 8.93 kg |
| Calcium carbonate | 4.38 kg | 4.38 kg | 4.38 kg | 4.38 kg | 4.38 kg |
| ARA oil | 2.86 kg | 2.86 kg | 2.86 kg | 2.86 kg | 2.86 kg |
| Nucleotide-choline premix | 2.40 kg | 2.40 kg | 2.40 kg | 2.40 kg | 2.40 kg |
| Ascorbic acid | 1.28 kg | 1.28 kg | 1.28 kg | 1.28 kg | 1.28 kg |
| Potassium chloride | 1.24 kg | 1.24 kg | 1.24 kg | 1.24 kg | 1.24 kg |
| Soy lecithin | 1.12 kg | 1.12 kg | 1.12 kg | 1.12 kg | 1.12 kg |
| Vitamin/mineral/taurine premix | 1.12 kg | 1.12 kg | 1.12 kg | 1.12 kg | 1.12 kg |
| DHA oil | 1.07 kg | 1.07 kg | 1.07 kg | 1.07 kg | 1.07 kg |
| Magnesium chloride | 948.50 g | 948.50 g | 948.50 g | 948.50 g | 948.50 g |
| Vitamin A, D, E, K1 | 518.40 g | 518.40 g | 518.40 g | 518.40 g | 518.40 g |
| Ferrous sulfate | 472.40 g | 472.40 g | 472.40 g | 472.40 g | 472.40 g |
| Choline chloride | 432.10 g | 432.10 g | 432.10 g | 432.10 g | 432.10 g |
| Ascorbyl palmitate | 364.90 g | 364.90 g | 364.90 g | 364.90 g | 364.90 g |
| Sodium chloride | 347.50 g | 347.50 g | 347.50 g | 347.50 g | 347.50 g |
| Carotenoid premix | 187.4 g | 187.4 g | 187.4 g | 187.4 g | 187.4 g |
| Mixed tocopherols | 161.20 g | 161.20 g | 161.20 g | 161.20 g | 161.20 g |
| L-carnitine | 26.30 g | 26.30 g | 26.30 g | 26.30 g | 26.30 g |
| Riboflavin | 3.18 g | 3.18 g | 3.18 g | 3.18 g | 3.18 g |
| Tricalcium phosphate | AN | AN | AN | AN | AN |
| Potassium phosphate monobasic | AN | AN | AN | AN | AN |
| Potassium hydroxide | AN | AN | AN | AN | AN |

| Ingredient | Ex. 26 | Ex. 27 | Ex. 28 | Ex. 29 | Ex. 30 |
|---|---|---|---|---|---|
| Skim milk | 695.30 kg | 695.30 kg | 695.30 kg | 695.30 kg | 695.30 kg |
| Lactose | 380.80 kg | 380.80 kg | 380.80 kg | 380.80 kg | 380.80 kg |
| High oleic safflower oil | 118.20 kg | 118.20 kg | 118.20 kg | 118.20 kg | 118.20 kg |
| Soy oil | 83.62 kg | 83.62 kg | 83.62 kg | 83.62 kg | 83.62 kg |
| Coconut oil | 82.52 kg | 82.52 kg | 82.52 kg | 82.52 kg | 82.52 kg |
| Human Milk Oligosaccharides | 0.08 kg | 0.40 kg | 0.80 kg | 4.00 kg | 40.00 kg |
| Galactooligosaccharides | 8 kg | 40 kg | 80 kg | 120 kg | 160 kg |
| Whey protein concentrate | 50.89 kg | 50.89 kg | 50.89 kg | 50.89 kg | 50.89 kg |
| Potassium citrate | 8.93 kg | 8.93 kg | 8.93 kg | 8.93 kg | 8.93 kg |
| Calcium carbonate | 4.38 kg | 4.38 kg | 4.38 kg | 4.38 kg | 4.38 kg |
| ARA oil | 2.86 kg | 2.86 kg | 2.86 kg | 2.86 kg | 2.86 kg |
| Nucleotide-choline premix | 2.40 kg | 2.40 kg | 2.40 kg | 2.40 kg | 2.40 kg |
| Ascorbic acid | 1.28 kg | 1.28 kg | 1.28 kg | 1.28 kg | 1.28 kg |
| Potassium chloride | 1.24 kg | 1.24 kg | 1.24 kg | 1.24 kg | 1.24 kg |
| Soy lecithin | 1.12 kg | 1.12 kg | 1.12 kg | 1.12 kg | 1.12 kg |
| Vitamin/mineral/taurine premix | 1.12 kg | 1.12 kg | 1.12 kg | 1.12 kg | 1.12 kg |
| DHA oil | 1.07 kg | 1.07 kg | 1.07 kg | 1.07 kg | 1.07 kg |
| Magnesium chloride | 948.50 g | 948.50 g | 948.50 g | 948.50 g | 948.50 g |
| Vitamin A, D, E, K1 | 518.40 g | 518.40 g | 518.40 g | 518.40 g | 518.40 g |
| Ferrous sulfate | 472.40 g | 472.40 g | 472.40 g | 472.40 g | 472.40 g |
| Choline chloride | 432.10 g | 432.10 g | 432.10 g | 432.10 g | 432.10 g |
| Ascorbyl palmitate | 364.90 g | 364.90 g | 364.90 g | 364.90 g | 364.90 g |
| Sodium chloride | 347.50 g | 347.50 g | 347.50 g | 347.50 g | 347.50 g |
| Carotenoid premix | 187.4 g | 187.4 g | 187.4 g | 187.4 g | 187.4 g |
| Mixed tocopherols | 161.20 g | 161.20 g | 161.20 g | 161.20 g | 161.20 g |
| L-carnitine | 26.30 g | 26.30 g | 26.30 g | 26.30 g | 26.30 g |
| Riboflavin | 3.18 g | 3.18 g | 3.18 g | 3.18 g | 3.18 g |
| Tricalcium phosphate | AN | AN | AN | AN | AN |
| Potassium phosphate monobasic | AN | AN | AN | AN | AN |
| Potassium hydroxide | AN | AN | AN | AN | AN |

| Ingredient | Ex. 31 | Ex. 32 | Ex. 33 | Ex. 34 | Ex. 35 |
|---|---|---|---|---|---|
| Skim milk | 695.30 kg | 695.30 kg | 695.30 kg | 695.30 kg | 695.30 kg |
| Lactose | 380.80 kg | 380.80 kg | 380.80 kg | 380.80 kg | 380.80 kg |
| High oleic safflower oil | 118.20 kg | 118.20 kg | 118.20 kg | 118.20 kg | 118.20 kg |
| Soy oil | 83.62 kg | 83.62 kg | 83.62 kg | 83.62 kg | 83.62 kg |
| Coconut oil | 82.52 kg | 82.52 kg | 82.52 kg | 82.52 kg | 82.52 kg |

-continued

| Ingredient | | | | | |
|---|---|---|---|---|---|
| 2'-FL | 0.08 kg | 0.40 kg | 0.80 kg | 4.00 kg | 40.00 kg |
| Whey protein concentrate | 50.89 kg | 50.89 kg | 50.89 kg | 50.89 kg | 50.89 kg |
| Potassium citrate | 8.93 kg | 8.93 kg | 8.93 kg | 8.93 kg | 8.93 kg |
| Calcium carbonate | 4.38 kg | 4.38 kg | 4.38 kg | 4.38 kg | 4.38 kg |
| ARA oil | 2.86 kg | 2.86 kg | 2.86 kg | 2.86 kg | 2.86 kg |
| Nucleotide-choline premix | 2.40 kg | 2.40 kg | 2.40 kg | 2.40 kg | 2.40 kg |
| Ascorbic acid | 1.28 kg | 1.28 kg | 1.28 kg | 1.28 kg | 1.28 kg |
| Potassium chloride | 1.24 kg | 1.24 kg | 1.24 kg | 1.24 kg | 1.24 kg |
| Soy lecithin | 1.12 kg | 1.12 kg | 1.12 kg | 1.12 kg | 1.12 kg |
| Vitamin/mineral/taurine premix | 1.12 kg | 1.12 kg | 1.12 kg | 1.12 kg | 1.12 kg |
| DHA oil | 1.07 kg | 1.07 kg | 1.07 kg | 1.07 kg | 1.07 kg |
| Magnesium chloride | 948.50 g | 948.50 g | 948.50 g | 948.50 g | 948.50 g |
| Vitamin A, D, E, K1 | 518.40 g | 518.40 g | 518.40 g | 518.40 g | 518.40 g |
| Ferrous sulfate | 472.40 g | 472.40 g | 472.40 g | 472.40 g | 472.40 g |
| Choline chloride | 432.10 g | 432.10 g | 432.10 g | 432.10 g | 432.10 g |
| Ascorbyl palmitate | 364.90 g | 364.90 g | 364.90 g | 364.90 g | 364.90 g |
| Sodium chloride | 347.50 g | 347.50 g | 347.50 g | 347.50 g | 347.50 g |
| Carotenoid premix | 187.4 g | 187.4 g | 187.4 g | 187.4 g | 187.4 g |
| Mixed tocopherols | 161.20 g | 161.20 g | 161.20 g | 161.20 g | 161.20 g |
| L-carnitine | 26.30 g | 26.30 g | 26.30 g | 26.30 g | 26.30 g |
| Riboflavin | 3.18 g | 3.18 g | 3.18 g | 3.18 g | 3.18 g |
| Tricalcium phosphate | AN | AN | AN | AN | AN |
| Potassium phosphate monobasic | AN | AN | AN | AN | AN |
| Potassium hydroxide | AN | AN | AN | AN | AN |

| Ingredient | Ex. 36 | Ex. 37 | Ex. 38 | Ex. 39 | Ex. 40 |
|---|---|---|---|---|---|
| Skim milk | 695.30 kg | 695.30 kg | 695.30 kg | 695.30 kg | 695.30 kg |
| Lactose | 380.80 kg | 380.80 kg | 380.80 kg | 380.80 kg | 380.80 kg |
| High oleic safflower oil | 118.20 kg | 118.20 kg | 118.20 kg | 118.20 kg | 118.20 kg |
| Soy oil | 83.62 kg | 83.62 kg | 83.62 kg | 83.62 kg | 83.62 kg |
| Coconut oil | 82.52 kg | 82.52 kg | 82.52 kg | 82.52 kg | 82.52 kg |
| 2'-FL | 0.08 kg | 0.40 kg | 0.80 kg | 4.00 kg | 40.00 kg |
| Galactooligosaccharides | 8 kg | 40 kg | 80 kg | 120 kg | 160 kg |
| Whey protein concentrate | 50.89 kg | 50.89 kg | 50.89 kg | 50.89 kg | 50.89 kg |
| Potassium citrate | 8.93 kg | 8.93 kg | 8.93 kg | 8.93 kg | 8.93 kg |
| Calcium carbonate | 4.38 kg | 4.38 kg | 4.38 kg | 4.38 kg | 4.38 kg |
| ARA oil | 2.86 kg | 2.86 kg | 2.86 kg | 2.86 kg | 2.86 kg |
| Nucleotide-choline premix | 2.40 kg | 2.40 kg | 2.40 kg | 2.40 kg | 2.40 kg |
| Ascorbic acid | 1.28 kg | 1.28 kg | 1.28 kg | 1.28 kg | 1.28 kg |
| Potassium chloride | 1.24 kg | 1.24 kg | 1.24 kg | 1.24 kg | 1.24 kg |
| Soy lecithin | 1.12 kg | 1.12 kg | 1.12 kg | 1.12 kg | 1.12 kg |
| Vitamin/mineral/taurine premix | 1.12 kg | 1.12 kg | 1.12 kg | 1.12 kg | 1.12 kg |
| DHA oil | 1.07 kg | 1.07 kg | 1.07 kg | 1.07 kg | 1.07 kg |
| Magnesium chloride | 948.50 g | 948.50 g | 948.50 g | 948.50 g | 948.50 g |
| Vitamin A, D, E, K1 | 518.40 g | 518.40 g | 518.40 g | 518.40 g | 518.40 g |
| Ferrous sulfate | 472.40 g | 472.40 g | 472.40 g | 472.40 g | 472.40 g |
| Choline chloride | 432.10 g | 432.10 g | 432.10 g | 432.10 g | 432.10 g |
| Ascorbyl palmitate | 364.90 g | 364.90 g | 364.90 g | 364.90 g | 364.90 g |
| Sodium chloride | 347.50 g | 347.50 g | 347.50 g | 347.50 g | 347.50 g |
| Carotenoid premix | 187.4 g | 187.4 g | 187.4 g | 187.4 g | 187.4 g |
| Mixed tocopherols | 161.20 g | 161.20 g | 161.20 g | 161.20 g | 161.20 g |
| L-carnitine | 26.30 g | 26.30 g | 26.30 g | 26.30 g | 26.30 g |
| Riboflavin | 3.18 g | 3.18 g | 3.18 g | 3.18 g | 3.18 g |
| Tricalcium phosphate | AN | AN | AN | AN | AN |
| Potassium phosphate monobasic | AN | AN | AN | AN | AN |
| Potassium hydroxide | AN | AN | AN | AN | AN |

AN = as needed

Examples 41-60

Examples 41-60 illustrate liquid emulsions of the present disclosure, the ingredients of which are listed in the table below. All ingredient amounts are listed as kilogram per 1000 kilogram batch of product, unless otherwise specified.

| Ingredient | Ex. 41 | Ex. 42 | Ex. 43 | Ex. 44 | Ex. 45 |
|---|---|---|---|---|---|
| Water | 793.7 kg | 793.7 kg | 793.7 kg | 793.7 kg | 793.7 kg |
| Nonfat milk | 97.50 kg | 97.50 kg | 97.50 kg | 97.50 kg | 97.50 kg |
| Corn syrup solids | 31.90 kg | 31.90 kg | 31.90 kg | 31.90 kg | 31.90 kg |
| Medium chain triglycerides | 17.20 kg | 17.20 kg | 17.20 kg | 17.20 kg | 17.20 kg |
| Lactose | 16.45 kg | 16.45 kg | 16.45 kg | 16.45 kg | 16.45 kg |
| Whey protein concentrate | 12.69 kg | 12.69 kg | 12.69 kg | 12.69 kg | 12.69 kg |
| Human Milk Oligosaccharides | 0.01 kg | 0.05 kg | 0.10 kg | 0.50 kg | 5.00 kg |

-continued

| Ingredient | | | | | |
|---|---|---|---|---|---|
| Soy oil | 10.30 kg | 10.30 kg | 10.30 kg | 10.30 kg | 10.30 kg |
| Coconut oil | 6.30 kg | 6.30 kg | 6.30 kg | 6.30 kg | 6.30 kg |
| 5% KOH | 4.86 kg | 4.86 kg | 4.86 kg | 4.86 kg | 4.86 kg |
| Tricalcium phosphate | 2.56 kg | 2.56 kg | 2.56 kg | 2.56 kg | 2.56 kg |
| Vitamin/mineral/taurine premix | 1.12 kg | 1.12 kg | 1.12 kg | 1.12 kg | 1.12 kg |
| Magnesium chloride | 405.00 g | 405.00 g | 405.00 g | 405.00 g | 405.00 g |
| Soy lecithin | 364.00 g | 364.00 g | 364.00 g | 364.00 g | 364.00 g |
| Monoglycerides | 364.00 g | 364.00 g | 364.00 g | 364.00 g | 364.00 g |
| AA fungal oil | 364.00 g | 364.00 g | 364.00 g | 364.00 g | 364.00 g |
| Potassium citrate | 340.00 g | 340.00 g | 340.00 g | 340.00 g | 340.00 g |
| Carrageenan | 300.00 g | 300.00 g | 300.00 g | 300.00 g | 300.00 g |
| Nucleotide-choline premix | 293.00 g | 293.00 g | 293.00 g | 293.00 g | 293.00 g |
| Sodium citrate | 250.00 g | 250.00 g | 250.00 g | 250.00 g | 250.00 g |
| DHA oil | 230.00 g | 230.00 g | 230.00 g | 230.00 g | 230.00 g |
| Potassium chloride | 138.00 g | 138.00 g | 138.00 g | 138.00 g | 138.00 g |
| Calcium carbonate | 101.00 g | 101.00 g | 101.00 g | 101.00 g | 101.00 g |
| Magnesium chloride | 948.50 g | 948.50 g | 948.50 g | 948.50 g | 948.50 g |
| Mixed Carotenoid Suspension | 110.23 g | 110.23 g | 110.23 g | 110.23 g | 110.23 g |
| Vitamin A, D3, E, K1 | 82.60 g | 82.60 g | 82.60 g | 82.60 g | 82.60 g |
| Choline chloride | 35.48 g | 35.48 g | 35.48 g | 35.48 g | 35.48 g |
| L-carnitine | 30.7 g | 30.7 g | 30.7 g | 30.7 g | 30.7 g |
| Vitamin A palmitate | 313.00 mg | 313.00 mg | 313.00 mg | 313.00 mg | 313.00 mg |
| Sodium chloride | AN | AN | AN | AN | AN |
| Potassium phosphate | AN | AN | AN | AN | AN |

| Ingredient | Ex. 46 | Ex. 47 | Ex. 48 | Ex. 49 | Ex. 50 |
|---|---|---|---|---|---|
| Water | 793.7 kg | 793.7 kg | 793.7 kg | 793.7 kg | 793.7 kg |
| Nonfat milk | 97.50 kg | 97.50 kg | 97.50 kg | 97.50 kg | 97.50 kg |
| Corn syrup solids | 31.90 kg | 31.90 kg | 31.90 kg | 31.90 kg | 31.90 kg |
| Medium chain triglycerides | 17.20 kg | 17.20 kg | 17.20 kg | 17.20 kg | 17.20 kg |
| Lactose | 16.45 kg | 16.45 kg | 16.45 kg | 16.45 kg | 16.45 kg |
| Whey protein concentrate | 12.69 kg | 12.69 kg | 12.69 kg | 12.69 kg | 12.69 kg |
| Human Milk Oligosaccharides | 0.01 kg | 0.05 kg | 0.10 kg | 0.50 kg | 5.00 kg |
| Galactooligosaccharides | 1 kg | 5 kg | 10 kg | 15 kg | 20 kg |
| Soy oil | 10.30 kg | 10.30 kg | 10.30 kg | 10.30 kg | 10.30 kg |
| Coconut oil | 6.30 kg | 6.30 kg | 6.30 kg | 6.30 kg | 6.30 kg |
| 5% KOH | 4.86 kg | 4.86 kg | 4.86 kg | 4.86 kg | 4.86 kg |
| Tricalcium phosphate | 2.56 kg | 2.56 kg | 2.56 kg | 2.56 kg | 2.56 kg |
| Vitamin/mineral/taurine premix | 1.12 kg | 1.12 kg | 1.12 kg | 1.12 kg | 1.12 kg |
| Magnesium chloride | 405.00 g | 405.00 g | 405.00 g | 405.00 g | 405.00 g |
| Soy lecithin | 364.00 g | 364.00 g | 364.00 g | 364.00 g | 364.00 g |
| Monoglycerides | 364.00 g | 364.00 g | 364.00 g | 364.00 g | 364.00 g |
| AA fungal oil | 364.00 g | 364.00 g | 364.00 g | 364.00 g | 364.00 g |
| Potassium citrate | 340.00 g | 340.00 g | 340.00 g | 340.00 g | 340.00 g |
| Carrageenan | 300.00 g | 300.00 g | 300.00 g | 300.00 g | 300.00 g |
| Nucleotide-choline premix | 293.00 g | 293.00 g | 293.00 g | 293.00 g | 293.00 g |
| Sodium citrate | 250.00 g | 250.00 g | 250.00 g | 250.00 g | 250.00 g |
| DHA oil | 230.00 g | 230.00 g | 230.00 g | 230.00 g | 230.00 g |
| Potassium chloride | 138.00 g | 138.00 g | 138.00 g | 138.00 g | 138.00 g |
| Calcium carbonate | 101.00 g | 101.00 g | 101.00 g | 101.00 g | 101.00 g |
| Magnesium chloride | 948.50 g | 948.50 g | 948.50 g | 948.50 g | 948.50 g |
| Mixed Carotenoid Suspension | 110.23 g | 110.23 g | 110.23 g | 110.23 g | 110.23 g |
| Vitamin A, D3, E, K1 | 82.60 g | 82.60 g | 82.60 g | 82.60 g | 82.60 g |
| Choline chloride | 35.48 g | 35.48 g | 35.48 g | 35.48 g | 35.48 g |
| L-carnitine | 30.7 g | 30.7 g | 30.7 g | 30.7 g | 30.7 g |
| Vitamin A palmitate | 313.00 mg | 313.00 mg | 313.00 mg | 313.00 mg | 313.00 mg |
| Sodium chloride | AN | AN | AN | AN | AN |
| Potassium phosphate | AN | AN | AN | AN | AN |

| Ingredient | Ex. 51 | Ex. 52 | Ex. 53 | Ex. 54 | Ex. 55 |
|---|---|---|---|---|---|
| Water | 793.7 kg | 793.7 kg | 793.7 kg | 793.7 kg | 793.7 kg |
| Nonfat milk | 97.50 kg | 97.50 kg | 97.50 kg | 97.50 kg | 97.50 kg |
| Corn syrup solids | 31.90 kg | 31.90 kg | 31.90 kg | 31.90 kg | 31.90 kg |
| Medium chain triglycerides | 17.20 kg | 17.20 kg | 17.20 kg | 17.20 kg | 17.20 kg |
| Lactose | 16.45 kg | 16.45 kg | 16.45 kg | 16.45 kg | 16.45 kg |
| Whey protein concentrate | 12.69 kg | 12.69 kg | 12.69 kg | 12.69 kg | 12.69 kg |
| 2'-FL | 0.01 kg | 0.05 kg | 0.10 kg | 0.50 kg | 5.00 kg |
| Soy oil | 10.30 kg | 10.30 kg | 10.30 kg | 10.30 kg | 10.30 kg |
| Coconut oil | 6.30 kg | 6.30 kg | 6.30 kg | 6.30 kg | 6.30 kg |
| 5% KOH | 4.86 kg | 4.86 kg | 4.86 kg | 4.86 kg | 4.86 kg |
| Tricalcium phosphate | 2.56 kg | 2.56 kg | 2.56 kg | 2.56 kg | 2.56 kg |
| Vitamin/mineral/taurine premix | 1.12 kg | 1.12 kg | 1.12 kg | 1.12 kg | 1.12 kg |
| Magnesium chloride | 405.00 g | 405.00 g | 405.00 g | 405.00 g | 405.00 g |
| Soy lecithin | 364.00 g | 364.00 g | 364.00 g | 364.00 g | 364.00 g |
| Monoglycerides | 364.00 g | 364.00 g | 364.00 g | 364.00 g | 364.00 g |
| AA fungal oil | 364.00 g | 364.00 g | 364.00 g | 364.00 g | 364.00 g |
| Potassium citrate | 340.00 g | 340.00 g | 340.00 g | 340.00 g | 340.00 g |

| Ingredient | | | | | |
|---|---|---|---|---|---|
| Carrageenan | 300.00 g | 300.00 g | 300.00 g | 300.00 g | 300.00 g |
| Nucleotide-choline premix | 293.00 g | 293.00 g | 293.00 g | 293.00 g | 293.00 g |
| Sodium citrate | 250.00 g | 250.00 g | 250.00 g | 250.00 g | 250.00 g |
| DHA oil | 230.00 g | 230.00 g | 230.00 g | 230.00 g | 230.00 g |
| Potassium chloride | 138.00 g | 138.00 g | 138.00 g | 138.00 g | 138.00 g |
| Calcium carbonate | 101.00 g | 101.00 g | 101.00 g | 101.00 g | 101.00 g |
| Magnesium chloride | 948.50 g | 948.50 g | 948.50 g | 948.50 g | 948.50 g |
| Mixed Carotenoid Suspension | 110.23 g | 110.23 g | 110.23 g | 110.23 g | 110.23 g |
| Vitamin A, D3, E, K1 | 82.60 g | 82.60 g | 82.60 g | 82.60 g | 82.60 g |
| Choline chloride | 35.48 g | 35.48 g | 35.48 g | 35.48 g | 35.48 g |
| L-carnitine | 30.7 g | 30.7 g | 30.7 g | 30.7 g | 30.7 g |
| Vitamin A palmitate | 313.00 mg | 313.00 mg | 313.00 mg | 313.00 mg | 313.00 mg |
| Sodium chloride | AN | AN | AN | AN | AN |
| Potassium phosphate | AN | AN | AN | AN | AN |

| Ingredient | Ex. 56 | Ex. 57 | Ex. 58 | Ex. 59 | Ex. 60 |
|---|---|---|---|---|---|
| Water | 793.7 kg | 793.7 kg | 793.7 kg | 793.7 kg | 793.7 kg |
| Nonfat milk | 97.50 kg | 97.50 kg | 97.50 kg | 97.50 kg | 97.50 kg |
| Corn syrup solids | 31.90 kg | 31.90 kg | 31.90 kg | 31.90 kg | 31.90 kg |
| Medium chain triglycerides | 17.20 kg | 17.20 kg | 17.20 kg | 17.20 kg | 17.20 kg |
| Lactose | 16.45 kg | 16.45 kg | 16.45 kg | 16.45 kg | 16.45 kg |
| Whey protein concentrate | 12.69 kg | 12.69 kg | 12.69 kg | 12.69 kg | 12.69 kg |
| 2'-FL | 0.01 kg | 0.05 kg | 0.10 kg | 0.50 kg | 5.00 kg |
| Galactooligosaccharides | 1 kg | 5 kg | 10 kg | 15 kg | 20 kg |
| Soy oil | 10.30 kg | 10.30 kg | 10.30 kg | 10.30 kg | 10.30 kg |
| Coconut oil | 6.30 kg | 6.30 kg | 6.30 kg | 6.30 kg | 6.30 kg |
| 5% KOH | 4.86 kg | 4.86 kg | 4.86 kg | 4.86 kg | 4.86 kg |
| Tricalcium phosphate | 2.56 kg | 2.56 kg | 2.56 kg | 2.56 kg | 2.56 kg |
| Vitamin/mineral/taurine premix | 1.12 kg | 1.12 kg | 1.12 kg | 1.12 kg | 1.12 kg |
| Magnesium chloride | 405.00 g | 405.00 g | 405.00 g | 405.00 g | 405.00 g |
| Soy lecithin | 364.00 g | 364.00 g | 364.00 g | 364.00 g | 364.00 g |
| Monoglycerides | 364.00 g | 364.00 g | 364.00 g | 364.00 g | 364.00 g |
| AA fungal oil | 364.00 g | 364.00 g | 364.00 g | 364.00 g | 364.00 g |
| Potassium citrate | 340.00 g | 340.00 g | 340.00 g | 340.00 g | 340.00 g |
| Carrageenan | 300.00 g | 300.00 g | 300.00 g | 300.00 g | 300.00 g |
| Nucleotide-choline premix | 293.00 g | 293.00 g | 293.00 g | 293.00 g | 293.00 g |
| Sodium citrate | 250.00 g | 250.00 g | 250.00 g | 250.00 g | 250.00 g |
| DHA oil | 230.00 g | 230.00 g | 230.00 g | 230.00 g | 230.00 g |
| Potassium chloride | 138.00 g | 138.00 g | 138.00 g | 138.00 g | 138.00 g |
| Calcium carbonate | 101.00 g | 101.00 g | 101.00 g | 101.00 g | 101.00 g |
| Magnesium chloride | 948.50 g | 948.50 g | 948.50 g | 948.50 g | 948.50 g |
| Mixed Carotenoid Suspension | 110.23 g | 110.23 g | 110.23 g | 110.23 g | 110.23 g |
| Vitamin A, D3, E, K1 | 82.60 g | 82.60 g | 82.60 g | 82.60 g | 82.60 g |
| Choline chloride | 35.48 g | 35.48 g | 35.48 g | 35.48 g | 35.48 g |
| L-carnitine | 30.7 g | 30.7 g | 30.7 g | 30.7 g | 30.7 g |
| Vitamin A palmitate | 313.00 mg | 313.00 mg | 313.00 mg | 313.00 mg | 313.00 mg |
| Sodium chloride | AN | AN | AN | AN | AN |
| Potassium phosphate | AN | AN | AN | AN | AN |

AN = as needed

Examples 61-76

Examples 61-76 illustrate concentrated liquid human milk fortifiers of the present disclosure, the ingredients of which are listed in the table below. All ingredient amounts are listed as kilogram or pound per 18,000 pounds batch of product, unless otherwise specified.

| Ingredient (Per 18,000 pounds) | Ex. 61 | Ex. 62 | Ex. 63 | Ex. 64 |
|---|---|---|---|---|
| Nonfat milk solids | 7220.00 lbs | 7220.00 lbs | 7220.00 lbs | 7220.00 lbs |
| Corn syrup solids | 2870.00 lbs | 2870.00 lbs | 2870.00 lbs | 2870.00 lbs |
| Medium chain triglycerides | 1760.00 lbs | 1760.00 lbs | 1760.00 lbs | 1760.00 lbs |
| Whey protein concentrate | 3410.00 lbs | 3410.00 lbs | 3410.00 lbs | 3410.00 lbs |
| Tricalcium phosphate | 701.00 kg | 701.00 kg | 701.00 kg | 701.00 kg |
| Human Milk Oligosaccharides | 1.64 kg | 16.4 kg | 82 kg | 164 kg |
| Potassium citrate tribasic | 224.00 kg | 224.00 kg | 224.00 kg | 224.00 kg |
| Ascorbic acid | 136.00 kg | 136.00 kg | 136.00 kg | 136.00 kg |
| Magnesium chloride | 117.00 kg | 117.00 kg | 117.00 kg | 117.00 kg |
| Sodium chloride | 4.71 kg | 4.71 kg | 4.71 kg | 4.71 kg |
| m-Inositol | 11.00 kg | 11.00 kg | 11.00 kg | 11.00 kg |
| Sodium citrate tribasic | 23.90 kg | 23.90 kg | 23.90 kg | 23.90 kg |
| Ferrous sulfate | 4.00 kg | 4.00 kg | 4.00 kg | 4.00 kg |

-continued

| Ingredient | | | | |
|---|---|---|---|---|
| Soy lecithin | 16.80 kg | 16.80 kg | 16.80 kg | 16.80 kg |
| Zinc sulfate | 11.1 kg | 11.1 kg | 11.1 kg | 11.1 kg |
| Vitamin E acetate | 7.60 kg | 7.60 kg | 7.60 kg | 7.60 kg |
| Vitamin A palmitate | 2.40 kg | 2.40 kg | 2.40 kg | 2.40 kg |
| Niacinamide | 9.80 kg | 9.80 kg | 9.80 kg | 9.80 kg |
| Riboflavin | 1.1 kg | 1.1 kg | 1.1 kg | 1.1 kg |
| Calcium pantothenate | 4.40 kg | 4.40 kg | 4.40 kg | 4.40 kg |
| Cupric sulfate | 1.800 kg | 1.800 kg | 1.800 kg | 1.800 kg |
| Thiamine hydrochloride | 776.00 g | 776.00 g | 776.00 g | 776.00 g |
| Pyridoxine hydrochloride | 665.00 g | 665.00 g | 665.00 g | 665.00 g |
| Vitamin D3 | 359.00 g | 359.00 g | 359.00 g | 359.00 g |
| Biotin | 82.00 g | 82.00 g | 82.00 g | 82.00 g |
| Folic acid | 77.00 g | 77.00 g | 77.00 g | 77.00 g |
| Cyanocobalamin | 2.00 g | 2.00 g | 2.00 g | 2.00 g |
| Phylloquinone | 27.00 g | 27.00 g | 27.00 g | 27.00 g |
| Manganese sulfate | 51.00 g | 51.00 g | 51.00 g | 51.00 g |
| Sodium selenate | 1.10 g | 1.10 g | 1.10 g | 1.10 g |
| Calcium carbonate | 0-4 kg | 0-4 kg | 0-4 kg | 0-4 kg |
| Potassium phosphate monobasic | 0-32 kg | 0-32 kg | 0-32 kg | 0-32 kg |
| Potassium hydroxide | 24.00 kg | 24.00 kg | 24.00 kg | 24.00 kg |

| Ingredient (Per 18,000 pounds) | Ex. 65 | Ex. 66 | Ex. 67 | Ex. 68 |
|---|---|---|---|---|
| Nonfat milk solids | 7220.00 lbs | 7220.00 lbs | 7220.00 lbs | 7220.00 lbs |
| Corn syrup solids | 2870.00 lbs | 2870.00 lbs | 2870.00 lbs | 2870.00 lbs |
| Medium chain triglycerides | 1760.00 lbs | 1760.00 lbs | 1760.00 lbs | 1760.00 lbs |
| Whey protein concentrate | 3410.00 lbs | 3410.00 lbs | 3410.00 lbs | 3410.00 lbs |
| Tricalcium phosphate | 701.00 kg | 701.00 kg | 701.00 kg | 701.00 kg |
| Human Milk Oligosaccharides | 1.64 kg | 16.4 kg | 82 kg | 164 kg |
| Galactooligosaccharides | 164 kg | 350 kg | 650 kg | 818 kg |
| Potassium citrate tribasic | 224.00 kg | 224.00 kg | 224.00 kg | 224.00 kg |
| Ascorbic acid | 136.00 kg | 136.00 kg | 136.00 kg | 136.00 kg |
| Magnesium chloride | 117.00 kg | 117.00 kg | 117.00 kg | 117.00 kg |
| Sodium chloride | 4.71 kg | 4.71 kg | 4.71 kg | 4.71 kg |
| m-Inositol | 11.00 kg | 11.00 kg | 11.00 kg | 11.00 kg |
| Sodium citrate tribasic | 23.90 kg | 23.90 kg | 23.90 kg | 23.90 kg |
| Ferrous sulfate | 4.00 kg | 4.00 kg | 4.00 kg | 4.00 kg |
| Soy lecithin | 16.80 kg | 16.80 kg | 16.80 kg | 16.80 kg |
| Zinc sulfate | 11.1 kg | 11.1 kg | 11.1 kg | 11.1 kg |
| Vitamin E acetate | 7.60 kg | 7.60 kg | 7.60 kg | 7.60 kg |
| Vitamin A palmitate | 2.40 kg | 2.40 kg | 2.40 kg | 2.40 kg |
| Niacinamide | 9.80 kg | 9.80 kg | 9.80 kg | 9.80 kg |
| Riboflavin | 1.1 kg | 1.1 kg | 1.1 kg | 1.1 kg |
| Calcium pantothenate | 4.40 kg | 4.40 kg | 4.40 kg | 4.40 kg |
| Cupric sulfate | 1.800 kg | 1.800 kg | 1.800 kg | 1.800 kg |
| Thiamine hydrochloride | 776.00 g | 776.00 g | 776.00 g | 776.00 g |
| Pyridoxine hydrochloride | 665.00 g | 665.00 g | 665.00 g | 665.00 g |
| Vitamin D3 | 359.00 g | 359.00 g | 359.00 g | 359.00 g |
| Biotin | 82.00 g | 82.00 g | 82.00 g | 82.00 g |
| Folic acid | 77.00 g | 77.00 g | 77.00 g | 77.00 g |
| Cyanocobalamin | 2.00 g | 2.00 g | 2.00 g | 2.00 g |
| Phylloquinone | 27.00 g | 27.00 g | 27.00 g | 27.00 g |
| Manganese sulfate | 51.00 g | 51.00 g | 51.00 g | 51.00 g |
| Sodium selenate | 1.10 g | 1.10 g | 1.10 g | 1.10 g |
| Calcium carbonate | 0-4 kg | 0-4 kg | 0-4 kg | 0-4 kg |
| Potassium phosphate monobasic | 0-32 kg | 0-32 kg | 0-32 kg | 0-32 kg |
| Potassium hydroxide | 24.00 kg | 24.00 kg | 24.00 kg | 24.00 kg |

| Ingredient (Per 18,000 pounds) | Ex. 69 | Ex. 70 | Ex. 71 | Ex. 72 |
|---|---|---|---|---|
| Nonfat milk solids | 7220.00 lbs | 7220.00 lbs | 7220.00 lbs | 7220.00 lbs |
| Corn syrup solids | 2870.00 lbs | 2870.00 lbs | 2870.00 lbs | 2870.00 lbs |
| Medium chain triglycerides | 1760.00 lbs | 1760.00 lbs | 1760.00 lbs | 1760.00 lbs |
| Whey protein concentrate | 3410.00 lbs | 3410.00 lbs | 3410.00 lbs | 3410.00 lbs |
| Tricalcium phosphate | 701.00 kg | 701.00 kg | 701.00 kg | 701.00 kg |
| 2'-FL | 82 kg | 327 kg | 645 kg | 1227 kg |
| Potassium citrate tribasic | 224.00 kg | 224.00 kg | 224.00 kg | 224.00 kg |
| Ascorbic acid | 136.00 kg | 136.00 kg | 136.00 kg | 136.00 kg |
| Magnesium chloride | 117.00 kg | 117.00 kg | 117.00 kg | 117.00 kg |
| Sodium chloride | 4.71 kg | 4.71 kg | 4.71 kg | 4.71 kg |
| m-Inositol | 11.00 kg | 11.00 kg | 11.00 kg | 11.00 kg |
| Sodium citrate tribasic | 23.90 kg | 23.90 kg | 23.90 kg | 23.90 kg |
| Ferrous sulfate | 4.00 kg | 4.00 kg | 4.00 kg | 4.00 kg |
| Soy lecithin | 16.80 kg | 16.80 kg | 16.80 kg | 16.80 kg |
| Zinc sulfate | 11.1 kg | 11.1 kg | 11.1 kg | 11.1 kg |
| Vitamin E acetate | 7.60 kg | 7.60 kg | 7.60 kg | 7.60 kg |

| Ingredient (Per 18,000 pounds) | Ex. 73 | Ex. 74 | Ex. 75 | Ex. 76 |
|---|---|---|---|---|
| Vitamin A palmitate | 2.40 kg | 2.40 kg | 2.40 kg | 2.40 kg |
| Niacinamide | 9.80 kg | 9.80 kg | 9.80 kg | 9.80 kg |
| Riboflavin | 1.1 kg | 1.1 kg | 1.1 kg | 1.1 kg |
| Calcium pantothenate | 4.40 kg | 4.40 kg | 4.40 kg | 4.40 kg |
| Cupric sulfate | 1.800 kg | 1.800 kg | 1.800 kg | 1.800 kg |
| Thiamine hydrochloride | 776.00 g | 776.00 g | 776.00 g | 776.00 g |
| Pyridoxine hydrochloride | 665.00 g | 665.00 g | 665.00 g | 665.00 g |
| Vitamin D3 | 359.00 g | 359.00 g | 359.00 g | 359.00 g |
| Biotin | 82.00 g | 82.00 g | 82.00 g | 82.00 g |
| Folic acid | 77.00 g | 77.00 g | 77.00 g | 77.00 g |
| Cyanocobalamin | 2.00 g | 2.00 g | 2.00 g | 2.00 g |
| Phylloquinone | 27.00 g | 27.00 g | 27.00 g | 27.00 g |
| Manganese sulfate | 51.00 g | 51.00 g | 51.00 g | 51.00 g |
| Sodium selenate | 1.10 g | 1.10 g | 1.10 g | 1.10 g |
| Calcium carbonate | 0-4 kg | 0-4 kg | 0-4 kg | 0-4 kg |
| Potassium phosphate monobasic | 0-32 kg | 0-32 kg | 0-32 kg | 0-32 kg |
| Potassium hydroxide | 24.00 kg | 24.00 kg | 24.00 kg | 24.00 kg |

| Ingredient (Per 18,000 pounds) | Ex. 73 | Ex. 74 | Ex. 75 | Ex. 76 |
|---|---|---|---|---|
| Nonfat milk solids | 7220.00 lbs | 7220.00 lbs | 7220.00 lbs | 7220.00 lbs |
| Corn syrup solids | 2870.00 lbs | 2870.00 lbs | 2870.00 lbs | 2870.00 lbs |
| Medium chain triglycerides | 1760.00 lbs | 1760.00 lbs | 1760.00 lbs | 1760.00 lbs |
| Whey protein concentrate | 3410.00 lbs | 3410.00 lbs | 3410.00 lbs | 3410.00 lbs |
| Tricalcium phosphate | 701.00 kg | 701.00 kg | 701.00 kg | 701.00 kg |
| 2'-FL | 82 kg | 327 kg | 645 kg | 1227 kg |
| Galactooligosaccharides | 164 kg | 350 kg | 650 kg | 818 kg |
| Potassium citrate tribasic | 224.00 kg | 224.00 kg | 224.00 kg | 224.00 kg |
| Ascorbic acid | 136.00 kg | 136.00 kg | 136.00 kg | 136.00 kg |
| Magnesium chloride | 117.00 kg | 117.00 kg | 117.00 kg | 117.00 kg |
| Sodium chloride | 4.71 kg | 4.71 kg | 4.71 kg | 4.71 kg |
| m-Inositol | 11.00 kg | 11.00 kg | 11.00 kg | 11.00 kg |
| Sodium citrate tribasic | 23.90 kg | 23.90 kg | 23.90 kg | 23.90 kg |
| Ferrous sulfate | 4.00 kg | 4.00 kg | 4.00 kg | 4.00 kg |
| Soy lecithin | 16.80 kg | 16.80 kg | 16.80 kg | 16.80 kg |
| Zinc sulfate | 11.1 kg | 11.1 kg | 11.1 kg | 11.1 kg |
| Vitamin E acetate | 7.60 kg | 7.60 kg | 7.60 kg | 7.60 kg |
| Vitamin A palmitate | 2.40 kg | 2.40 kg | 2.40 kg | 2.40 kg |
| Niacinamide | 9.80 kg | 9.80 kg | 9.80 kg | 9.80 kg |
| Riboflavin | 1.1 kg | 1.1 kg | 1.1 kg | 1.1 kg |
| Calcium pantothenate | 4.40 kg | 4.40 kg | 4.40 kg | 4.40 kg |
| Cupric sulfate | 1.800 kg | 1.800 kg | 1.800 kg | 1.800 kg |
| Thiamine hydrochloride | 776.00 g | 776.00 g | 776.00 g | 776.00 g |
| Pyridoxine hydrochloride | 665.00 g | 665.00 g | 665.00 g | 665.00 g |
| Vitamin D3 | 359.00 g | 359.00 g | 359.00 g | 359.00 g |
| Biotin | 82.00 g | 82.00 g | 82.00 g | 82.00 g |
| Folic acid | 77.00 g | 77.00 g | 77.00 g | 77.00 g |
| Cyanocobalamin | 2.00 g | 2.00 g | 2.00 g | 2.00 g |
| Phylloquinone | 27.00 g | 27.00 g | 27.00 g | 27.00 g |
| Manganese sulfate | 51.00 g | 51.00 g | 51.00 g | 51.00 g |
| Sodium selenate | 1.10 g | 1.10 g | 1.10 g | 1.10 g |
| Calcium carbonate | 0-4 kg | 0-4 kg | 0-4 kg | 0-4 kg |
| Potassium phosphate monobasic | 0-32 kg | 0-32 kg | 0-32 kg | 0-32 kg |
| Potassium hydroxide | 24.00 kg | 24.00 kg | 24.00 kg | 24.00 kg |

Example 77

In this Example, the effect of HMOs, and the dose-dependency thereof, on increasing the expression of TFF3 and other goblet cell genes that promote gastrointestinal healing by HMOs is analyzed.

Pooled HMOs are tested with respect to their ability to induce MUC2, TFF3, RELMβ, CHST5, and GAL3ST2 expression in the human LS174T cell culture model of goblet cells. The human LS174T colorectal cancer cell line is obtained from the American Type Culture Collection (ATCC). LS174T cells are maintained in minimum essential medium (MEM) supplemented with 10% Fetalplex (Gemini Biosciences), 1.5 g/L of $Na_2CO_3$, 10 ml/L penicillin G-streptomycin solution (Gemini Bio-products) at 37° C. in 5% $CO_2$. Pooled HMOs are obtained from Lars Bode (University of California, San Diego) and dissolved in cell culture grade water to required concentration. The solution is subsequently filter sterilized and used for cell culture studies. LS174T cells are treated with the media described above containing 0, 1, or 5 mg HMO/mL.

LS174T cells are collected and suspended in Trizol reagent and total RNA is isolated using the RNeasy Plus Kit (Qiagen) according to the manufacturer's instructions. The quality and quantity of RNA isolates are determined by Nanodrop (Thermo Fisher Scientific). RNA isolates are reverse transcribed using the High Capacity cDNA Reverse Transcription Kit (Applied Biosystems) to create cDNA, which is to assess gene expression via quantitative PCR.

For quantitative RT-PCR, specific TaqMAN gene expression assays are obtained from Applied Biosystems, which include expression assays for MUC2 (Hs00159374_m1), TFF3 (Hs00173625_m1), RELMβ (Hs00395669_m1), CHST5 (Hs00375495_m1), GAL3ST2 (Hs00223271_m1)

and GUSB (Hs99999908_m1). Quantitative real-time PCR is performed using TaqMAN PCR Master Mix (Applied Biosystems). Reactions are run in duplicates in a 384-well plate using an Applied Biosystems 7900HT Fast Real-Time PCR System. The results are analyzed using SDS 2.3 software and calculated by delta delta Ct method. All samples are normalized to Gus-β expression and fold induction is calculated over untreated controls. Gene expression is expressed as fold increase compared to HMO-free control cells. The experiment is repeated three times. Data represent means±SEM (n=3 plates per experiment). Statistical differences are indicated by different letters (P<0.05).

Figure 1B:
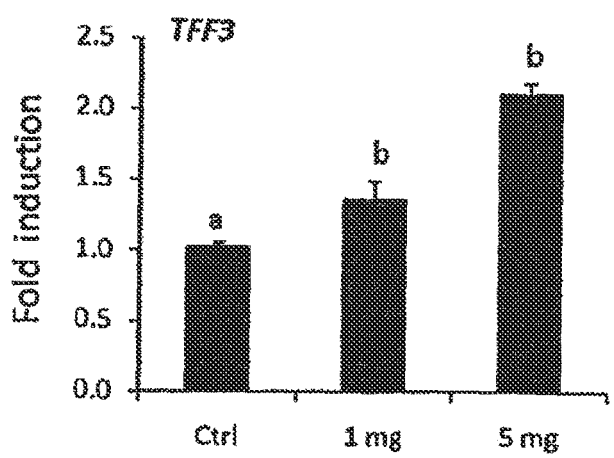
Figure 1C:
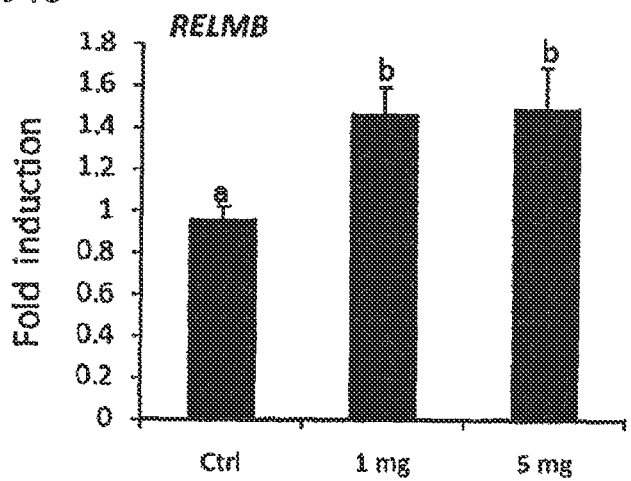
Figure 1D:
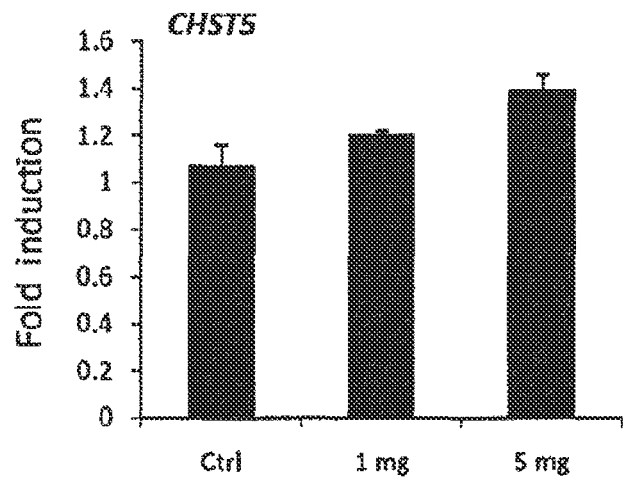
Figure 1E:
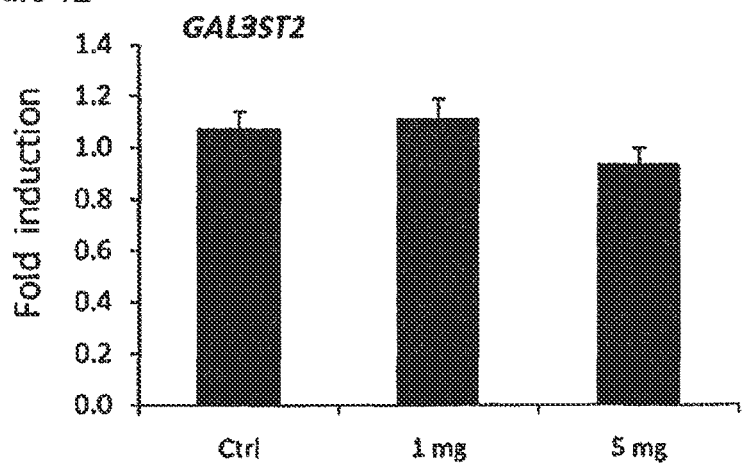

FIGS. 1A-1E represent the combined results of three replicate experiments. Specifically, FIGS. 1A, 1B, and 1C illustrate that the treatment with HMOs at a level of at least 1 mg/mL increases the expression of the MUC2, TFF3, and RELMβ genes compared to control cultures. Increased expression of goblet cell genes is specific and not universal, as evidenced by the minimal induction or lack of induction of CHST5 and GAL3ST2, respectively, by treatment with HMOs at either 1 mg/mL or 5 mg/mL.

In addition, FIGS. 1A and 1B indicate a dose dependent increase in expression of MUC2 and TFF3, with a modest induction (~1.5 fold) noted at the 1 mg/mL treatment level and more pronounced increases (~2 fold) at 5 mg/mL. In addition, the expression levels of RELMβ (FIG. 1C) were increased (~1.5 fold) at each of the 1 mg/mL treatment level and the 5 mg/mL treatment level. In contrast, gene expression of CHST5 (FIG. 1D) and GAL3ST2 (FIG. 1E) is not significantly impacted at any dose. As such, it can be concluded that the impact of HMOs on expression of several genes involved in the healing response of the gastrointestinal tract is dose-dependent.

These results indicate that HMOs promote the expression of several genes involved in the healing response of the GI tract. First, expression of TFF3, which HMOs are shown to enhance, has been positively associated with prevention and restitution of gastrointestinal damage to the epithelial cells in the intestine of mammals. Oral treatment with TFF3 reduces the damage associated with different forms of colitis in animal models. Additionally, HMOs induce the expression of MUC2, which provides a barrier that protects the gastrointestinal tract from infection and other sources of injury. Further, HMOs induce the expression of RELMβ, which is a protein associated with resolution of inflammation. Because tissue damage is difficult to heal when inflammation is abundant, the inflammation resolving effects of RELMβ induced by HMOs also supports healing. The combined impact of HMOs on expression of TFF3, MUC2, and RELMβ enables a product to support wound healing through its synergistic effects on cell healing, resolution of inflammation and promotion of barrier function.

Example 78

In this Example, the fermentation rates of several oligosaccharide substrates are measured in an in vitro model using infant fecal inocula.

Eight infant participants for feces donation were selected based on the following criteria: whether the infant: (1) was full term at birth with a gestational age of 38 to 42 weeks; (2) was at or above the fifth percentile for weight at birth; (3) has no maternal medical history of diabetes, tuberculosis, or perinatal infection with proven adverse effects on the fetus; (4) was a vaginal birth; (5) was at least 2 months of age at study entry, but not older than 4 months of age; (6) has no known cardiac, respiratory, gastrointestinal, or other systemic disease such as urinary tract infection or otitis media; (7) is free of history of blood group incompatibility serious enough to result in hematological problems; and (8) is not receiving any medications (except for supplemental vitamins) and has never received antibiotics. The eight infants are allowed to consume their normal diet of breast milk or infant formula. Four infants are exclusively breast fed and four infants are exclusively formula fed one of four commercially available infant formulas.

On the day of the in vitro experiments, a fecal sample is collected in the diaper and prepped within 15 min of defecation. For prepping, the sample is placed in a container with tepid water and analyzed. Fecal samples are diluted 1:10 (wt/vol) in anaerobic dilution solution prepared by blending the solution for 15 seconds in a blender under a stream of $CO_2$. Blended, diluted feces are filtered through four layers of cheesecloth and sealed in 125-mL serum bottles under $CO_2$. Inoculum is stored at 37° C. until inoculation of in vitro tubes.

Oligosaccharide test substrates evaluated for fermentation and growing of bacterium include (1) galactooligosaccharides 95 (GOS; Inalco group, Italy); (2) α-(2-6')-N-Acetyl-neuraminyl-lactose sodium salt (6'SL; Inalco group, Italy); (3) 2'-α-L-Fucopyranosyl-D-Lactose (2'FL; Inalco group, Italy); (4) Lacto-N-neotetraose (LNnT; Boehringer Mannheim, Germany); (5) Orafti® HP inulin (HP inulin; BENEO-Orafti, Belgium); and (6) gum arabic.

In Vitro Substrate Fermentation Model

Approximately 80 mg of each test substrate (1)-(6) is weighed in triplicate into 16-mL Balch tubes that are used in a conventional model that simulates large bowel fermentation. An aliquot (7.2 mL) of medium (Table 1; FIG. 2) is aseptically transferred into the Balch tubes, capped with butyl rubber stoppers, and sealed with aluminum caps. Tubes containing HP inulin and gum arabic are stored at 4° C. for approximately 12 h to enable hydration of the substrates before initiating fermentation. These tubes are placed in a 37° C. water bath approximately 30 min before inoculation. Tubes containing GOS, 6'SL, 2'FL, and LNnT are hydrated upon obtaining a fecal sample and placed in a 37° C. water bath until inoculation.

Sample and blank tubes are aseptically inoculated with 0.8 ml of diluted feces. Tubes are incubated at 37° C. with periodic mixing every 2 h for up to 12 h. At 0, 3, 6, and 12 h after inoculation, tubes are removed from the 37° C. incubator and processed immediately for analyses. A 3-ml subsample of fluid is collected and used for branched chain fatty acid analysis, and in particular isobutyrate analysis, which is an indicator of fermentation and improves gastrointestinal healing as described further below.

Branched-Chain Fatty Acid (BCFA) Analysis

BCFA Analysis: provides an indication of the extent of protein or amino acid fermentation. The amount of BCFA that accumulates in a bacteria culture also indicates how much fermentable carbohydrate is available for bacterial growth; that is, if there is sufficient fermentable carbohydrate present, the bacteria are able to generate ATP, which, in turn, allows them to incorporate the amino acid and ammonia nitrogen into bacterial protein. If there is insufficient fermentable carbohydrate present, bacteria will ferment protein and amino acids in order to obtain energy.

The 3-mL aliquot of fluid removed from the sample tubes for BCFA analysis is immediately added to 0.75 mL of 25% metaphosphoric acid. Concentrations of isobutyrate are determined using a Hewlett-Packard 5890A series II gas chromatograph (Palo Alto, Calif.) and a glass column (180 cm×4 mm i.d.) packed with 10% SP-1200/1% $H_3PO_4$ on 80/100+ mesh Chromosorb WAW (Supelco Inc., Bellefonte, Pa.). Oven temperature, detector temperature, and injector temperature are 125, 175, and 180° C., respectively. BCFA concentration values are corrected for blank tube production of BCFA and 0 h concentrations for each substrate. Total BCFA are calculated as the total amount of valerate, isovalerate, and isobutyrate.

Results and Discussion

Figure 3:
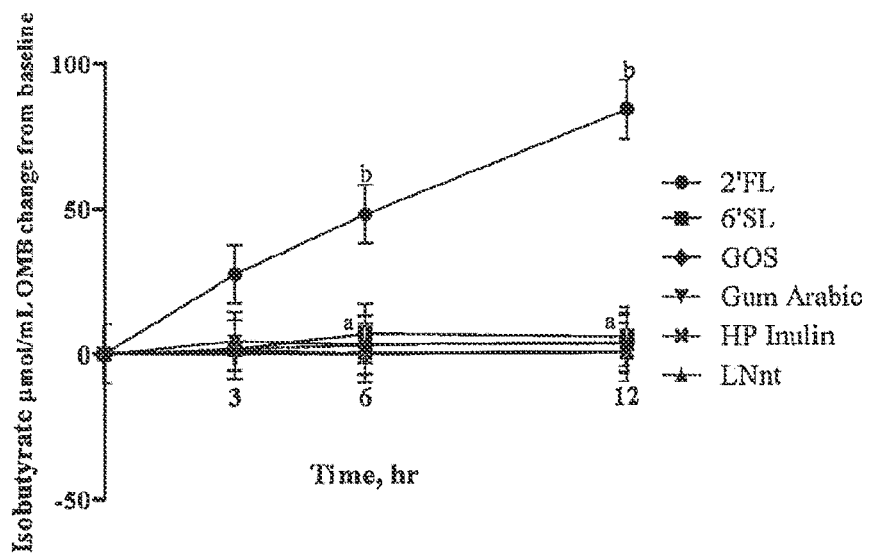
FIG. 3 is a graph depicting the change in isobutyrate production over time as affected by the various oligosaccharide substrates as tested in Example 78.
Figure 4A:
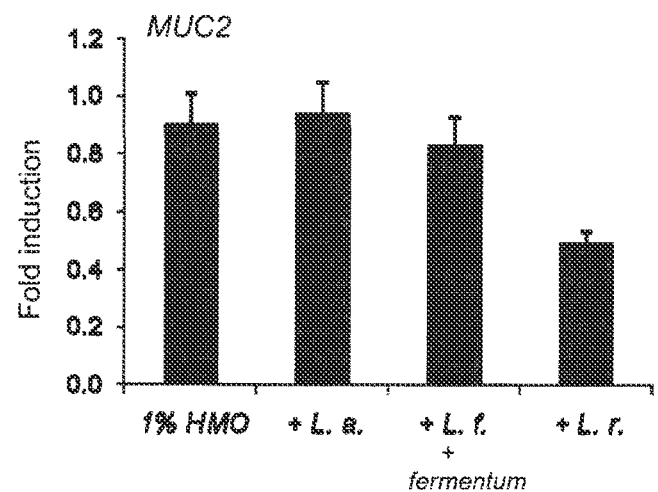
FIGS. 4A-4D are charts depicting the effect of the combinations of HMOs and *Lactobacillus acidophilus, Lactobacillus fermentum,* or *Lactobacillus rhamnosus* on the expression of several genes involved in the healing response of the gastrointestinal tract as measured in Example 79.
Figure 4B:
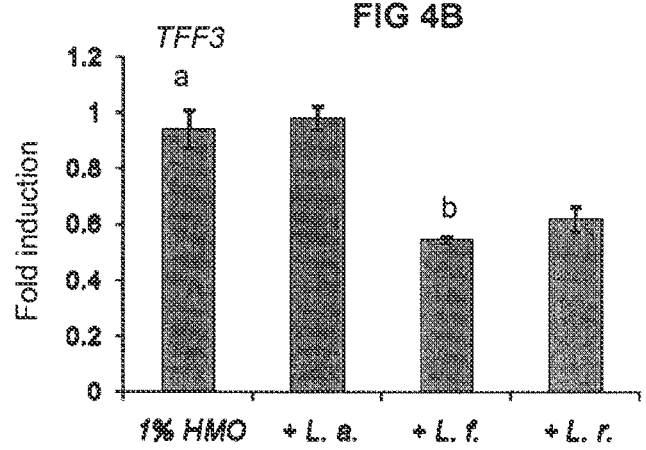
Figure 4C:
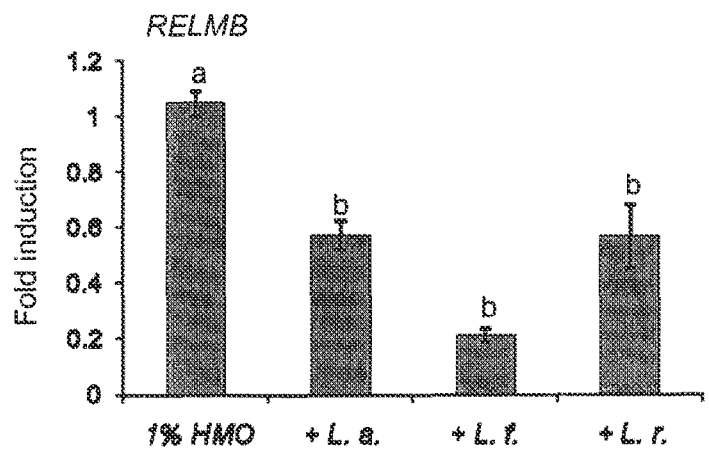
Figure 4D:
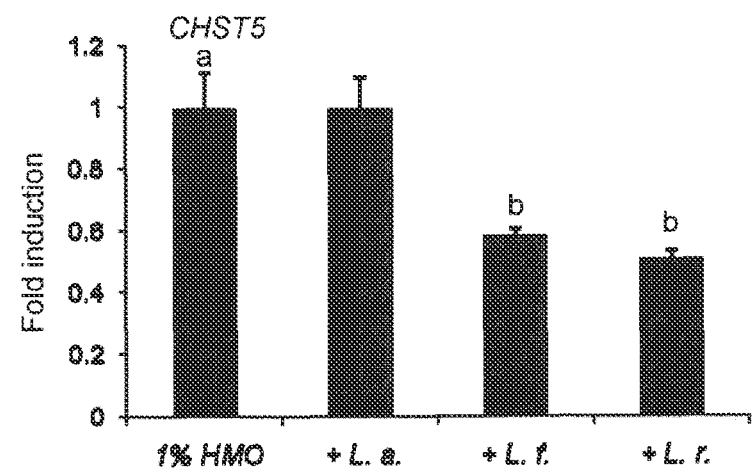
Figure 5C:
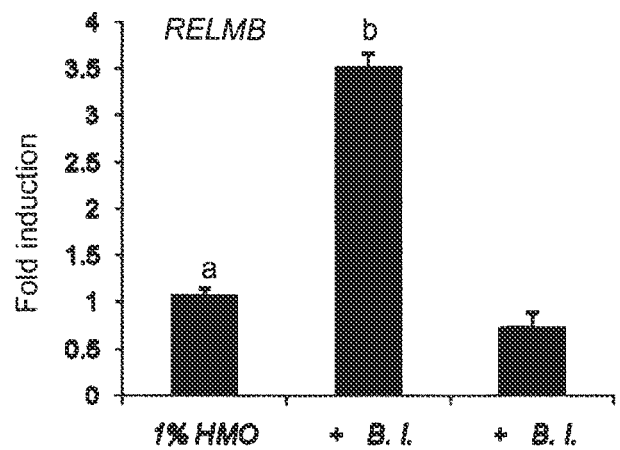
Figure 5D:
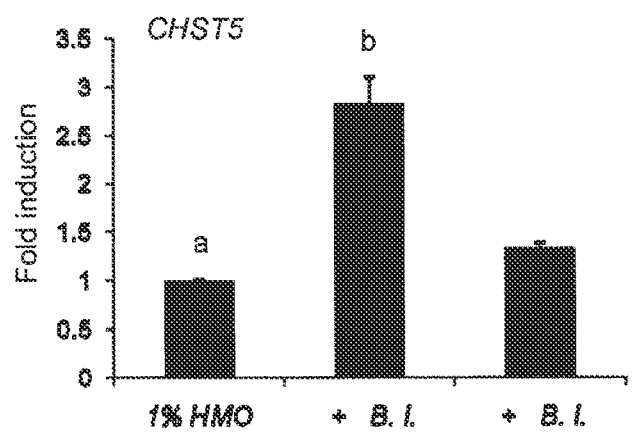

Isobutyrate production is similar over time within each substrate with the exception of 2'-FL. Specifically, cultures that are incubated with 2'-FL produce approximately 5 and 10-fold greater concentrations of isobutyrate at 6 and 12 hours, respectively, than any of the other substrates (P<0.05) (FIG. 3).

Conclusions from Fermentation Analysis

As shown in the data and Figures discussed above, 2'FL is readily fermented by infant fecal bacteria and enhances the production of isobutyrate as compared to other substrates, which improves gastrointestinal healing. Specifically, without being bound to any particular theory, under normal feeding conditions, colonocytes prefer to utilize butyrate as an energy source versus other short-chain fatty acids. During extended periods of starvation, however, such as would occur prior to feeding initiation in preterm infants following gastrointestinal surgery, colonocytes have impaired ability to oxidize butyrate, but retain exceptional ability to utilize isobutyrate for energy and analpleurosis. As such, by increasing the amount of isobutyrate produced through the administration of 2'-FL, gastrointestinal healing can be improved.

Example 79

In this Example, the ability of HMOs to promote the ability of probiotics to induce expression of TFF3 and other goblet cells is analyzed.

HMOs are tested with respect to their impact on the ability of probiotics to induce MUC-2, TFF3, RELMβ, and CHST5 expression in the human LS 174T cell culture model of goblet cells. The human LS174T colorectal cancer cell line is obtained from the American Type Culture Collection (ATCC). LS174T cells are maintained in minimum essential medium (MEM) supplemented with 10% Fetalplex (Gemini Biosciences), 1.5 g/L of $Na_2CO_3$, 10 ml/L penicillin G-streptomycin solution (Gemini Bio-products) at 37° C. in 5% $CO_2$. Pooled HMOs are obtained from Lars Bode (University of California, San Diego). The solution is subsequently filter sterilized and used for cell culture studies.

Probiotic *Bifidobacterium lactis* (B.l.) and *Bifidobacterium infantis* (B.i.) cultures are grown in sMRS supplemented with 0.5 g/L cysteine in the presence of 1% glucose or 1% HMO while probiotic *Lactobacillus acidophilus* (L.a.), *Lactobacillus fermentum* (L.f.), and *Lactobacillus rhamnosus* (L.r.) cultures are grown in sMRS in the presence of 1% glucose or 1% HMO. Culture O.D. is measured at 600 nm and at stationary phase the culture supernatant is collected after centrifugation at 4000 rpm for 5 min. The culture supernatants are subsequently filter sterilized and lyophilized. The lyophilized products are herein named the "postbiotic" fraction. Bacterial culture media containing 1% HMO or 1% glucose but not inoculated with probiotic is filtered, lyophilized, and used as the controls for the postbiotic fractions. Postbiotic fractions and control fractions are then added to MEM to represent "postbiotic" and control media, respectively. LS174T cells are treated with postbiotic and control media for 72 hours.

At the end of the incubation period, the LS174T cells are collected and suspended in Trizol reagent. Total RNA is isolated using the RNeasy Plus Kit (Qiagen) according to the manufacturer's instructions. The quality and quantity of RNA isolates are determined by Nanodrop (Thermo Fisher Scientific). RNA isolates are reverse transcribed using the High Capacity cDNA Reverse Transcription Kit (Applied Biosystems) to create cDNA, which is to assess gene expression via quantitative Real-time PCR. Specific TaqMAN gene expression assays are obtained from Applied Biosystems, which include expression assays for MUC-2 (Hs00159374_m1), TFF3 (Hs00173625_m1), RELMB (Hs00395669_m1), CHST5 (Hs00375495_m1), GAL3ST2 (Hs00223271_m1) and GUSB (Hs99999908_m1). Quantitative real-time PCR is performed using TaqMAN PCR Master Mix (Applied Biosystems). Reactions are run in duplicates in a 384-well plate using an Applied Biosystems 7900HT Fast Real-Time PCR System. The results are analyzed using SDS 2.3 software and calculated by delta delta Ct method. All samples are normalized to Gus-β expression and fold induction is calculated over untreated controls. Gene expression is expressed as fold increase compared to HMO-free control cells. Data represent means+SEM (n=3). Statistical differences are indicated by different letters (P<0.05).

FIGS. 4A-4D report the impact of treatment with the *L. acidophilus, L. fermentum*, and *L. rhamnosus* postbiotic fraction vs. control fractions on the expression of goblet cell products that promote gastrointestinal healing in LS174T cell cultures, and FIGS. 5A-5D report the impact of treatment with the *B. infantis* and *B. lactis* postbiotic fraction vs. control fractions on the expression of goblet cell products that promote gastrointestinal healing in LS174T cell cultures. Treatment of those cells with *B. infantis* postbiotic fraction significantly increases the expression of RELMβ and CHST5 (by 3.5 and 3-fold, respectively). The *L. acidophilus, L. fermentum*, and *L. rhamnosus* postbiotics do not increase the expression of MUC2, TFF3, RELMβ, or CHST5. MUC-2 and TFF3 expression are not significantly increased by treatment with either *Bifidobacterium* postbiotic fraction.

These results indicate that incubation of probiotic *B. infantis* with HMOs results in production of a supernatant "postbiotic" that induces the expression of genes that can promote gastrointestinal healing. This postbiotic fraction is a model of the products that a probiotic, such as *B. infantis*, would produce when exposed to HMOs when in the lumen of an infant's gastrointestinal tract. Therefore, these data indicate that infants fed formulas including HMOs and *B. infantis* are provided with greater gastrointestinal protection than those given formulas with *B. infantis* or HMOs alone.

What is claimed is:

1. A method of stimulating the healing response of an individual's gastrointestinal tract, the method comprising:
    administering a nutritional composition comprising a human milk oligosaccharide selected from the group consisting of 3'-sialyllactose, 6'-sialyllactose, 2'-fucosyllactose, 3-fucosyllactose, lacto-N-neotetraose, disialyllacto-N-tetraose, and combinations thereof to an individual having an injured gastrointestinal tract, wherein the individual's gastrointestinal tract is injured as a result of at least one of radiation therapy, chemotherapy, enteric infection, inflammatory bowel disease, colitis, and bowel obstruction;
    wherein the nutritional composition comprises 0.01 mg to less than 2 mg of the human milk oligosaccharide per mL of the composition, and wherein administration of the nutritional composition stimulates at least one mucin-associated protein selected from TFF3, MUC2, and RELMβ.

2. The method of claim 1 wherein the nutritional composition comprises 2'-Fucosyllactose.

3. The method of claim 1 wherein the nutritional composition further comprises at least one probiotic.

4. The method of claim 1, wherein the nutritional composition is selected from the group consisting of a human milk fortifier, an infant formula, a pediatric formula, a follow-on formula, and an adult nutritional composition.

5. The method of claim 4, wherein the nutritional composition is an infant formula.

6. The method of claim 4, wherein the nutritional composition comprises 2'-Fucosyllactose and at least one probiotic.

7. A method of reducing the incidence of intestinal mucosa injury, the method comprising:
   administering a nutritional composition comprising a human milk oligosaccharide selected from the group consisting of 3'-sialyllactose, 6'-sialyllactose, 2'-fucosyllactose, 3-fucosyllactose, lacto-N-neotetraose, disialyllacto-N-tetraose, and combinations thereof to an individual susceptible to an intestinal mucosa injury;
   wherein the nutritional composition comprises 0.01 mg to less than 2 mg of the human milk oligosaccharide per mL of the composition, and
   wherein administration of the nutritional composition stimulates at least one mucin-associated protein selected from TFF3, MUC2, and RELMβ.

8. The method of claim 7 wherein the nutritional composition comprises 2'-Fucosyllactose.

9. The method of claim 7 wherein the nutritional composition further comprises at least one probiotic.

10. The method of claim 7 wherein the nutritional composition is selected from the group consisting of a human milk fortifier, an infant formula, a pediatric formula, a follow on formula, and an adult nutritional composition.

11. A method of stimulating the expression of one or more mucin-associated proteins in an individual's gastrointestinal tract, the method comprising:
    administering a nutritional composition comprising a human milk oligosaccharide selected from the group consisting of 3'-sialyllactose, 6'-sialyllactose, 2'-fucosyllactose, 3-fucosyllactose, lacto-N-neotetraose, disialyllacto-N-tetraose, and combinations thereof to an individual in need thereof
    wherein the nutritional composition comprises 0.01 mg to less than 2 mg of the human milk oligosaccharide per mL of the composition, and
    wherein administration of the nutritional composition stimulates at least one mucin-associated protein selected from TFF3, MUC2, and RELMβ.

12. The method of claim 11 wherein the nutritional composition comprises 2'-Fucosyllactose.

13. The method of claim 11 wherein the nutritional composition further comprises at least one probiotic.

14. A method of reducing the incidence of inflammation in an individual's gastrointestinal tract, the method comprising:
    administering a nutritional composition comprising a human milk oligosaccharide selected from the group consisting of 3'-sialyllactose, 6'-sialyllactose, 2'-fucosyllactose, 3-fucosyllactose, lacto-N-neotetraose, disialyllacto-N-tetraose, and combinations thereof to an individual susceptible to inflammation of the gastrointestinal tract;
    wherein the nutritional composition comprises 0.01 mg to less than 2 mg of the human milk oligosaccharide per mL of the composition, and
    wherein administration of the nutritional composition stimulates at least one mucin-associated protein selected from TFF3, MUC2, and RELMβ.

* * * * *